United States Patent
Li et al.

(10) Patent No.: US 10,077,277 B2
(45) Date of Patent: Sep. 18, 2018

(54) BICYCLIC HETEROARYLAMINOALKYL PHENYL DERIVATIVES AS PI3K INHIBITORS

(71) Applicant: Incyte Corporation, Wilmington, DE (US)

(72) Inventors: Yun-Long Li, Chadds Ford, PA (US); Andrew P. Combs, Kennett Square, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 14/735,438

(22) Filed: Jun. 10, 2015

(65) Prior Publication Data

US 2015/0361094 A1   Dec. 17, 2015

Related U.S. Application Data

(60) Provisional application No. 62/010,760, filed on Jun. 11, 2014.

(51) Int. Cl.
| | | |
|---|---|---|
| *C07D 513/04* | (2006.01) | |
| *C07D 471/04* | (2006.01) | |
| *A61K 31/519* | (2006.01) | |
| *A61K 45/06* | (2006.01) | |

(52) U.S. Cl.
CPC .......... *C07D 513/04* (2013.01); *A61K 31/519* (2013.01); *A61K 45/06* (2013.01); *C07D 471/04* (2013.01)

(58) Field of Classification Search
CPC .... A61K 31/519; A61K 45/06; C07D 513/04; C07D 471/04
See application file for complete search history.

(56) References Cited

U.S. PATENT DOCUMENTS

| | | | |
|---|---|---|---|
| 3,037,980 A | 6/1962 | Hitchings et al. | |
| 3,169,967 A | 2/1965 | Schittler | |
| 3,506,643 A | 4/1970 | Thiel et al. | |
| 3,862,189 A | 1/1975 | Schwender et al. | |
| 3,936,454 A | 2/1976 | Schwender et al. | |
| 3,962,443 A | 6/1976 | Minami et al. | |
| 4,482,629 A | 11/1984 | Nakagawa et al. | |
| 4,840,951 A | 6/1989 | Iwasaki et al. | |
| 4,845,020 A | 7/1989 | Itoh et al. | |
| 4,861,701 A | 8/1989 | Burns et al. | |
| 5,124,331 A | 6/1992 | Arita et al. | |
| 5,208,250 A | 5/1993 | Cetenko et al. | |
| 5,252,580 A | 10/1993 | Takahashi et al. | |
| 5,294,620 A | 3/1994 | Ratcliffe et al. | |
| 5,314,883 A | 5/1994 | Tanikawa et al. | |
| 5,459,132 A | 10/1995 | Bru-Magniez et al. | |
| 5,521,184 A | 5/1996 | Zimmerman | |
| 5,646,153 A | 7/1997 | Spada et al. | |
| 5,811,439 A | 9/1998 | Ogawa et al. | |
| 5,866,702 A | 2/1999 | Mackman et al. | |
| 6,028,076 A | 2/2000 | Hirota et al. | |
| 6,342,501 B1 | 1/2002 | Townsend et al. | |
| 6,376,501 B1 | 4/2002 | Isobe et al. | |
| 6,392,047 B1 | 5/2002 | Geissler et al. | |
| 6,479,487 B1 | 11/2002 | Dumont et al. | |
| 6,630,496 B1 | 10/2003 | Seehra et al. | |
| 6,734,187 B1 | 5/2004 | Tanaka et al. | |
| 6,828,344 B1 | 12/2004 | Seehra et al. | |
| 7,129,264 B2 | 10/2006 | Smallheer et al. | |
| 7,494,987 B2 | 2/2009 | Akada et al. | |
| 7,495,002 B2 | 2/2009 | Langkopt et al. | |
| 7,528,143 B2 | 5/2009 | Noronha et al. | |
| 7,598,257 B2 | 10/2009 | Rodgers et al. | |
| 7,612,114 B2 | 11/2009 | Hamaoka et al. | |
| 8,680,108 B2 | 3/2014 | Li et al. | |
| 8,759,359 B2 | 6/2014 | Combs et al. | |
| 8,940,752 B2 | 1/2015 | Li et al. | |
| 9,096,600 B2 | 8/2015 | Li et al. | |
| 9,199,982 B2 | 12/2015 | Li et al. | |
| 9,249,087 B2 | 2/2016 | Kozikowski et al. | |
| 9,309,251 B2 | 4/2016 | Combs et al. | |
| 9,434,746 B2 | 9/2016 | Li et al. | |
| 9,527,848 B2 | 12/2016 | Li et al. | |
| 9,707,233 B2 | 7/2017 | Li et al. | |
| 9,730,939 B2 | 8/2017 | Li et al. | |
| 9,815,839 B2 | 11/2017 | Li et al. | |
| 2003/0008898 A1 | 1/2003 | Mahboobi et al. | |
| 2003/0157052 A1 | 8/2003 | Choe et al. | |
| 2004/0058930 A1 | 3/2004 | Belema et al. | |
| 2004/0063658 A1 | 4/2004 | Roberts et al. | |
| 2004/0067964 A1 | 4/2004 | Matsuoka et al. | |
| 2004/0142941 A1 | 7/2004 | Gudmundsson et al. | |

(Continued)

FOREIGN PATENT DOCUMENTS

| | | |
|---|---|---|
| AT | 388372 | 6/1989 |
| CA | 1066701 | 11/1979 |

(Continued)

OTHER PUBLICATIONS

"A to Z List of Cancers," National Cancer Institute (http://www.cancer.gov/) (Downloaded May 29, 2014), 22 pages.

(Continued)

*Primary Examiner* — Craig D Ricci
*Assistant Examiner* — Christopher R Stone
(74) *Attorney, Agent, or Firm* — Fish & Richardson P.C.

(57) ABSTRACT

This application relates to derivatives of Formula I:

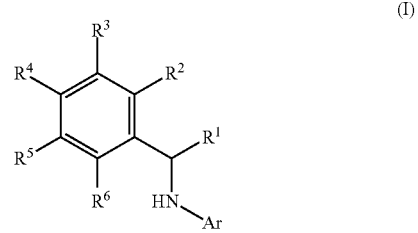

and pharmaceutically acceptable salts thereof, which are inhibitors of PI3K, and compositions and methods of treatment related thereto.

24 Claims, No Drawings

(56) References Cited

U.S. PATENT DOCUMENTS

| | | |
|---|---|---|
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikan et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298334 A1 | 11/2010 | Rodgers et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0059951 A1 | 3/2011 | Rodgers et al. |
| 2011/0098248 A1 | 4/2011 | Halcomb et al. |
| 2011/0105508 A1 | 5/2011 | Allen et al. |
| 2011/0166164 A1* | 7/2011 | Brewster ............ A01N 43/90 514/260.1 |
| 2011/0183985 A1 | 7/2011 | Li et al. |
| 2011/0190319 A1 | 8/2011 | Combs |
| 2011/0224155 A1 | 9/2011 | Tachdjian et al. |
| 2011/0224190 A1 | 9/2011 | Huang et al. |
| 2011/0281884 A1 | 11/2011 | Combs et al. |
| 2011/0312979 A1 | 12/2011 | Li et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2013/0018034 A1 | 1/2013 | Yao et al. |
| 2013/0029982 A1 | 1/2013 | Castro et al. |
| 2013/0045963 A1 | 2/2013 | Rodgers et al. |
| 2013/0059835 A1 | 3/2013 | Li et al. |
| 2013/0261101 A1 | 10/2013 | Combs et al. |
| 2014/0005166 A1 | 1/2014 | Rodgers et al. |
| 2014/0031355 A1 | 1/2014 | Fisher et al. |
| 2014/0057912 A1 | 2/2014 | Combs et al. |
| 2014/0066448 A1 | 3/2014 | Combs et al. |
| 2014/0121198 A1 | 5/2014 | Li et al. |
| 2014/0121222 A1 | 5/2014 | Li et al. |
| 2014/0249132 A1 | 9/2014 | Li et al. |
| 2014/0275127 A1 | 9/2014 | Combs et al. |
| 2014/0343030 A1 | 11/2014 | Li et al. |
| 2015/0284390 A1 | 10/2015 | Li et al. |
| 2016/0022685 A1 | 1/2016 | Li et al. |
| 2016/0024117 A1 | 1/2016 | Li et al. |
| 2016/0257689 A1 | 9/2016 | Qiao et al. |
| 2016/0264580 A1 | 9/2016 | Combs et al. |
| 2016/0362424 A1 | 12/2016 | Li et al. |
| 2016/0362425 A1 | 12/2016 | Li et al. |
| 2016/0362426 A1 | 12/2016 | Zhou et al. |
| 2017/0050987 A1 | 2/2017 | Li et al. |
| 2017/0158696 A1 | 6/2017 | Li et al. |

FOREIGN PATENT DOCUMENTS

| | | |
|---|---|---|
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |
| EP | 2050749 | 4/2009 |
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 1250316 | 10/1989 |
| JP | 4190232 | 7/1992 |
| JP | 9087282 | 3/1997 |
| JP | 9176116 | 7/1997 |
| JP | 10025294 | 1/1998 |
| JP | 10231297 | 9/1998 |
| JP | 2000080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011511761 | 4/2011 |
| JP | 2011136925 | 7/2011 |
| RU | 2233842 | 8/2004 |
| SU | 1712359 | 2/1992 |
| WO | WO 1993/16076 | 8/1993 |
| WO | WO 1993/22291 | 11/1993 |
| WO | WO 1993/25524 | 12/1993 |
| WO | WO 1999/43651 | 9/1999 |
| WO | WO 1999/43672 | 9/1999 |
| WO | WO 2000/09495 | 2/2000 |
| WO | WO 2000/044750 | 8/2000 |
| WO | WO 2000/053595 | 9/2000 |
| WO | WO 2001/014402 | 3/2001 |
| WO | WO 2001/064639 | 9/2001 |
| WO | WO 2001/064655 | 9/2001 |
| WO | WO 2001/072709 | 10/2001 |
| WO | WO 2002/000196 | 1/2002 |
| WO | WO 2002/006477 | 1/2002 |
| WO | WO 2002/024685 | 3/2002 |
| WO | WO 2002/064599 | 8/2002 |
| WO | WO 2002/064785 | 8/2002 |
| WO | WO 2002/078701 | 10/2002 |
| WO | WO 2003/020721 | 3/2003 |
| WO | WO 2003/024967 | 3/2003 |
| WO | WO 2003/029209 | 4/2003 |
| WO | WO 2003/037347 | 5/2003 |
| WO | WO 2003/044014 | 5/2003 |

(56) References Cited

FOREIGN PATENT DOCUMENTS

| | | |
|---|---|---|
| WO | WO 2003/049678 | 6/2003 |
| WO | WO 2003/050064 | 6/2003 |
| WO | WO 2003/068750 | 8/2003 |
| WO | WO 2003/074497 | 9/2003 |
| WO | WO 2003/099771 | 12/2003 |
| WO | WO 2004/005281 | 1/2004 |
| WO | WO 2004/024693 | 3/2004 |
| WO | WO 2004/046120 | 6/2004 |
| WO | WO 2004/048365 | 6/2004 |
| WO | WO 2004/056786 | 7/2004 |
| WO | WO 2004/069256 | 8/2004 |
| WO | WO 2004/076455 | 9/2004 |
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |
| WO | WO 2007/042806 | 4/2007 |
| WO | WO 2007/076092 | 7/2007 |
| WO | WO 2007/087548 | 8/2007 |
| WO | WO 2007/095588 | 8/2007 |
| WO | WO 2007/102392 | 9/2007 |
| WO | WO 2007/114926 | 10/2007 |
| WO | WO 2007/126841 | 11/2007 |
| WO | WO 2008/002490 | 1/2008 |
| WO | WO 2008/005303 | 1/2008 |
| WO | WO 2008/025821 | 3/2008 |
| WO | WO 2008/032033 | 3/2008 |
| WO | WO 2008/064018 | 5/2008 |
| WO | WO 2008/064157 | 5/2008 |
| WO | WO 2008/082490 | 7/2008 |
| WO | WO 2008/097991 | 8/2008 |
| WO | WO 2008/100867 | 8/2008 |
| WO | WO 2008/116129 | 9/2008 |
| WO | WO 2008/118454 | 10/2008 |
| WO | WO 2008/118468 | 10/2008 |
| WO | WO 2009/026701 | 3/2009 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/085230 | 7/2009 |
| WO | WO 2009/086123 | 7/2009 |
| WO | WO 2009/097446 | 8/2009 |
| WO | WO 2009/128520 | 10/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/130342 | 10/2011 |
| WO | WO 2011/146882 | 11/2011 |
| WO | WO 2011/156759 | 12/2011 |
| WO | WO 2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/125629 | 9/2012 |
| WO | WO 2012/135009 | 10/2012 |
| WO | WO 2013/033569 | 3/2013 |
| WO | WO 2013/052699 | 4/2013 |
| WO | WO 2013/151930 | 10/2013 |
| WO | WO 2016/183063 | 6/2016 |
| WO | WO 2016/138363 | 9/2016 |
| WO | WO 2016/183060 | 11/2016 |
| WO | WO 2016/183062 | 11/2016 |

OTHER PUBLICATIONS

"Angiogenesis" Merriam-Webster.com. Merriam-Webster, n.d. Web Jun. 16, 2014, www.merriam-webster.com/dictionary/angiogenesis, 3 pages.

"Arthritis: MedlinePlus Medical Encyclopedica," 2014, p. 1-5, accessed online Oct. 7, 2014; http://www.nlm.nih.gove/medlineplus/ency/article/001243.htm.

"Autoimmune disorders: MedlinePlus Medical Encyclopedia," 2013, p. 1-4, accessed online Oct. 7, 2014; http://www.nlm.nih.gov/medlineplus/ency/article/000816.htm.

"Adult Acute Myeloid Leukemia Treatment (PDQ®)—Patient Version, Last Modified Jul. 30, 2012," National Cancer Institute, [retrieved from the internet on Nov. 26, 2012] at http://www.cancer.gov/cancertopics/pdq/treatment/adultAML/Patient/page1, 5 pgs.

Ali, et al., "Essential role for the p110δ phosphoinositide 3-kinase in the allergic response," Nature. 2004, 431(7011):1007-11.

Allen, et al., "Synthesis of C-6 substituted pyrazolo[1,5-a]pyridines with potent activity against herpesviruses," *Bioorganic & Medicinal Chemistry* (2006), 14(4), 944-954.

Apsel et al., "Targeted polypharmacology: discovery of dual inhibitors of tyrosine and phosphoinositide kinases," Nat. Chem. Biol., 2008, 4(11): 691-699.

Bader, et al., "Cancer-specific mutations in PIK3CA are oncogenic in vivo," Proc Natl Acad Sci U S A. 2006, 103(5):1475-9.

Baek et al., "Complete remission induced by rituximab in refractory, seronegative, muscle-specific, kinase-positive myasthenia gravis," J Neurol Neurosurg Psychiatry, 2007, 78(7):771.

Ball, "PI3K inhibitors as potential therapeutics for autoimmune disease," Drug Discovery Today, 2014, pp. 1195-119.

Barber, et al., "PI3Kγ inhibition blocks glomerulonephritis and extends lifespan in a mouse model of systemic lupus," Nat Med. 2005, 11(9):933-5.

(56) References Cited

OTHER PUBLICATIONS

Barragan et al., "Protein Kinases in the Regulation of Apoptosis in B-cell Chronic Lymphocytic Leukemia," Leukemia and Lymphoma, 2003, 44(11):1865-1870.
Belema, et al., "Synthesis and structure-activity relationship of imidazo(1,2-a)thieno(3,2-e)pyrazines as IKK-β inhibitors," Bioorganic & Medicinal Chemistry Letters (2007), 17(15), 4284-4289.
Bendell, J.C., "Phase I, dose-escalation study of BKM120, an oral pan-Class I PI3K inhibitor, in patients with advanced solid tumors," Journal of Clincial Oncology (2011): JCO-2011.
Benistant, et al., "A specific function for phosphatidylinositol 3-kinase α (p85α-p110α) in cell survival and for phosphatidylinositol 3-kinase β (p85α-p110β) in de novo DNA synthesis of human colon carcinoma cells," Oncogene, 2000, 19(44):5083-90.
Bennasar, et al., "Generation and Intermolecular Reactions of 2-Indolylacyl Radicals," Organic Letters (2001), 3(11), 1697-1700, CODEN: ORLEF7; ISSN: 1523-7060.
Berge et al., "Pharmaceutical Salts," J Pharma Sci, 1977, 66(1):1-19.
Bergman, et al., "Synthesis of indolocarbazole quinones; potent aryl hydrocarbon receptor ligands," Tetrahedron (2002), 58(7), 1443-1452.
Bhatia and Rose, "Autoimmunity and autoimmune disease," Principles of Med Biol., 1996, 6:239-263, 244.
Bhovi, et al., "1,3-dipolar cycloaddition reaction: Synthesis and antimicrobial activity of some new3-ethoxycarbonyl-5-methoxy-6-bromo-2-triazolylmethylindoles," Indian Journal of Heterocyclic Chemistry (2004), 14(1), 15-18 CODEN: IJCHEI; ISSN: 0971-1627.
Billottet, et al., "A selective inhibitor of the p110δ isoform of PI 3-kinase inhibits AML cell proliferation and survival and increases the cytotoic effects of VP16," Oncogene. 2006, 25(50):6648-59.
Biswas, et al., "Synthesis of a trifluoromethylindolocarbazole, novel cyclic 27- and 36-membered N-benzyltri- and -tetraindoles, and an N-benzyltetraindolyltrimethane," Monatshefte fuer Chemie (1999), 130(10), 1227-1239, CODEN: MOCMB7; ISSN: 0026-9247.
Blom et al., Preparative LC-MS Purification: Improved Compound Specific Method Optimization, J. Combi. Chem. 2004, 6(6), 874-883.
Blom et al., "Two-Pump at Column Dilution Configuration for Preparative LC-MS," 2002, 4: 295.
Blom et al., "Optimizing Preparative LC-MS Configurations and Methods for Parallel Synthesis Purification," 2003, 5: 670.
Boger, et al., "First and Second Generation Total Synthesis of the Teicoplanin Aglycon," JACS, 123(9), 1862-1871, 2001.
Brachmann et al., "PI3K and mTOR inhibitors-a new generation of targeted anticancer agents," Current Opinion Cell Biol., 2009, 21:194-498.
Bringmann, et al., "Novel concepts in directed biaryl synthesis. Part 65. Synthesis and structure of a novel twofold lactone-bridged temaphthyl," Tetrahedron Letters (1998), 39(12), 1545-1548 CODEN: TELEAY; ISSN: 0040-4039.
Brock et al., "Roles of Gβγ in membrane recruitment and activation of p110γ/p101 phosphoinositide 3-kinaseγ," J Cell Biol., 2003, 160(1):89-99.
Brown, et al., "Small molecule inhibitors of IgE synthesis," Bioorganic & Medicinal Chemistry Letters (2006), 16(17), 4697-4699.
Cacoub et al., "Anti-CD20 monoclonal antibody (rituximab) treatment for cryoglobulinemic vasculitis: where do we stand?," Ann Rheum Dis, Mar. 2008, 67: 283-287.
Camps, et al., "Blockade of PI3Kγ suppresses joint inflammation and damage in mouse models of rheumatoid arthritis," Nat Med. 2005, 11(9):936-43.
Cannon, Burger's Medicinal Chemistry and Drug Discovery, Fifth Edition, vol. 1 Principles and Practice, Wiley-Interscience 1995, Ch. 19, pp, 783-803, 784.
Cantley, "The Phosphoinositide 3-Kinase Pathway," Science, (2002) 296 (5573):1655-7.

Castillo-Trivino, et al., "Rituximab in relapsing and progressive forms of multiple sclerosis: a systematic review," The PLoS One. Jul. 2013; 8(7):e66308. doi: 10.1371/journal.pone.0066308. Print 2013.
Chai, et al., "Synthesis and in vitro anti-hepatitis B virus activities of some ethyl 6-bromo-5-hydroxy-1H-indole-3-carboxylates," Bioorganic & Medicinal Chemistry (2006), 14(4), 911-917.
Chang, K-Y., "Novel phosphoinositide 3-kinase/mTOR dual inhibitor, NVP-BGT226, displays potent growth-inhibitory activity against human head and neck cancer cells in vitro and in vivo," Clinical Cancer Research 17.22 (2011): 7116-7126.
Chen, X., "Targeting oxidative stress in embryonal rhabdomyosarcoma," Cancer cell 24.6 (2013): 710-724.
Clayton, et al., "A Crucial Role for the p110δ Subunit of Phosphatidylinositol 3-Kinase in B Cell Development and Activation," J Exp Med. 2002, 196(6):753-63.
Collins et al., "Rituximab treatment of fibrillary glomerulonephritis," Am J Kidney Dis., 2008, 52(6):1158-62.
Coughlin et al., Approaches and limitations of phosphatidylinositol-3-kinase pathway activation status as a predictive biomarker in the clinical development of targeted theraphy, Breast Cancer Res Treatment, 2010, 124:1-11.
Courtney et al., "The PI3K Pathway as Drug Target in Human Cancer," J Clinc Oncol., 2010, 29:1075-1083.
Crabbe, "The PI3K inhibitor arsenal: choose your weapon!" Trends Biochem Sci., 2007, 32(10):450-56.
Dagia et al., A preferential p110α/γ PI3K inhibitor attenuates experimental inflammation by suppressing the production of proinflammatory mediators in a NF-κB-dependent manner, Am J Physiol—Cell Physiol., 2010, 298:929-941.
DeBerardinis et al., "The Biology of Cancer: Metabolic Reprogramming Fuels Cell Growth and Proliferation," Cell Metabolism, Jan. 2008, 7:11-20.
Delmas and Meunier, "The Management of Paget's Disease of Bone," N Engl J Med., 1997, 336:558-566.
Devauchelle-Pensec, "Treatment of Primary Sjogren Syndrome with Rituximab," Annal Internal Med., 2014, 160:233-242.
Dolezal et al., "Preparation and biological activity of 6-benzylaminopurine derivatives in plants and human cancer cells," Bioorganic & Medicinal Chemistry (2006), 14(3), 875-884.
Dolezal et al., "Preparation, biological activity and endogenous occurrence of N6-benzyladenosines," Bioorganic & Medicinal Chemistry (2007), 15(11), 3737-3747.
Dorokhov, et al., "Synthesis of functionalized pyrimidine-4-thiones and pyrido[2,3-d]pyrimidin-5-one derivatives from aminals of monoacylketenes", Izvestiya Akademii Nauk, Seriya Khimicheskaya (1993), (11), 1932-7.
Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," The Journal of Pharmacology and Experimental Therapeutics, 328(3):758-765, 2009.
Dushianthan et al., "Acute respiratory distress syndrome and acute lung injury," Post Graduate Med J., 2011, 87:612-622.
Engelman, "Targeting PI3K signalling in cancer: opportunities, challenges and limitations," Nature Rev: Cancer, 2009, 9:550-562.
Fadeyeva, et al., "Inhibitors of early virus-cell interaction stages among 3-ethoxycarbonyl-5-hydroxy-bromoindole derivatives," Khimiko-Farmatsevticheskii Zhurnal (1992), 26(9-10), 17-20 (with English abstract).
Fine et al., "Neoplasms of the Central Nervous System," Cancer Principles Practice Oncol., 2005, 2:1834-1887.
Flinn et al., "Preliminary evidence of clinical activity in a phase I study of CAL-101, a selective inhibitor of the p110δ isoform of phosphatidylinositol 3-kinase (PI3K), in patients with select hematologic malignancies," Journal of Clinical Oncology, (abstract), 27(15S):3543, 2009.
Floberg et al., "Extractive alkylation of 6-mercaptopurine and determination in plasma by gas chromatography-mass spectrometry," Journal of Chromatography, Biomedical Applications, (1981), 225(1), 73-81.
Fruman and Bismuth, "Fine Tuning the Immune Response with PI3K," Immunological Revs., 2006, 228:253-272.

(56) References Cited

OTHER PUBLICATIONS

Garvey, "Rituximab in the treatment of autoimmune haematolgoical disorders," British Journal of Haematology, 2008, 141: 149-169.
Gati et al., "(125I)Iodohydroxynitrobenzylthioinosine: a new high-affinity nucleoside transporter probe," Biochemistry and Cell Biology (1987), 65(5), 467-73.
Geng, et al., "Exploring 9-benzyl purines as inhibitors of glutamate racemase (MurI) in Gram-positive bacteria", Bioorganic & Medicinal Chemistry Letters (2008),18(15), 4368-4372.
Ghigo et al., "PI3K inhibition in inflammation: Toward tailored therapies for specific diseases," BioEssays, 2010, 32:185-196.
Godeau et al., "Rituximab efficacy and safety in adult splenectomy candidates with chronic immune thrombocytopenic purpura: results of a prospective multicenter phase 2 study," Blood, 2008, 112(4): 999-1004.
Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.
Granik, "Acetals of lactams and amides of acids. 40. Synthesis and hydrolytic splitting of mono- and bicyclic derivatives of 4-pyrimidinone", Khimiya Geterotsiklicheskikh Soedinenii (1984), (4),532-7 (with English abstract).
Greene and P. G. M. Wuts, Protective Groups in Organic Synthesis, 3rd Ed., Wiley & Sons, Inc., New York (1999).
Wuts and Greene, Protective Groups in Organic Synthesis, 4th ed., John Wiley & Sons: New Jersey, pp. 696-887,2007.
Harley, "Medical Management of Actue Renal Failure," Renal Failure Replacement Therapies, 2008, pp. 26-32.
Harris et al., "Alkyl 4-Chlorobenzoyloxycarbamates as Highly Effective Nitrogen Source Reagents for the Base-Free, Intermolecular Aminohydroxylation Reaction," J. Org. Chem., 76, 358-372, 2011.
Hauser et al., "B-Cell Depletion with Rituximab in Relapsing-Remitting Multiple Sclerosis," The New England Journal of Medicine, 358(7):676-688, 2008.
Hayter and Cook, "Updated assessment of the prevalence, spectrum and case definition of autoimmune disease," Autoimmunity Reviews, 2012, 11:754-765.
Hickey, et al., "BCR-ABL Regulates Phosphatidylinositol 3-Kinase-p110γ Transcription and Activation and is Required for Proliferation and Drug Resistance," J Biol Chem. 2006, 281(5):2441-50.
Hirose, et al., "Pyridone-carboxylic acids as antibacterial agents. I. Synthesis and antibacterial activity of 1-alkyl-1,4-dihydro-4-oxo-1,8- and -1,6-naphthyridine-3-carboxylic acids", Chemical & Pharmaceutical Bulletin (1982), 30(7), 2399-409.
Hirota "Efficient synthesis of 2,9-disubstituted 8-hydroxyadenine derivatives", Organic & Biomolecular Chemistry (2003), 1(8), 1354-1365.
Hirsch et al., "Taming the PI3K team to hold inflammation and cancer at bay," Pharmacology & Therapeutics, 2008, 118: 192-205.
Hosalkar et al., "Skeletal Trauma and Common Orthopedic Problems," Chpt 10, Khurana (ed.) Bone Pathology, 2009, 93 pages.
Huang et al., "Design and synthesis of a pyrido[2,3-d]pyrimidin-5-one class of anti-inflammatory FMS inhibitors,", Bioorganic & Medicinal Chemistry Letters (2008), 18(7), 2355-2361.
Huang et al., "Synthesis and bioassay of a fluorine-containing cytokinin, N6-pentafluoro-benzyladenosine," Youji Huaxue (1988), 8(2), 147-8 (with English abstract).
Ihle et al., "Inhibitors of phosphatidylinositol-3-kinase in cancer therapy", Molecular Aspects of Medicine, 31(2):135-144, 2010.
Irie, et al., "Discovery of selective and nonpeptidic cathepsin Sinhibitors," Bioorganic & Medicinal Chemistry Letters (2008), 18(14), 3959-3962.
Isobe, et al., "Synthesis and Biological Evaluation of Novel 9-Substituted-8-Hydroxyadenine Derivatives as Potent Interferon Inducers", Journal of Medicinal Chemistry (2006), 49(6),2088-2095.
Itaya, et al., "Syntheses of the marine ascidian purine aplidiamine and its 9-β-D-ribofuranoside," Tetrahedron Letters (1998), 39(26), 4695-4696.

Itaya, et al., "Synthesis and structure of the marine ascidian 8-oxoadenine aplidiamine," *Chemical & Pharmaceutical Bulletin* (1999), 47(9), 1297-1300.
Jager et al., "Molecular recognition. II Discrimination of specific and non-specific intermolecular interactions by means of magnetic resonance spectroscopy," *Magnetic Resonance in Chemistry* (1998), 36(3), 205-210, CODEN: MRCHEG; ISSN: 0749-1581.
Jager, et al., "Molecular recognition analyzed by EPR, ENDOR, and NMR spectroscopy," *Angewandte Chemie*, International Edition in English (1996), 35(16), 1815-1818.
Japanese Office Action in Japanese Application No. 2014-528654, dated Mar. 29, 2016, 5 pages (English Translation).
Jimenez, et al, "The p85 Regulator Subunit Controls Sequential Activation of Phosphoinositide 3-Kinase by Tyr Kinases and Ras," J Biol Chem., 2002, 277(44):41556-62.
Jou, et al., "Essential, Nonredundant Role for the Phosphoinositide 3-Kinase p110δ in Signaling by the B-Cell Receptor Complex," Mol Cell Biol. 2002, 22(24):8580-91.
Kang et al., "Aplidiamine, a unique zwitterionic benzyl hydroxyadenine from the Western Australian marine ascidian *Aplidiopsis* sp.," *Tetrahedron Letters* (1997), 38(6), 941-944.
Kang, et al., "Phosphtidylinositol 3-kinase mutations identified in human cancer are oncogenic," Proc Natl Acad Sci U S A. 2005, 102(3):802-7.
Karpouzas, et al., "Rituximab Therapy Induces Durable Remissions in Hispanic and African American Patients with Refractory Systemic Lupus Erythematosus (SLE)," Presented at 73th Annual Scientific Meeting of the American College of Rheumatology, Oct. 2009; Philadelphia, PA.
Kasibhatla, "Rationally Designed High-Affinity 2-Amino-6-halopurine Heat Shock Protein 90 Inhibitors That Exhibit Potent Antitumor Activity",Journal of Medicinal Chemistry (2007), 50(12),2767-2778.
Katritzky, et al., "Facile Synthesis of 2-Substituted Indoles and Indolo[3,2-]carbazoles from 2-(Benzotriazol-1-ylmethyl)indole," *Journal of Organic Chemistry* (1995), 60(11), 3401-4.
Kim et al., "A signaling network in Phenylephrine-Induced Benign Prostatic Hyperplasia," Endocrinology, 2009, 150:3576-3583.
Kim, et al., "A new structural class of S-adenosylhomocysteine hydrolase inhibitors", Bioorganic & Medicinal Chemistry (2009), 17(18), 6707-6714.
Kim, et al., "Synthesis and evaluation of antitumor activity of novel 1,4-naphthoquinone derivatives," *Archives of Pharmacal Research* (2006), 29(2), 123-130 CODEN: APHRDQ; ISSN: 0253-6269.
Knobbe, et al., "Genetic alteration and expression of the phosphoinositol-3-kinase/Akt pathway genes PIK3CA and PIKE in human glioblastomas," Neuropathol Appl Neurobiol. 2005, 31(5):486-90.
Kolasa, et al., "Synthesis of indolylalkoxyiminoalkylcarboxylates as leukotriene biosynthesis inhibitors," *Bioorganic & Medicinal Chemistry* (1997), 5(3), 507-514.
Kolliputi and Waxman, "IL-6 cytoprotection in hyperoxic acute lung injury occurs via PI3K/Akt-mediated Bax phosphorylation," Am J Physiol Lung Cellular Mole Physiol., 2009, 297:L6-L16.
Kong and Yamori, "Phosphatidylinositol 3-kinase inhibitors: promising drug candidates for cancer theraphy," Cancer Sci., 2008, 91734-1740.
Kong and Yamori, "Advances in Development of Phosphatidylinositol 3-Kinase Inhibitors," Current Medicinal Chemistry, 16:2839-2854, 2009.
Kuduk et al., "Heterocyclic fused pyridone carboxylic acid M1 positive allosteric modulators," *Bioorganic & Medicinal Chemistry Letters* (2010), 20(8), 2533-2537.
Kung et al., "Characterization of a Murine Model of Allergic Pulmonary Inflammation," Int. Arch. Allergy Immunol., (abstract), 105(1):83-90, 1994.
Kurimoto, et al., "Synthesis and Biological Evaluation of 8-Oxoadenine Derivatives as Toll-like Receptor 7 Agonists Introducing the Antedrug Concept", *Journal of Medicinal Chemistry* (2010), 53(7),2964-2972.
Kuster (ed), Kinase Inhibitors: Methods and Protocols Methods in Molecular Biology, 2012, 795:1-44.

(56) References Cited

OTHER PUBLICATIONS

Kutney, et al., "Dihydropyridines in synthesis and biosynthesis. IV. Dehydrosecodine, in vitro precursor of indole alkaloids," *Canadian Journal of Chemistry* (1982), 60(11), 1269-78.

Lee, et al., "Inhibition of phosphoinositide 3-kinase δ attenuates allergic airway inflammation and hyperresponsiveness in murine asthma model," FASEB J. 2006, 20(3):455-65.

Li et al., "Design, synthesis and antitumor activities of novel 4-anilino-5H-pyridazino[4,5-b]indoles," *Zhongnan Yaoxue* (2008), 6(2), 144-148, CODEN: ZYHAC6; ISSN: 1672-2981, Publisher: Zhongnan Yaoxue Zazhishe (with English abstract within the article).

Li et al., "Synthesis and antitumor activities of novel 1-anilino 5H-pyridazino[4,5-b]indoles," *Zhongguo Yaowu Huaxue Zazhi* (2007), 17(6), 339-343, CODEN: ZYHZEF; ISSN: 1005-0108 (with English abstract within the article).

Li, et al., "Optimization of the heterocyclic core of the quinazolinone-derived CXCR3 antagonists," *Bioorganic & Medicinal Chemistry Letters* (2008), 18(2), 688-693.

Li, et al., "Synthesis and anti-tumor activities of a novel series of tricyclic 1-anilino-5H-pyridazino[4,5-b]indoles," *Archiv der Pharmazie* (Weinheim, Germany) (2007), 340(8), 424-428, CODEN: ARPMAS; ISSN: 0365-6233.

Lindsay, et al., "SmI2-Promoted Radical Addition Reactions with N-(2-Indolylacyl)oxazolidinones: Synthesis of Bisindole Compounds," *Journal of Organic Chemistry* (2007), 72(11), 4181-4188, CODEN: JOCEAH; ISSN: 0022-3263.

Link, J. T., "The intramolecular Heck reaction," *Organic Reactions* (Hoboken, NJ, United States) (2002), 60, No pp. given CODEN: ORHNBA URL: http://www3.interscience.wiley.com/cgi-bin/mrwhome/107610747/HOME.

Lipsky, "Systemic lupus erythematosus: an autoimmune disease of B cell hyperactivity," Nat Immunol., 2001, 2(9):764-6.

Liu et al., "Inhibition of the mitotic kinesin Eg5 up-regulates Hsp70 through the phosphatidylinositol 3-kinase/Akt pathway in multiple myeloma cells," J Biol Chem., 2006, 281(26):18090-18097.

Liu et al., "mTOR mediated anti-cancer drug discovery," Drug Discovery Today: Therapeutic Strategies, 2009, 6:47-55.

Lovric et al., "Rituximab as rescue therapy in anti-neutrophil cytoplasmic antibody-associated vasculitis: a single-centre expereince with 15 patients," Nephrol Dial Transplant, 2009, 24: 179-185.

Lucas, et al., "Rauwolfia alkaloids. XXXI. The synthesis and activity of some reserpine analogs," *Journal of the American Chemical Society* (1959), 81, 1928-32.

Luo et al., "Principles of Cancer Therapy: Oncogene and Non-oncogene Addiction," Cell, 2009, 36:823-837.

Ma, et al., "Bromophenols Coupled with Nucleoside Bases and Brominated Tetrahydroisoquinolines from the Red Alga *Rhodomela confervoides*", Journal of Natural Products (2007), 70(3), 337-341.

Ma, et al., "Two new constituents from Artemisia capillaris Thunb", Molecules (2008), 13(2), 267-271.

Mahboobi, et al., "Bis(1H-2-indolyl)methanones as a Novel Class of Inhibitors of the Platelet-Derived Growth Factor Receptor Kinase," Journal of Medicinal Chemistry (2002), 45(5):1002-1018.

Martelli et al., "Targeting the PI3K/AKT/mTOR signaling network in acute myelogenous leukemia," Expert Opin Investig Drugs. Sep. 2009;18(9):1333-49.

Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", *J Medicinal Chem* (1975), 18(1), 74-9.

McDermott and Settleman, "Personalized Cancer Theraphy with Selective Kinase Inhibitors: An Emerging Paradigm in Medical Oncology," J Clinical Oncol., 2009, 27:5650-5659.

McLean, et al., "Discovery of covalent inhibitors for MIF tautomerase via cocrystal structures with phantom hits from virtual screening ," *Bioorganic & Medicinal Chemistry Letters* (2009), 19(23), 6717-6720.

McMahon, G., "VEGF Receptor Signaling in Tumor Angiogenesis," The Oncologist 5(1):3-10, 2000.

Meade, et al., "Anxiolytic activity of analogs of 4-benzylamino-2-methyl-7H-pyrrolo[2,3-d]pyrimidines," *European Journal of Medicinal Chemistry* (1998), 33(5), 363-374.

MedicineNet.com' [online]. "Definition of Cancer," Sep. 18, 2004, Retrieved on Sep. 16, 2005. Retrieved from the Internet: http://www.medterms.com, 1 page.

medpagetoday.com' [online] "Current Role of Rituximab in Systematic Lupus," Jan. 2015, [retrieved Apr. 24, 2015]. Retrieved from the Internet: URL <http://www.medpagetoday.com/Rheumatology/Lupus/49398#./149398?&_suid=14297429843880910545130428968 4>. 10 pages.

Meijer et al., "Treatment of primary Sjögren syndrome with rituximab: extended follow-up, safety and efficacy of retreatment," Ann. Rheum. Dis., 68(2):284-285, 2009.

Medeot et al., "Rituximab therapy in adult patients with relapsed or refractory immune thrombocytopenic purpura: long-term follow-up results," European Journal of Haematology, 2008, 81: 165-169.

Merrill, "Efficacy and safety of rituximab in moderately-to-severely active systemic lupus erythematosus: the randomized, double-blind, phase ii/iii systemic lupus erythematosus evaluation of rituximab trial," Arthritis & Rheumatism, 2010, 61(1):222-233.

Miki, et al., "Reaction of 1-benzylindole-2,3-dicarboxylic anhydride with 3-bromo-4-lithiopyridine: formal synthesis of ellipticine," *Heterocycles* (1998), 48(8), 1593-1597.

Miki, et al., "Reaction of indole-2,3-dicarboxylic anhydride with (3-bromo-4-pyridyl)triisopropoxytitanium: synthesis of ellipticine," *Tetrahedron Letters* (1996), 37(43), 7753-7754.

Miki, et al., "Synthesis of caulersin and its isomers by reaction of indole-2,3-dicarboxylic anhydrides with methyl indoleacetates," *Tetrahedron Letters* (2006), 47(29), 5215-5218, CODEN: TELEAY; ISSN: 0040-4039.

Miki, et al., "Synthesis of ellipticine by reaction of 1-(4-methoxybenzyl)indole-2,3-dicarboxylic anhydride with (3-bromo-4-pyridyl)triisopropoxytitanium," *Journal of the Chemical Society*, Perkin Transactions 1 (2001), (18), 2213-2216.

Mishra et al., "Decanuclear Copper Framework Supported by a Tripodal Adenine Ligand," *Inorganic Chemistry* (Washington, DC, United States), (2010), 49(8), 3691-3693.

Mizoguchi, et al., "Genetic Alterations of Phosphoinositide 3-kinase Subunit Genes in Human Glioblastomas," Brain Pathol. 2004, 14(4):372-7.

Moffett, "Antiulcer agents. p-Aminobenzamido aromatic compounds", Journal of Medicinal Chemistry (1971), 14(10), 963-8.

Mohammadizadeh, et al., "A novel and expedient synthesis of 7-pyrimidinylpyrimido[4,5-d]pyrimidinones," *Helvetica Chimica Acta* (2010), 93(1), 153-157.

Morrison, et al., "Pyrimido[4,5-c]pyridazines. 1. Cyclizations with α-keto esters", *Journal of Organic Chemistry* (1978), 43(25), 4844-9.

Mukhopadhyay, et al., "An ionic liquid {[secbmim]+ Br-} as a "dual reagent catalyst" for the multicomponent synthesis of (quinolinyl- and isoquinolinyl-amino) alkylnaphthols, their bis-analogs and a facile route to naphthoxazines," ARKIVOC (Gainesville, FL, United States) (2010), (10), 291-304.

Musmuca, et al., "Small-Molecule Interferon Inducers. Toward the Comprehension of the Molecular Determinants through Ligand-Based Approaches", Journal of Chemical Information and Modeling (2009),49(7), 1777-1786.

Najiwara, et al., "Behavior of naphthoyloxyl and methoxynaphthoyloxyl radicals generated from the photocleavage of dinaphthoyl peroxides and 1-(naphthoyloxy)-2-pyridones," *Bulletin of the Chemical Society of Japan* (2003), 76(3), 575-585.

Najiwara, et al., Generation and behavior of naphthoyloxyl radicals in photocleavage of 1-(naphthoyloxy)-2-pyridones, *Chemistry Letters* (2001), (10), 1064-1065.

Nettekoven, M., "A combinatorial approach towards 2-acyl-3-amino-indole derivatives," *Tetrahedron Letters* (2000), 41(43), 8251-8254.

Norman, P., "Selective PI3Kδ inhibitors , a review of the patent literature", Expert Opinion on Therapeutic Patents, Informa Healthcare, 21(11):1773-1790, 2011.

(56) References Cited

OTHER PUBLICATIONS

Oki, et al., "Reactivities of Stable Rotamers. XLII. Generation and Fates of Rotameric [1-(9-Fluorenyl)-2-naphthyl]methyl Radicals," *Bulletin of the Chemical Society of Japan* (1999), 72(10), 2327-2336.
Okkenhaug, et al., "Impaired B and T Cell Antigen Receptor Signaling in p110δ PI 3-Kinase Mutant Mice," Science, 2002, 297(5583):1031-4).
Park et al., Analytical Biochemistry 1999, 269, 94-104.
Park et al., "Phosphoinositide 3-kinase δ inhibitor as a novel therapeutic agent in asthma," Respirology, 13:764-771, 2008.
Phillips, et al., "The reaction of anils with 8-quinolinol," *Journal of Organic Chemistry* (1954), 19, 907-9 CODEN: JOCEAH; ISSN: 0022-3263.
Pinedo and Slamon, "Translational Research: The Role of VEGF in Tumor Angiogenesis," The Oncologist, 5(1):1-2, 2000.
Platts, et al., "A concise synthesis of HIV integrase inhibitors bearing the dipyridone acid motif," *Tetrahedron Letters* (2011), 52(4), 512-514.
Portnaya, et al., "Azomethine dyes. IV. Indoaniline dyes derived from heterocyclic N-substituted 1-hydroxy-2-naphthamides," *Ts. Vses. Nauchn.-Issled. Kinofotoinst.* (1960), (No. 40), 106-18 (with English abstract).
Prezent, et al., STN Abstract, Accession No. 2004:358794, "Boron chelates as intermediates in the synthesis of new functionalized pyridines and pyrimidines from α,α-dioxoketene aminals," *Boron Chemistry at the Beginning of the 21st Century*, [Proceedings of the International Conference on the Chemistry of Boron], 11th, Moscow, Russian Federation, Jul. 28-Aug. 1, 2002 (2003), Meeting Date 2002, 91-93. Editor(s): Bubnov, Yu. N. A. N. Nesmeyanov Institute of Organoelement Compounds, Russian Academy of Sciences: Moscow, Russia.
Puri and Gold, "Selective inhibitors of phosphoinositide 3-kinase delta: modulators of B-cell function with potential for treating autoimmune inflammatory diseases and B-cell malignancies," Frontiers in Immunology, 3(256):146, 2012.
Ramos-Casals et al., "Rituximab in systemic lupus erythematosus; A systematic review of off-label use in 188 cases," Lupus, 18:767-776, 2009.
Randis, et al., "Role of PI3Kδ and PI3Kγ in inflammatory arthritis and tissue localization of neutrophils," Eur. J. Immunol., 2008, 38(5):1215-24.
Reich, et al., "Preparation of a,b-unsaturated carbonyl compounds and nitriles by selenoxide elimination ," *Organic Reactions* (Hoboken, NJ, United States) (1993), 44, No pp. given.
Remington's Pharmaceutical Sciences, 17th ed., Mack Publishing Company, Easton, PA., 1985, p. 1418.
Ringshausen et al., "Constitutively Actived phosphatidylinositol-3-kinase (PI-3K) is involved in the defect of apoptosis is B-CLL: assocaite with protein kinase C delta," Blood, 2002, 100:3741-3748.
Roxas-Duncan, et al., "Identification and biochemical characterization of small-molecule inhibitors of Clostridium botulinum neurotoxin serotype A," *Antimicrobial Agents and Chemotherapy* (2009), 53(8), 3478-3486.
Sahoo, et al., "Antispasmodic compounds. IV," Journal of the Indian Chemical Society (1959), 36, 421-4.
Sako, M., "Product class 19: pyridopyrimidines," *Science of Synthesis* (2004), 16, 1155-1267.
Samuels and Ericson, "Oncogenic PI3K and its role in cancer," Curr Opin Oncol., 2006, 18(1):77-82.
Samuels, et al., "High Frequency of Mutations of the PIK3CA Gene in Human Cancers," Science, 2004, 304(5670):554.
Sasaki, et al., "Function of PI3Kγ in Thymocyte Development, T Cell Activation, and Neutrophil Migration," Science, 2000, 287(5455):1040-6.
Sawyers, "The cancer biomarker problem," Nature, 2008, 452:548-552.
Saxena, et al., "Pharmacophore-based virtual screening and docking studies on Hsp90 inhibitors", SAR and QSAR in Environmental Research (2010), 21(5-6), 445-462.

Schafer and Kolkhof, "Failure is an option: learning from unsuccessful proof-of-concept trials," Drug Discovery Today, Nov. 2008, 13(21/22):913-916.
Schell, et al., "Versatile Solid-Phase Synthesis of Trisubstituted 1H-Pyrido[2,3-d]pyrimidin-4-ones and Related Heterocycles," *Journal of Combinatorial Chemistry* (2005), 7(1), 96-98.
Selig et al., "The application of Stille cross-coupling reactions with multiple nitrogen containing heterocycles," Tetrahedron, Sep. 2011, 67(47): 9204-9213.
Segarra et al., "Successful treatment of membranous glomerulonephritis with rituximab in calcineurin inhibitor-dependent patients," Clin J Am Soc Nephrol., 2009, 4(6):1083-8.
Sen, et al., "Reaction of aldehydes and amines with 8-hydroxyquinaldine and 8-quinolinol. II," *Journal of the Indian Chemical Society* (1960), 37, 640-2.
Shi, et al., "Synthesis and preliminary cytotoxic evaluation of substituted indoles as potential anticancer agents," *Chinese Chemical Letters* (2007), 18(8), 899-901, CODEN: CCLEE7; ISSN: 1001-8417.
Shuttleworth et al., "Progress in the Preclinical Discovery and Clinical Development of Class 1 and Dual Class I/IV Phosphoinositide 3-Kinase (PI3K) Inhibitors", Current Medicinal Chemistry, 18(1):2686-2714, 2011.
Silverman, R. B., "The organic Chemistry of Drugs Design and Drug Action." Elsevier. Northwestern University. Second Edition. Evanstons Illinois. 2004. p. 29 and table 2.2.
Singh et al., "Application of Nazarov cyclization to access [6-5-6] and [6-5-5]tricyclic core embedded new heterocycles: an easy entry to structures related to Taiwaniaquinoids," *Organic & Biomolecular Chemistry* (2009), 7(9), 1858-1867, CODEN: OBCRAK; ISSN: 1477-0520.
Steliou, et al., "Does diatomic sulfur(S2) react as a free species?", *Journal of the American Chemical Society* (1992), 114(4), 1456-62.
Stüve et al., "Long-term B-Lymphocyte Depletion With Rituximab in Patients With Relapsing-Remitting Multiple Sclerosis," Arch. Neurol., 66(2):259-261, 2009.
Sujobert, et al., "Essential role for the p110δ isoform in phosphoinositide 3-kinase activation and cell proliferation in acute myeloid leukemia," Blood, 2005, 106(3):1063-6.
Szuecova, et al., "Synthesis, characterization and biological activity of ring-substituted 6-benzylamino-9-tetrahydropyran-2-yl and 9-tetrahydrofuran-2-ylpurine derivatives," *Bioorganic & Medicinal Chemistry* (2009), 17(5), 1938-1947.
Terrier, et al., "Tolerance and Efficacy of Rituximab (RTX) in Systemic Lupus Erythematosus (SLE): Data of 104 Patients From the AIR (Auto-immunity and Rituximab) Registry," Presented at 73th Annual Scientific Meeting of the American College of Rheumatology, Oct. 2009; Philadelphia, PA.
Thomas, et al., "Airway inflammation: chemokine-induced neutrophilia and the class I phosphoinositide 3-kinases," Eur J Immunol. 2005, 35(4):1283-91.
Travnickek, et al., "2-Chloro-6-[(4-hydroxy-3,5-dimethoxybenzyl)amino]-9-isopropylpurine," *Acta Crystallographica*, Section E: Structure Reports Online (2007), E63(2), o728-o730 CODEN: ACSEBH; ISSN: 1600-5368 URL: http://journals.iucr.org/e/issues/2007/02/00/1h2285/1h2285.pdf.
Umar, A., "Future directions in cancer prevention," Nature Reviews Cancer, 12.12 (2012): 835-848.
Uddin et al., "Role of phosphatidylinositol 3'-kinase/AKT pathway in diffuse large B-cell lymphomas survival," Blood, 2006, 108:4178-4186.
Vanhaesebroeck et al., "Signalling by PI3K isoforms: insights from gene-targeted mice," Trends Biochem Sci., 2005, 30(4):194-204.
Vasil'ev, et al, "Chelate synthesis of 1-alkyl-5-(trifluoromethyl)-1,6-naphthyridin-4(1H)-ones", Izvestiya Akademii Nauk, Seriya Khimicheskaya (1994),(8), 1510-11 (with English abstract).
Venet et al., "Lymphocytes in the Development of Lung Inflammation: A role of Regulatory CD4+ T Cells in Indirect Pulmonary Lung Injury," J Immunol., 2009, 183:6472-3480.
Wallin, J.J., "GDC-0980 is a novel class I PI3K/mTOR kinase inhibitor with robust activity in cancer models driven by the PI3K pathway," Molecular cancer therapeutics 10.12 (2011): 2426-2436.

(56) References Cited

OTHER PUBLICATIONS

Walsh and Jayne, "Rituximab in the treatment of anti-neutrophil cytoplasm antibody associated vasculitis and systemic lupus erythematosis: past, present and future," Kidney International, 2007, 72: 676-682.
WebMD. Arthritis Health Center: What is Inflammation? Jul. 6, 2012 www.webmd.com/arthritis/about-inflammation?page=2, 4 pages.
WebMD. Bladder Cancer Health Center: Bladder Cancer-Prevention, Apr. 30, 2013 www.webmd.com/cancer/bladder-cancer/bladder-cancer-prevention, 1 page.
WebMD. Lung Disease & Respiratory Health Center: ARDS, May 21, 2014, www.webmd.com/lung/ards-acute-respiratory-distress-syndrome?page=2, 4 pages.
WebMD. Lung Disease & Respiratory Health Center: Lung Disease Overview, May 23, 2014, www.webmd.com/lung/lung-diseases-overview, 3 pages.
WebMD. Osteoarthritis Health Center: Osteoarthritis-prevention, Apr. 9, 2013, www.webmd.com/osteoarthritis/tc/osteoarthritis-prevention, 2 pages.
WebMD. Psoriasis Health Center: Psoriasis-prevention, Jan. 9, 2012, www.webmd.com/skin-problems-and-treatments/psoriasis/psoriasis-prevention, 1 page.
Xu et al., "Activation of the PI3K/AKT/mTOR pathway in diffuse large B cell lymphoma: clinical significance and inhibitory effect of rituxmab," Ann Hematol., 2013, 92:1351-1358.
Yaguchi et al., "Antitumor Activity of ZSTK474, a new Phosphatidinylinositol 3-Kinase Inhibitor," *J Natl. Cancer Inst.*, 2006, 98(8):545-556.
Yahay-Zadeh, "Synthesis of 9-Aryl-6-aminopurines from 5-Amino-1-aryl-IH-imidazole-4-carbonitriles", Russian Journal of Organic Chemistry (Translation of Zhurnal Organicheskoi Khimii) (2003), 39(11),1649-1651.
Yahyazadeh, et al., "Synthesis of 9-benzyl-6-aminopurines from 5-amino-1-benzyl-4-cyanoimidazoles", Bulletin of the Korean Chemical Society (2003), 24(12), 1723-1724.
Yamada et al., "Alpha-1 Adrenoceptors in Human Prostate: Characterization and Alteration in Benign Prostatic Hypertrophy," J Pharmacol Experimental Therapeutics, 1987, 242(1):326-330.
Yanni, A. S., "Synthesis of some new 5-iodo-7-substituted-aminomethyl-8-hydroxyquinoline," *Revue Roumaine de Chimie* (1994), 39(7), 833-6 CODEN: RRCHAX; ISSN: 0035-3930.
Yanni, et al., "Synthesis and biological activity of some 7-substituted aminomethyl-8-hydroxyquinoline-5-sulfonic acids," *Indian Journal of Chemistry, Section B: Organic Chemistry Including Medicinal Chemistry* (1982), 21B(7), 705-6.
Yoo, et al., "Synthesis and evaluation of antitumor activity of novel 2-[N-methyl-N-(4-methyl-1,3-benzothiazol-2-yl)aminomethyl]-5,8-diacyloxy -1,4-naphthoquinones," *Archives of Pharmacal Research* (2008), 31(2), 142-147 CODEN: APHRDQ; ISSN: 0253-6269.
Yoon et al., "Impact of fluoroquinolones on the diagnosis of pulmonary tuberculosis initially treated as bacterial pneumonia," Int'l J Tuberculosis and Lung Dis, 2005, 9:1215-1219.
Yoshida, et al., "MexAB-OprM specific efflux pump inhibitors in Pseudomonas aeruginosa. Part 5: Carbon-substituted analogues at the C-2 position," *Bioorganic & Medicinal Chemistry* (2006), 14(6), 1993-2004.
Yuan, T.L., "PI3K pathway alterations in cancer: variations on a theme," Oncogene, 2008, 27.41:5497-551.
Zhang et al., "Advances in preclinical small molecules for the treatment of NSCLC", Expert Opinion on Therapeutic Patents, 19(6):731-751, 2009.
Zhao and Vogt, "Class I PI3K in oncogenic cellular transformation," Oncogene, 2008, 27:5486-5496.
Zhao, et al., "Synthesis and in vitro anti-hepatitis B virus activities of some ethyl 5-hydroxy-1H-indole-3-carboxylates," *Bioorganic & Medicinal Chemistry* (2006), 14(8), 2552-2558.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).
International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patentability for PCT/US2012/030310 dated Oct. 1, 2013 (7pgs.).
International Preliminary Report on Patentability for PCT/US2012/028915 dated Sep. 17, 2013 (6pgs.).
International Preliminary Report on Patentability for PCT/US2012/053398, dated Mar. 4, 2014 (6 pgs.).
International Search Report dated Jul. 11, 2013 for International Appln. No. PCT/US2013/034803 (15 pgs.).
International Search Report dated Dec. 21, 2012 for International Appln. No. PCT/US2012/053398 (11 pgs.).
International Search Report dated Feb. 28, 2012 for International Appln. No. PCT/US2011/065743 (13 pgs.).
International Search Report dated May 11, 2012 for International Appln. No. PCT/US2012/030310 (11 pgs.).
International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar. 15, 2011 (12 pgs.).
International Search Report for PCT/US2010/061023 dated Feb. 16, 2011 (10 pgs.).
International Search Report for PCT/US2011/032213 dated Jun. 14, 2011 (11 pgs.).
STN Search Report, conducted Dec. 1, 2010, 132 pages.
STN Search Report, conducted Dec. 16, 2009, 72 pages.
STN Search Report, conducted prior to Jun. 21, 2011, 224 pages.
STN Search Report, conducted Apr. 5, 2010, 513 pages.
STN Search Report, conducted Apr. 24, 2009, 43 pages.
STN Search Report, conducted Dec. 7, 2010, 213 pages.
STN Search Report, conducted Aug. 29, 2011, 181 pages.
STN Search Report, conducted May 27, 2009, 2 pages.
STN Search Report, conducted May 28, 2009, 81 pages.
STN Search Report, conducted Apr. 2, 2010, 141 pages.
STN Search Report, conducted Aug. 30, 2011, 61 pages.
Office Action in CO Application No. 11-479.464, dated Mar. 14, 2014, 17 pages.
Office Action in JP Application No. 2012-518563, dated Jul. 8, 2014, 6 pages (with English translation).
Office Action in JP Application No. 2013-546274, dated Sep. 15, 2015, 7 pages (with English Translation).
Office Action in JP Application No. 2014-223540, dated Jul. 21, 2015, 5 pages. (with English Translation).
International Search Report and Written Opinion in International Application No. PCT/US2016/031606, dated Jun. 20, 2016, 10 pages.
International Search Report and Written Opinion in International Application No. PCT/US2016/031611, dated Jun. 20, 2016, 10 pages.
International Search Report and Written Opinion in International Application No. PCT/US2016/031603, dated Jun. 22, 2016, 11 pages.
International Search Report and Written Opinion in International Application No. PCT/US2015/035046, dated Aug. 27, 2015, 9 pages.
Canadian Examination Report in Canadian Application No. 2,766,100, dated Jan. 31, 2017, 3 pages.
International Search Report and Written Opinion in International Application No. PCT/US2016/019741, dated Aug. 2, 2016, 16 pages.
International Preliminary Report on Patentability in International Application No. PCT/US2015/035046, dated Dec. 22, 2016, 7 pages.

(56) References Cited

OTHER PUBLICATIONS

Malaysian Office Action in Malaysian Application No. PI 2011006255, dated Mar. 15, 2017, 2 pages.
European Search Report in European Application No. 16199883.6, dated Jun. 4, 2017, 7 pages.
Taiwan Office Action in Taiwan Application No. 105111882, dated Mar. 8, 2017, 5 pages (English Translation).
Vietnamese Office Action in Vietnamese Application No. 2012-00241, dated May 9, 2017, 3 pages (English Translation).
International Preliminary Report on Patentability in International Application No. PCT/US2016/019741, dated Aug. 29, 2017, 10 pages.
Vietnamese Office Action in Vietnamese Application No. 2017-03601, dated Nov. 27, 2017, 2 pages (English Translation).
International Preliminary Report on Patentability in International Application No. PCT/US2016/031606, dated Nov. 23, 2017, 7 pages.
International Preliminary Report on Patentability in International Application No. PCT/US2016/031611, dated Nov. 23, 2017, 7 pages.
International Preliminary Report on Patentability in International Application No. PCT/US2016/031603, dated Nov. 23, 2017, 7 pages.
Australian Office Action in Australian Application No. 2017206260, dated Mar. 20, 2018, 4 pages.
Peru Office Action in Peru Application No. 287.14, dated Dec. 14, 2017, 16 pages (English Translation).

\* cited by examiner

BICYCLIC HETEROARYLAMINOALKYL PHENYL DERIVATIVES AS PI3K INHIBITORS

This application claims the benefit of priority of Ser. No. 62/010,760, filed Jun. 11, 2014, which is incorporated herein by reference in its entirety.

TECHNICAL FIELD

This application relates to bicyclic heteroarylaminoalkyl phenyl derivatives, which are inhibitors of PI3K, and compositions and methods of treatment related thereto.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

The differential tissue distribution of the PI3K isoforms factors in their distinct biological functions. Genetic ablation of either PI3Kα or PI3Kβ results in embryonic lethality, indicating that PI3Kα and PI3Kβ have essential and non-redundant functions, at least during development (Vanhaesebroeck, et al., 2005). In contrast, mice which lack PI3Kγ and PI3Kδ are viable, fertile and have a normal life span although they show an altered immune system. PI3Kγ deficiency leads to impaired recruitment of macrophages and neutrophils to sites of inflammation as well as impaired T cell activation (Sasaki, et al., Science, 2000, 287(5455): 1040-6). PI3Kδ-mutant mice have specific defects in B cell signaling that lead to impaired B cell development and reduced antibody responses after antigen stimulation (Clayton, et al., J Exp Med. 2002, 196(6):753-63; Jou, et al., Mol Cell Biol. 2002, 22(24):8580-91; Okkenhaug, et al., Science, 2002, 297(5583):1031-4).

The phenotypes of the PI3Kγ and PI3Kδ-mutant mice suggest that these enzymes may play a role in inflammation and other immune-based diseases and this is borne out in preclinical models. PI3Kγ-mutant mice are largely protected from disease in mouse models of rheumatoid arthritis (RA) and asthma (Camps, et al., Nat Med. 2005, 11(9):936-43; Thomas, et al., Eur. J. Immunol. 2005, 35(4):1283-91). In addition, treatment of wild-type mice with a selective inhibitor of PI3Kγ was shown to reduce glomerulonephritis and prolong survival in the MRL-lpr model of systemic lupus nephritis (SLE) and to suppress joint inflammation and damage in models of RA (Barber, et al., Nat Med. 2005, 11(9):933-5; Camps, et al., 2005). Similarly, both PI3Kδ-mutant mice and wild-type mice treated with a selective inhibitor of PI3Kδ have been shown to have attenuated allergic airway inflammation and hyper-responsiveness in a mouse model of asthma (Ali, et al., Nature. 2004, 431(7011): 1007-11; Lee, et al., FASEB J. 2006, 20(3):455-65) and to have attenuated disease in a model of RA (Randis, et al., Eur. J. Immunol., 2008, 38(5):1215-24).

B cell proliferation has shown to play a major role in the development of inflammatory autoimmune diseases (Puri, Frontiers in Immunology (2012), 3(256), 1-16; Walsh, Kidney International (2007) 72, 676-682). For example, B cells support T-cell autoreactivity, an important component of inflammatory autoimmune diseases. Once activated and matured, B cells can traffic to sites of inflammation and recruit inflammatory cells or differentiate to plasmablasts. Thus, activity of B-cells can be affected by targeting B-cell stimulatory cytokines, B-cell surface receptors, or via B-cell depletion. Rituximaban—IgG1 κ mouse/human chimeric monoclonal antibody directed against the B-cell surface receptor CD20—has been shown to deplete CD20+ B cells. Use of rituximab has been shown to have efficacy in treating idiopathic thrombocytopenic purpura, autoimmune hemolytic anemia, or vasculitis. For example, treatment with rituximab resulted in remission of the disease in patients suffering from anti-neutrophil cytoplasm antibody associated (ANCA) systemic vasculitis (AASV) with demonstrated peripheral B-cell depletion (Walsh, 2007; Lovric, Nephrol Dial Transplant (2009) 24: 179-185). Similarly, a complete response was reported in one-third to two-thirds of patients having mixed cryoglobulinemia vasculitis after treatment with rituximab, including patients who presented with a severe form of vasculitis that was resistant or intolerant to other treatments (Cacoub, Ann Rheum Dis 2008; 67:283-287). Similarly, rituximab has been shown to have efficacy in treating patients with idiopathic thrombocytopenic purpura (or immune thrombocytopenic purpura) (Garvey, British Journal of Haematology, (2008) 141, 149-169; Godeau, Blood (2008), 112(4), 999-1004; Medeo, European Journal of Haematology, (2008) 81, 165-169) and autoimmune hemolytic anemia (Garvey, British Journal of Haematology, (2008) 141, 149-169).

PI3Kδ signaling has been tied to B cell survival, migration, and activation (Puri, *Frontiers in Immunology*, 2012, 3(256), 1-16, at pages 1-5; and Clayton, *J Exp Med*, 2002, 196(6):753-63). For example, PI3Kδ is required for antigen-dependent B-cell activation driven by B cell receptor. By blocking B-cell adhesion, survival, activation, and proliferation, PI3Kδ inhibition can impair the ability of B cells to activate T cells, preventing their activation and reducing secreation of autoantibodies and pro-inflammatory cytokines Hence, by their ability to inhibit B cell activation, PI3Kδ inhibitors would be expected to treat B cell mediated diseases that were treatable by similar methods such as B cell depletion by rituximab. Indeed, PI3Kδ inhibitors have been shown to be useful mouse models of various autoimmune diseases that are also treatable by rituximab such as arthritis (Puri (2012)). Further, innate-like B cells, which are linked to autoimmunity are sensitive to PI3Kδ activity, as MZ and B-1 cells are nearly absent in mice lacking the p110δ gene (Puri (2012). PI3Kδ inhibitors can reduce trafficking of and activation of MZ and B-1 cells, which are implicated in autoimmune diseases.

In addition to their potential role in inflammatory diseases, all four class I PI3K isoforms may play a role in cancer. The gene encoding p110α is mutated frequently in common cancers, including breast, prostate, colon and endometrial (Samuels, et al., Science, 2004, 304(5670):554; Samuels, et al., Curr Opin Oncol. 2006, 18(1):77-82). Eighty percent of these mutations are represented by one of three amino acid substitutions in the helical or kinase domains of the enzyme and lead to a significant upregulation of kinase activity resulting in oncogenic transformation in cell culture and in animal models (Kang, et al., Proc Natl Acad Sci USA. 2005, 102(3):802-7; Bader, et al., Proc Natl Acad Sci USA. 2006, 103(5):1475-9). No such mutations have been identified in the other PI3K isoforms although there is evidence that they can contribute to the development and progression of malignancies. Consistent overexpression of PI3Kδ is observed in acute myeloblastic leukemia (Sujobert, et al., Blood, 2005, 106(3):1063-6) and inhibitors of PI3Kδ can prevent the growth of leukemic cells (Billottet, et al., Oncogene. 2006, 25(50):6648-59). Elevated expression of PI3Kγ is seen in chronic myeloid leukemia (Hickey, et al., J Biol Chem. 2006, 281(5):2441-50). Alterations in expression of PI3Kβ, PI3Kγ and PI3Kδ have also been observed in cancers of the brain, colon and bladder (Benistant, et al., Oncogene, 2000, 19(44):5083-90; Mizoguchi, et al., Brain Pathol. 2004, 14(4):372-7; Knobbe, et al., Neuropathol Appl Neurobiol. 2005, 31(5):486-90). Further, these isoforms have all been shown to be oncogenic in cell culture (Kang, et al., 2006).

For these reasons, there is a need to develop new PI3K inhibitors that can be used inflammatory disorders, autoimmune diseases and cancer. This invention is directed to this need and others.

SUMMARY

The present application provides, inter alia, a compound of Formula I:

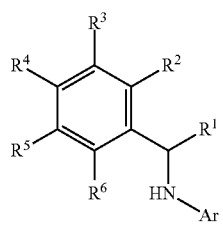

or a pharmaceutically acceptable salt thereof, wherein the variables are defined infra.

The present application further provides compositions comprising a compound of the invention, or a pharmaceutically acceptable salt thereof, and at least one pharmaceutically acceptable carrier.

The present application also provides methods of modulating an activity of a PI3K kinase, comprising contacting the kinase with a compound of the invention, or a pharmaceutically acceptable salt thereof.

The present application further provides methods of treating a disease in a patient, wherein said disease is associated with abnormal expression or activity of a PI3K kinase, comprising administering to said patient a therapeutically effective amount of a compound of the invention, or a pharmaceutically acceptable salt thereof.

The present application further provides methods of treating an immune-based disease in a patient, comprising administering to said patient a therapeutically effective amount of a compound of the invention, or a pharmaceutically acceptable salt thereof.

The present application also provides methods of treating a cancer in a patient, comprising administering to said patient a therapeutically effective amount of a compound of the invention, or a pharmaceutically acceptable salt thereof.

The present application further provides methods of treating a lung disease in a patient, comprising administering to said patient a therapeutically effective amount of a compound of the invention, or a pharmaceutically acceptable salt thereof.

The present application also provides a compound of the invention, or a pharmaceutically acceptable salt thereof, for use in any of the methods described herein.

The present application further provides use of a compound, or a pharmaceutically acceptable salt thereof, for the manufacture of a medicament for use in any of the methods described herein.

DETAILED DESCRIPTION

The present application provides, inter alia, a compound of Formula I:

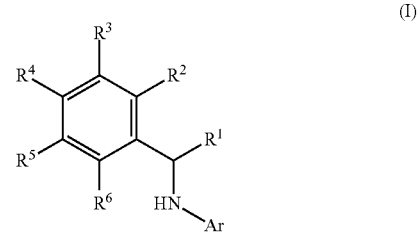

or a pharmaceutically acceptable salt thereof, wherein:

Ar is

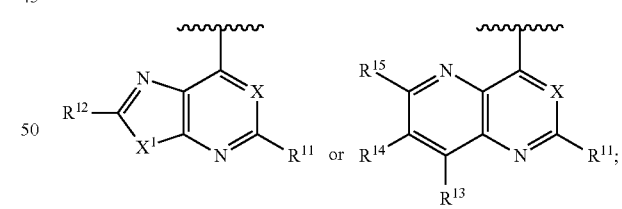

X is N or $CR^{10}$;
$X^1$ is O or S;
$R^1$ is $C_{1-3}$ alkyl;
$R^2$ is halo, $C_{1-6}$ alkyl, $C_{1-6}$ alkoxy, $C_{1-6}$ haloalkyl, $C_{1-6}$ haloalkoxy, phenyl, or 5-6 membered heteroaryl; wherein said phenyl and 5-6 membered heteroaryl are each optionally substituted by 1, 2, 3, or 4 substituents independently selected from halo, OH, CN, $C_{1-4}$ alkyl, $C_{1-4}$ alkoxy, and $C_{1-4}$ haloalkoxy;
$R^3$ is Cy, —($C_{1-3}$ alkylene)-Cy, $C_{1-6}$ alkyl, $C_{2-6}$ alkenyl, $C_{2-6}$ alkynyl, $C_{1-6}$ haloalkyl, C(=O)$R^b$, C(=O)$NR^cR^d$, C(=O)$OR^a$, $NR^cR^d$, $NR^cC$(=O)$R^a$, $NR^cC$(=O)$OR^b$, $NR^cC$(=O)$NR^cR^d$, $NR^cS$(=O)$_2R^b$, or $NR^cS$(=O)$_2NR^cR^d$;

wherein said $C_{1-6}$ alkyl, $C_{2-6}$ alkenyl, and $C_{2-6}$ alkynyl are each optionally substituted by 1, 2, or 3 independently selected $R^{3a}$ groups;

provided that either (i) $R^2$ is phenyl or 5-6 membered heteroaryl, wherein said phenyl and 5-6 membered heteroaryl are each optionally substituted by 1, 2, 3, or 4 substituents independently selected from halo, OH, CN, $C_{1-4}$ alkyl, $C_{1-4}$ alkoxy, and $C_{1-4}$ haloalkoxy; or (ii) $R^3$ is Cy or —($C_{1-3}$ alkylene)-Cy;

$R^4$ is H, halo, OH, CN, $C_{1-4}$ alkyl, $C_{1-4}$ haloalkyl, $C_{1-4}$ alkoxy, or $C_{1-4}$ haloalkoxy;

$R^5$ is halo, OH, CN, $C_{1-4}$ alkyl, $C_{1-4}$ haloalkyl, $C_{1-4}$ alkoxy, $C_{1-4}$ haloalkoxy, or cyclopropyl;

$R^6$ is H, halo, CN, or $C_{1-4}$ alkyl;

each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cyclo alkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, amino sulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^{10}$, $R^{13}$, and $R^{14}$ is independently hydrogen, OH, $NO_2$, CN, halo, oxo, $C_{1-4}$ alkyl, $C_{2-4}$ alkenyl, $C_{2-4}$ alkynyl, $C_{1-4}$ haloalkyl, cyano-$C_{1-4}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, di($C_{1-3}$ alkyl)aminocarbonylamino, $C_{3-7}$ cycloalkyl, 4-7 membered heterocycloalkyl, phenyl, phenyl-$C_{1-3}$-alkyl, 5-6 membered heteroaryl, 5-6 membered heteroaryl-$C_{1-3}$-alkyl, and 4-7 membered heterocycloalkyloxy; and each $R^{11}$, $R^{12}$, and $R^{15}$ is independently hydrogen, $C_{1-4}$ alkyl, $C_{2-4}$ alkenyl, $C_{2-4}$ alkynyl, $C_{1-4}$ haloalkyl, cyano-$C_{1-4}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, alkylsulfonylamino, aminosulfonyl, $C_{1-3}$ alkylaminosulfonyl, di($C_{1-3}$ alkyl)amino sulfonyl, amino sulfonylamino, $C_{1-3}$ alkylaminosulfonylamino, di($C_{1-3}$ alkyl)aminosulfonylamino, amino carbonylamino, $C_{1-3}$ alkylaminocarbonylamino, di($C_{1-3}$ alkyl)aminocarbonylamino, $C_{3-7}$ cycloalkyl, 4-7 membered heterocycloalkyl, phenyl, aryl-$C_{1-3}$-alkyl, 5-6 membered heteroaryl, 5-6 membered heteroaryl-$C_{1-3}$-alkyl, and 4-7 membered heterocycloalkyloxy;

each $R^a$ $R^c$, and $R^d$ is independently selected from H, $C_{1-6}$ alkyl, $C_{1-6}$ haloalkyl, $C_2$-6 alkenyl, $C_{2-6}$ alkynyl, and Cy; wherein said $C_{1-6}$ alkyl, $C_{2-6}$ alkenyl, and $C_{2-6}$ alkynyl are each optionally substituted with 1, 2, or 3 independently selected $R^{3b}$ groups; each $R^b$ is independently selected from $C_{1-6}$ alkyl, $C_{1-6}$ haloalkyl, $C_{2-6}$ alkenyl, $C_{2-6}$ alkynyl, and Cy; wherein said $C_{1-6}$ alkyl, $C_{2-6}$ alkenyl, and $C_{2-6}$ alkynyl are each optionally substituted with 1, 2, or 3 independently selected $R^{3b}$ groups;

or $R^c$ and $R^d$ together with the N atom to which they are attached form a 4-, 5-, 6-, or 7 membered heterocycloalkyl group, which is optionally substituted with —OH or $C_{1-3}$ alkyl;

each Cy is independently selected from $C_{3-7}$ cycloalkyl, 4-6 membered heterocycloalkyl, phenyl, naphthyl, and 5-6 membered heteroaryl, each of which is optionally substituted with 1, 2, or 3 independently selected $R^{3b}$ groups;

each $R^{3a}$ is independently selected from halo, CN, $NO_2$, $C_{1-6}$ alkyl, $C_{2-6}$ alkenyl, $C_{2-6}$ alkynyl, $C_{1-6}$ haloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{a1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^{c1}C(=NR^e)NR^{c1}R^{d1}$, $NR^{c1}S(=O)R^{b1}$, $NR^{c1}S(=O)_2NR^{c1}R^{d1}$, $S(=O)_2R^{b1}$, and $S(=O)_2NR^{c1}R^{d1}$; wherein said $C_{1-6}$ alkyl, $C_{2-6}$ alkenyl, and $C_{2-6}$ alkynyl are each optionally substituted with 1, 2, or 3 independently selected $R^8$ groups;

each $R^{3b}$, is independently selected from $Cy^1$, —($C_{1-3}$ alkylene)-$Cy^1$, halo, CN, $NO_2$, $C_{1-6}$ alkyl, $C_{2-6}$ alkenyl, $C_{2-6}$ alkynyl, $C_{1-6}$ haloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{a1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^{c1}$ $S(=O)R^{b1}$, $NR^{c1}$ $S(=O)_2NR^{c1}R^{d1}$, $S(=O)R^{b1}$, $S(=O)_2R^{b1}$, and $S(=O)_2NR^{c1}R^{d1}$; wherein said $C_{1-6}$ alkyl, $C_{2-6}$ alkenyl, and $C_{2-6}$ alkynyl are each optionally substituted with 1, 2, or 3 independently selected $R^8$ groups;

each $Cy^1$ is independently selected from $C_{3-7}$ cycloalkyl, 4-7 membered heterocycloalkyl, phenyl, and 5-6 membered heteroaryl, each of which is optionally substituted with 1, 2, 3, or 4 independently selected $R^8$ groups;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^8$ groups; and each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^8$ groups;

or $R^{c1}$ and $R^{d1}$ together with the N atom to which they are attached form a 4-, 5-, 6-, or 7 membered heterocycloalkyl group, which is optionally substituted with —OH or $C_{1-3}$ alkyl.

In some embodiments, $R^6$ is H.

In some embodiments, $R^1$ is methyl.

In some embodiments, $R^2$ is $C_{1-6}$ alkoxy or phenyl; wherein said phenyl is optionally substituted by 1, 2, 3, or 4 substituents independently selected from halo, OH, CN, $C_{1-4}$ alkyl, $C_{1-4}$ alkoxy, and $C_{1-4}$ haloalkoxy.

In some embodiments, $R^2$ is $C_{1-4}$ alkoxy.

In some embodiments, $R^2$ is methoxy or ethoxy.

In some embodiments, $R^2$ is phenyl; wherein said phenyl is optionally substituted by 1, 2, 3, or 4 independently selected halo groups.

In some embodiments, wherein $R^2$ is 3,5-difluorophenyl.

In some embodiments, $R^3$ is Cy, $C(=O)R^b$, $C(=O)NR^cR^d$, or $C(=O)OR^a$.

In some embodiments, $R^3$ is Cy or $C(=O)NR^cR^d$.

In some embodiments, $R^3$ is Cy.

In some embodiments, $R^3$ is $C(=O)NR^cR^d$.

In some embodiments, R³ is a 4-6 membered heterocycloalkyl or 5-6 membered heteroaryl, each of which is optionally substituted by 1 or 2 independently selected R³ᵇ groups.

In some embodiments, R³ is:

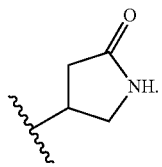 [SMILES: *C1CNC(=O)C1]

In some embodiments, R³ is pyridine optionally substituted by 1 or 2 independently selected R³ᵇ groups.

In some embodiments, R³ is:

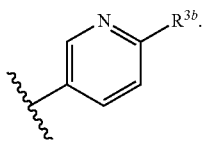

In some embodiments, R³ is C(=O)NH(CH₂CH₃).

In some embodiments, each R³ᵇ is independently selected from halo, CN, NO₂, $C_{1-6}$ alkyl, $C_{1-6}$ haloalkyl, OR^{a1}, C(=O)R^{b1}, C(=O)NR^{c1}R^{d1}, C(=O)OR^{a1}, NR^{c1}R^{d1}, S(=O)₂R^{b1}, and S(=O)₂NR^{c1}R^{d1}; wherein said $C_{1-6}$ alkyl is optionally substituted with 1, 2, or 3 independently selected R⁸ groups.

In some embodiments, each R³ᵇ is independently selected from halo, CN, $C_{1-6}$ alkyl, $C_{1-6}$ haloalkyl, hydroxy, $C_{1-6}$ alkoxy, $C_{1-6}$ haloalkoxy, amino, $C_{1-6}$ alkylamino, di($C_{1-6}$ alkyl)amino, $C_{1-6}$ alkylsulfonyl, carbamyl, $C_{1-6}$ alkylcarbamyl, and di($C_{1-6}$ alkyl)carbamyl.

In some embodiments, each R³ᵇ is $C_{1-6}$ alkylamino.
In some embodiments, each R³ᵇ is di($C_{1-6}$ alkyl)carbamyl.
In some embodiments, each R³ᵇ is —C(=O)N(CH₃)₂.
In some embodiments, R⁴ is $C_{1-4}$ alkyl, halo, or cyano.
In some embodiments, R⁴ is $C_{1-4}$ alkyl.
In some embodiments, R⁴ is methyl or fluoro.
In some embodiments, R⁴ is methyl.
In some embodiments, R⁴ is halo.
In some embodiments, R⁴ is fluoro.
In some embodiments, R⁵ is halo, CN, or methyl.
In some embodiments, R⁵ is halo.
In some embodiments, R⁵ is chloro.
In some embodiments, Ar is:

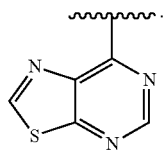 [SMILES: *c1ncnc2scnc12]

In some embodiments, Ar is:

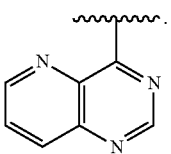 [SMILES: *c1ncnc2cccnc12]

In some embodiments:
Ar is:

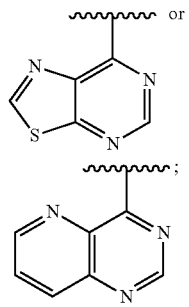

R¹ is methyl;
R² is $C_{1-6}$ alkoxy, $C_{1-6}$ haloalkoxy, or phenyl; wherein said phenyl is optionally substituted by 1, 2, or 3 substituents independently selected from halo, OH, CN, $C_{1-4}$ alkyl, $C_{1-4}$ alkoxy, and $C_{1-4}$ haloalkoxy;
R³ is Cy or C(=O)NR^cR^d;
provided that either (i) R² is phenyl, wherein said phenyl is optionally substituted by 1, 2, or 3 substituents independently selected from halo, OH, CN, $C_{1-4}$ alkyl, $C_{1-4}$ alkoxy, and $C_{1-4}$ haloalkoxy; or (ii) R³ is Cy;
R⁴ is halo, $C_{1-4}$ alkyl, or $C_{1-4}$ haloalkyl;
R⁵ is halo, CN, $C_{1-4}$ alkyl, or $C_{1-4}$ haloalkyl;
R⁶ is H;
each Cy is independently selected from 4-6 membered heterocycloalkyl or 5-6 membered heteroaryl, each of which is optionally substituted with 1 or 2 independently selected R³ᵇ groups;
each R^c and R^d is independently selected from H and $C_{1-6}$ alkyl; and
each R³ᵇ is independently selected from halo, CN, $C_{1-6}$ alkyl, $C_{1-6}$ haloalkyl, hydroxy, $C_{1-6}$ alkoxy, $C_{1-6}$ haloalkoxy, amino, $C_{1-6}$ alkylamino, di($C_{1-6}$ alkyl)amino, $C_{1-6}$ alkylsulfonyl, carbamyl, $C_{1-6}$ alkylcarbamyl, and di($C_{1-6}$ alkyl)carbamyl.

In some embodiments:
Ar is:

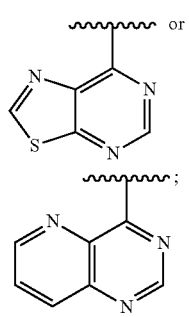

R² is $C_{1-6}$ alkoxy or phenyl, wherein said phenyl is optionally substituted by 1, 2, 3, or 4 independently selected halo groups;
R³ is C(=O)NR^cR^d, 4-6 membered heterocycloalkyl, or 5-6 membered heteroaryl; wherein said 4-6 membered heterocycloalkyl and 5-6 membered heteroaryl is optionally substituted by 1, 2, or 3 independently selected R³ᵇ groups;
each R³ᵇ is independently selected from halo, CN, $C_{1-6}$ alkyl, $C_{1-6}$ haloalkyl, hydroxy, $C_{1-6}$ alkoxy, $C_{1-6}$ haloalkoxy, amino, $C_{1-6}$ alkylamino, di($C_{1-6}$ alkyl)amino, $C_{1-6}$ alkylsulfonyl, carbamyl, $C_{1-6}$ alkylcarbamyl, and di($C_{1-6}$ alkyl)carbamyl;

$R^4$ is $C_{1-4}$ alkyl or halo;

$R^5$ is halo; and $R^6$ is H.

In some embodiments:

Ar is:

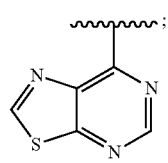 [SMILES: *c1ncnc2scnc12]

$R^2$ is $C_{1-6}$ alkoxy;

$R^3$ is 4-6 membered heterocycloalkyl;

$R^4$ and $R^5$ are each independently halo; and $R^6$ is H.

In some embodiments:

Ar is:

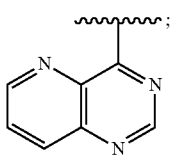 [SMILES: *c1ncnc2cccnc12]

$R^2$ is $C_{1-6}$ alkoxy or phenyl, wherein said phenyl is optionally substituted by 1, 2, 3, or 4 independently selected halo groups;

$R^3$ is C(=O)$NR^cR^d$, 4-6 membered heterocycloalkyl, or 5-6 membered heteroaryl; wherein said 4-6 membered heterocycloalkyl and 5-6 membered heteroaryl is optionally substituted by 1, 2, or 3 independently selected $R^{3b}$ groups;

each $R^{3b}$ is di($C_{1-6}$ alkyl)carbamyl;

$R^4$ is halo or $C_{1-4}$ alkyl;

$R^5$ is halo; and $R^6$ is H.

In some embodiments, the compound is a compound having Formula (II):

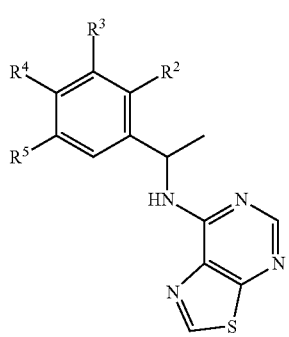

or a pharmaceutically acceptable salt thereof.

In some embodiments, the compound is a compound having Formula (III):

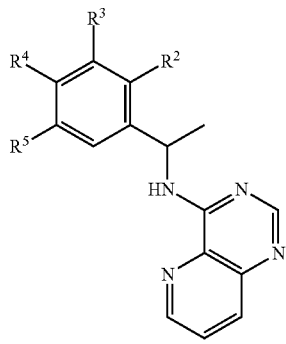

or a pharmaceutically acceptable salt thereof.

In some embodiments, the compound is a compound having Formula (IIa):

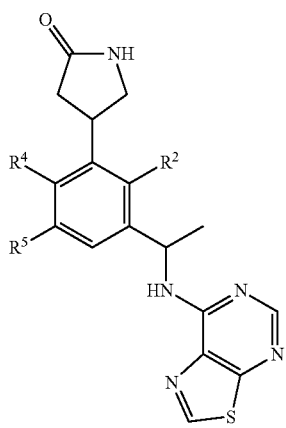

or a pharmaceutically acceptable salt thereof.

In some embodiments, the compound is a compound having Formula (IIIa):

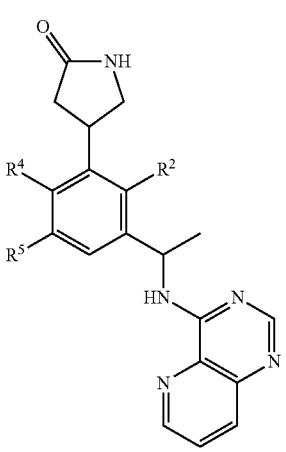

or a pharmaceutically acceptable salt thereof.

In some embodiments, $R^{11}$ is H.
In some embodiments, $R^{12}$ is H.
In some embodiments, $R^{11}$ and $R^{12}$ are each H.
In some embodiments, $R^{13}$ is H.
In some embodiments, $R^{14}$ is H.
In some embodiments, $R^{15}$ is H.
In some embodiments, $R^{11}$, $R^{13}$, $R^{14}$ and $R^{15}$ are each H.

In some embodiments, the compound is a compound selected from:

4-{3-chloro-6-ethoxy-2-fluoro-5-[1-([1,3]thiazolo[5,4-d]pyrimidin-7-ylamino)ethyl]phenyl}pyrrolidin-2-one;

4-{3-chloro-6-ethoxy-2-fluoro-5-[1-(pyrido[3,2-d]pyrimidin-4-ylamino)ethyl]phenyl}pyrrolidin-2-one;

5-{3-chloro-6-methoxy-2-methyl-5-[(1S)-1-(pyrido[3,2-d]pyrimidin-4-ylamino)ethyl]phenyl}-N,N-dimethylpyridine-2-carboxamide;

4-chloro-N-ethyl-3',5'-difluoro-3-methyl-6-[1-(pyrido[3,2-d]pyrimidin-4-ylamino)ethyl]biphenyl-2-carboxamide;

or a pharmaceutically acceptable salt thereof.

In some embodiments, the compound is (S)-4-(3-chloro-6-ethoxy-2-fluoro-5-((S)-1-(thiazolo[5,4-d]pyrimidin-7-ylamino)ethyl)phenyl)pyrrolidin-2-one; or a pharmaceutically acceptable salt thereof.

In some embodiments, the compound is (R)-4-(3-chloro-6-ethoxy-2-fluoro-5-((R)-1-(thiazolo[5,4-d]pyrimidin-7-ylamino)ethyl)phenyl)pyrrolidin-2-one; or a pharmaceutically acceptable salt thereof.

In some embodiments, the compound is (S)-4-(3-chloro-6-ethoxy-2-fluoro-5-((R)-1-(thiazolo[5,4-d]pyrimidin-7-ylamino)ethyl)phenyl)pyrrolidin-2-one; or a pharmaceutically acceptable salt thereof.

In some embodiments, the compound is (R)-4-(3-chloro-6-ethoxy-2-fluoro-5-((S)-1-(thiazolo[5,4-d]pyrimidin-7-ylamino)ethyl)phenyl)pyrrolidin-2-one; or a pharmaceutically acceptable salt thereof.

In some embodiments, the compound is (S)-4-(3-chloro-6-ethoxy-2-fluoro-5-((S)-1-(pyrido[3,2-d]pyrimidin-4-ylamino)ethyl)phenyl)pyrrolidin-2-one; or a pharmaceutically acceptable salt thereof.

In some embodiments, the compound is (R)-4-(3-chloro-6-ethoxy-2-fluoro-5-((R)-1-(pyrido[3,2-d]pyrimidin-4-ylamino)ethyl)phenyl)pyrrolidin-2-one; or a pharmaceutically acceptable salt thereof.

In some embodiments, the compound is (S)-4-(3-chloro-6-ethoxy-2-fluoro-5-((R)-1-(pyrido[3,2-d]pyrimidin-4-ylamino)ethyl)phenyl)pyrrolidin-2-one; or a pharmaceutically acceptable salt thereof.

In some embodiments, the compound is (R)-4-(3-chloro-6-ethoxy-2-fluoro-5-((S)-1-(pyrido[3,2-d]pyrimidin-4-ylamino)ethyl)phenyl)pyrrolidin-2-one; or a pharmaceutically acceptable salt thereof.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like.

As used herein, "$C_{n-m}$ alkenyl" refers to an alkyl group having one or more double carbon-carbon bonds and having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "alkylene", employed alone or in combination with other terms, refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), t-butoxy, and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "carbamyl" to a group of formula —C(O)NH$_2$.

As used herein, the term "carbonyl", employed alone or in combination with other terms, refers to a —C(=O)— group. Also may be written as C(O).

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, the term "$C_{1-3}$ alkoxy-$C_{1-3}$ alkyl" refers to a group of formula —($C_{1-3}$ alkylene)-O($C_{1-3}$ alkyl).

As used herein, the term "$C_{1-4}$ alkoxy-$C_{1-4}$ alkyl" refers to a group of formula —($C_{1-4}$ alkylene)-O($C_{1-4}$ alkyl).

As used herein, the term "$C_{1-4}$ haloalkoxy-$C_{1-4}$ alkyl" refers to a group of formula —($C_{1-4}$ alkylene)-O($C_{1-4}$ haloalkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, the halo group is F or Cl.

As used herein, "$C_{n-m}$ haloalkoxy" refers to a group of formula O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, or 7 ring-forming carbons ($C_{3-7}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, or cyclohexyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring.

A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from 0, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

As used herein, the term "phenyl-C$_{n-m}$-alkyl", employed alone or in combination with other terms, refers to a group of formula -alkylene-phenyl, wherein the alkylene portion has n to m carbon atoms. In some embodiments, the alkylene portion has 1 to 3, 1 to 2, or 1 carbon atom(s). In some embodiments, the alkylene portion is methylene. In some embodiments, the arylalkyl group is benzyl.

As used herein, the term "C$_{n-m}$ heteroaryl-C$_{o-p}$-alkyl", employed alone or in combination with other terms, refers to a group of formula -alkylene-heteroaryl, wherein the heteroaryl portion has n to m ring member carbon atoms and the alkylene portion has o to p carbon atoms. In some embodiments, the alkylene portion has 1 to 3, 1 to 2, or 1 carbon atom(s). In some embodiments, the alkylene portion is methylene.

As used herein, the term "heterocycloalkyloxy" refers to a group of formula —O-(heterocycloalkyl).

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present application that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present application. Cis and trans geometric isomers of the compounds of the present application are described and may be isolated as a mixture of isomers or as separated isomeric forms.

In some embodiments, the compound has the (R)-configuration (e.g., at the carbon to which R$^1$ is attached). In some embodiments, the compound has the (S)-configuration (e.g., at the carbon to which R$^1$ is attached).

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

Compounds described herein, including salts thereof, can be prepared using known organic synthesis techniques and can be synthesized according to any of numerous possible synthetic routes. In some embodiments, the compounds can be prepared as described in U.S. patent application Ser. No. 13/601,349, filed Aug. 31, 2012, which is incorporated herein by reference in its entirety.

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

For example, compounds of Formula I can be formed as shown in Scheme I.

Compound (i) can be halogenated with N-chlorosuccinamide, N-bromosuccinamide or N-iodosuccinamide to give compound (ii) where X=Cl, Br, or I. The halo group of (ii) can be coupled to $R^3$-M, where M is a boronic acid, boronic ester or an appropriately substituted metal (e.g., $R^3$-M is $R^3$—$B(OH)_2$ or $R^3$—$Sn(Bu)_4$), under standard Suzuki conditions or standard Stille conditions (e.g., in the presence of a palladium(0) catalyst, such as tetrakis(triphenylphosphine) palladium(0) and a base (e.g., a bicarbonate or carbonate base) to give a derivative of formula (iii). Alternatively, $R^3$-M can be a cyclic amine (where M is H and attached to the amine nitrogen) with coupling to compound (ii) being performed by heating in base or under Buchwald conditions (e.g., in the presence of a palladium(0) catalyst, such as tetrakis(triphenylphosphine)palladium(0) and a base (e.g., an alkoxide base)) to afford ketone (iii). Reductive amination of ketone (iii) can furnish the amine intermediate (v). Alternatively, ketone (iii) can be reduced to give an alcohol which can be converted to the mesylate and reacted with sodium azide to give an azide derivative (iv). The azide of compound (iv) can be converted to an amine (v) under appropriate reducing conditions, such as trimethylphosphine or TMSI. Finally the secondary amine can be reacted with a heteroaryl halide compound (e.g., Ar—X, such as 7-chloro[1,3]thiazolo[5,4-d]pyrimidine or 4-chloropyrido[3,2-d]pyrimidine) to give a compound of Formula I (vi).

(e.g., TFA when P=Boc) and the resulting amine can be reacted with a heteroaryl halide compound (e.g., Ar—X) to give compound (vi). Finally, the halo group of (vi) can be coupled to $R^3$-M, where M is a boronic acid, boronic ester or an appropriately substituted metal (e.g., $R^3$-M is $R^3$—B(OH)$_2$ or $R^3$—Sn(Bu)$_4$), under standard Suzuki conditions or standard Stille conditions (e.g., in the presence of a palladium(0) catalyst, such as tetrakis(triphenylphosphine)-palladium(0) and a base (e.g., a bicarbonate or carbonate base)) to give a derivative of Formula I (vii). Alternatively, $R^3$-M can be a cyclic amine (where M is H and attached to the amine nitrogen) with coupling to compound (vi) being performed by heating in base or under Buchwald conditions (e.g., in the presence of a palladium(0) catalyst, such as

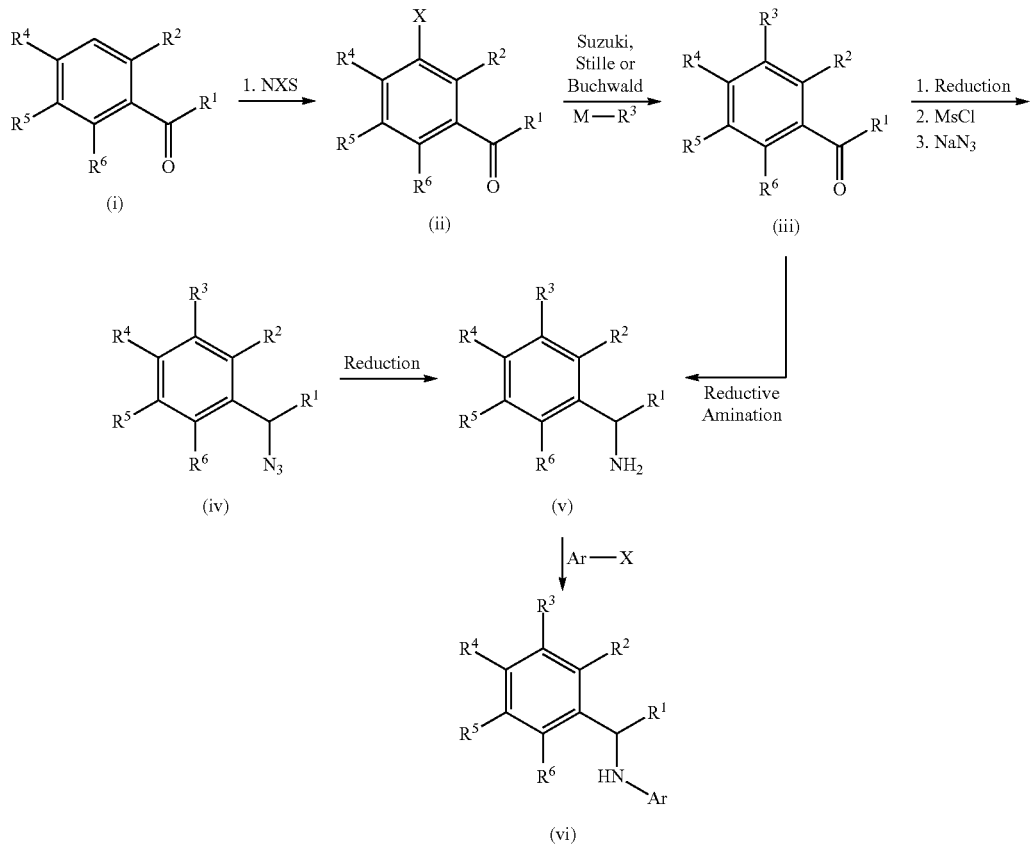

Scheme I

Alternatively, compounds of Formula I can also be formed as shown in Scheme II. Ketone (i) can be halogenated with N-chlorosuccinamide, N-bromosuccinamide or N-iodosuccinamide to give compound (ii) where X=Cl, Br, or I. Ketone (ii) can be reduced to give an alcohol (iii) which can be converted to the mesylate and reacted with sodium azide to give an azide derivative (iv). The azide of compound (iv) can be converted to an amine (v) under appropriate reducing conditions, such as trimethylphosphine or TMSI. The amine (v) can be protected with a suitable protecting group (e.g., by reacting with Boc$_2$O) and purified by chiral chromatography to afford a single enantiomer of amine compound (v). The amino group can be deprotected tetrakis(triphenylphosphine)-palladium(0) and a base (e.g., an alkoxide base)) to afford compounds of Formula I (vii).

Scheme II

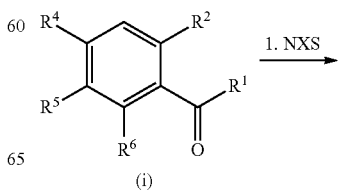

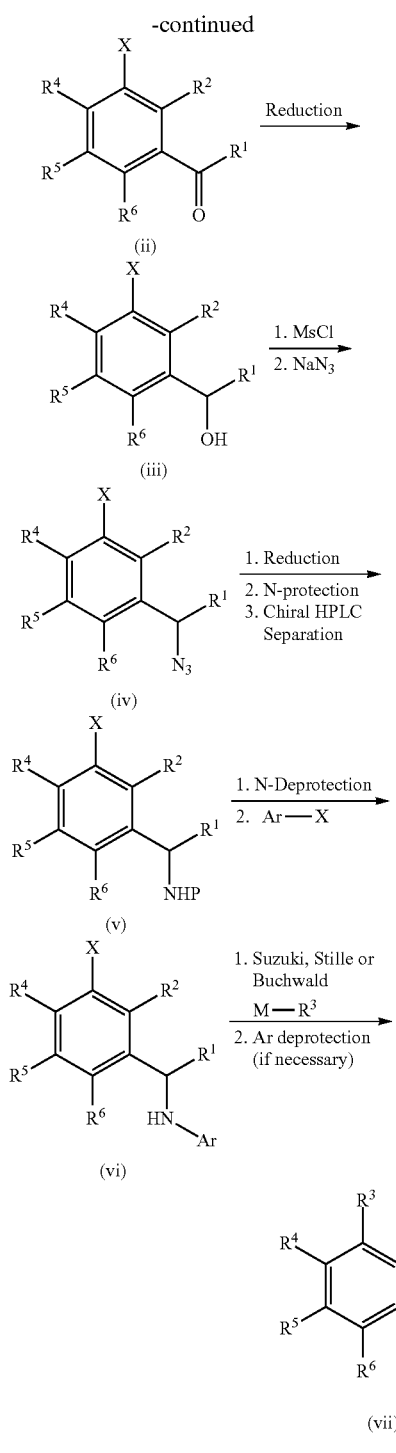

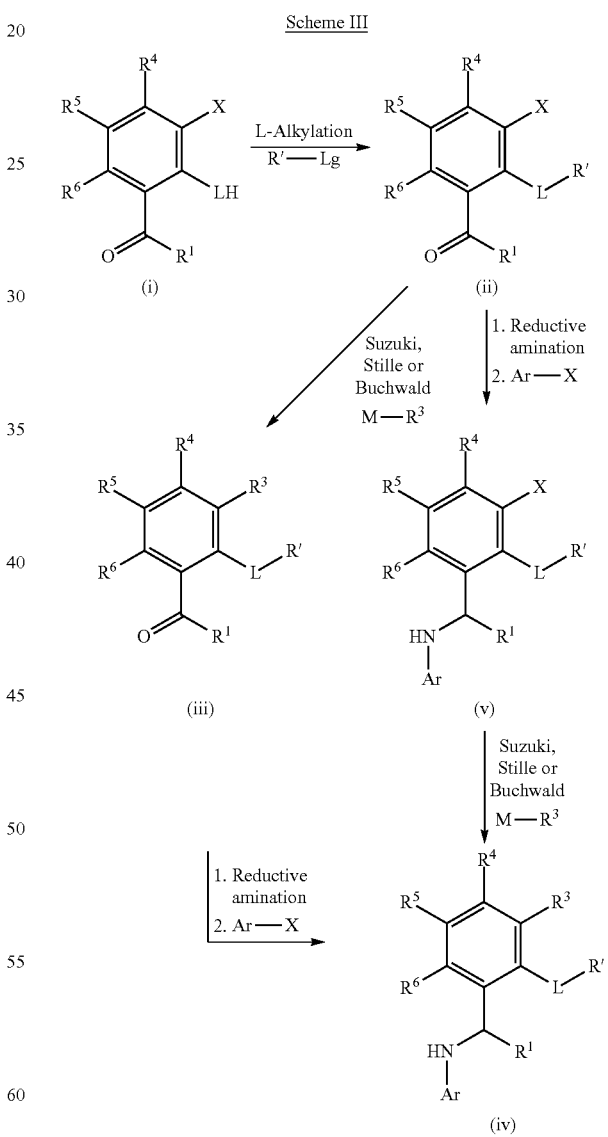

or carbonate base)) to give a derivative of formula (iii). Alternatively, $R^3$-M can be a cyclic amine (where M is H and attached to the amine nitrogen) with coupling to compound (ii) being performed by heating in base or under Buchwald conditions (e.g., in the presence of a palladium(0) catalyst, such as tetrakis(triphenylphosphine)-palladium(0) and a base (e.g., an alkoxide base)) to afford compounds of formula (iii). The ketone (iii) can be transformed using similar methods as shown in Schemes I and II to afford compounds of Formula I (iv). Alternatively, the halo-ketone (ii) can be transformed using similar methods as shown in Schemes I and II to afford halo intermediate (v). Suzuki, Stille, or Buchwald coupling of $R^3$-M with halo intermediate (v) by similar methods described in Schemes I and II can afford compounds of Formula I (iv).

Compounds of Formula I wherein L is O can be formed as shown in Scheme III. The phenols (i) can be alkylated using Mitsunobu conditions (e.g., WOH, DEAD, $Ph_3P$) or standard alkylating conditions (R'-Lg, Lg=leaving group) to afford ether derivatives (ii). The halo group (e.g., X=Br, I) of (ii) can be coupled to $R^3$-M, where M is a boronic acid, boronic ester, or an appropriately substituted metal (e.g., $R^3$-M is $R^3$—$B(OH)_2$ or $R^3$—$Sn(Bu)_4$), under standard Suzuki conditions or standard Stille conditions (e.g., in the presence of a palladium(0) catalyst, such as tetrakis(triphenylphosphine)-palladium(0) and a base (e.g., a bicarbonate Compounds of Formula I can be formed as shown in Scheme IV. Compound (i) can be acylated with a suitable acylating reagent (e.g., $R^1$—COCl) to form an ester which can be rearranged under Lewis acid conditions (e.g., $BF_3$/

HOAc complex) to afford ketone (ii). Halogenation of ketone (ii) using NXS (e.g., NXS=N-chlorosuccinamide, N-bromosuccinamide or N-iodosuccinamide) can give compound (iii) where X=Cl, Br, or I. The phenol can be converted to the triflate (iv) using standard conditions (e.g., Tf$_2$O). The triflate group of (iv) can be coupled to R$^2$-M, where M is a boronic acid, boronic ester or an appropriately substituted metal (e.g., R$^2$-M is R$^2$—B(OH)$_2$ or R$^2$—Sn(Bu)$_4$), under standard Suzuki conditions or standard Stille conditions (e.g., in the presence of a palladium(0) catalyst, such as tetrakis(triphenylphosphine)palladium(0) and a base (e.g., a bicarbonate or carbonate base)) to give ketone (v). Alternatively, R$^2$-M can be a cyclic amine (where M is H and attached to the amine nitrogen) with coupling to compound (iv) being performed by heating in base or under Buchwald conditions (e.g., in the presence of a palladium(0) catalyst, such as tetrakis(triphenylphosphine)palladium(0) and a base (e.g., an alkoxide base)) to afford ketone (v). The halo group of (v) can be coupled to R$^3$-M, where M is a boronic acid, boronic ester or an appropriately substituted metal (e.g., R$^3$-M is R$^3$—B(OH)$_2$ or R$^3$—Sn(Bu)$_4$), under standard Suzuki conditions or standard Stille conditions (e.g., in the presence of a palladium(0) catalyst, such as tetrakis(triphenylphosphine)palladium(0) and a base (e.g., a bicarbonate or carbonate base)) to give a derivative of formula (vi). Alternatively, R$^3$-M can be a cyclic amine (where M is H and attached to the amine nitrogen) with coupling to compound (v) being performed by heating in base or under Buchwald conditions (e.g., in the presence of a palladium(0) catalyst, such as tetrakis(triphenylphosphine) palladium(0) and a base (e.g., an alkoxide base)) to afford ketone (vi). Ketone (vi) can be transformed using similar methods as shown in Schemes I and II to afford compounds of Formula I (vii).

Alternatively, the halo-ketone (v) can be transformed using similar methods as shown in Schemes I and II to afford halo intermediate (viii). Suzuki, Stille, or Buchwald coupling of M-R$^3$ with compound (viii) by similar methods described in Schemes I and II can also afford compounds of Formula I (vii).

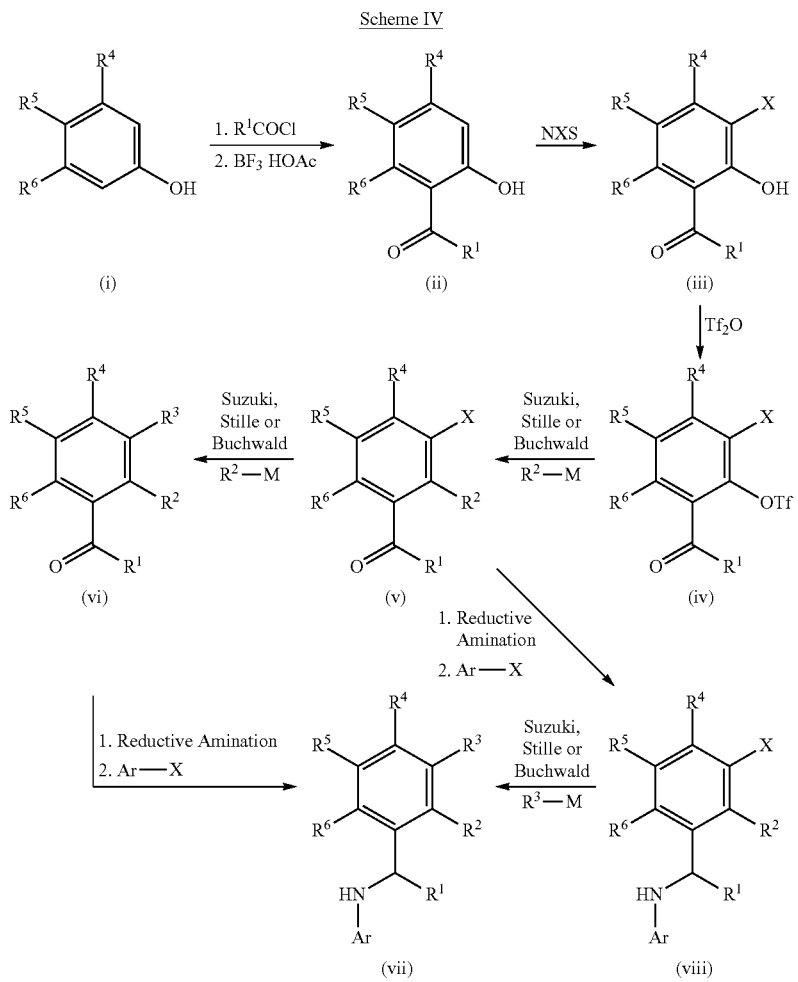

Scheme IV

Ketones which can be used in the processes of Schemes I-III can be formed as shown in Scheme V. The carboxylic acid (i) can be activated with a coupling agent (e.g., HBTU, HATU or EDC) and then reacted with N, O-dimethylhydroxylamine to give a N-methoxy-N-methylcarboxamide derivative (ii). Amide (ii) may then be reacted with a Grignard reagent of formula $R^1$—MgX (X=halo) to give ketone (iii). Ketone (iii) can be transformed using similar methods as shown in Schemes I, II and III to afford compounds of Formula I.

Scheme V

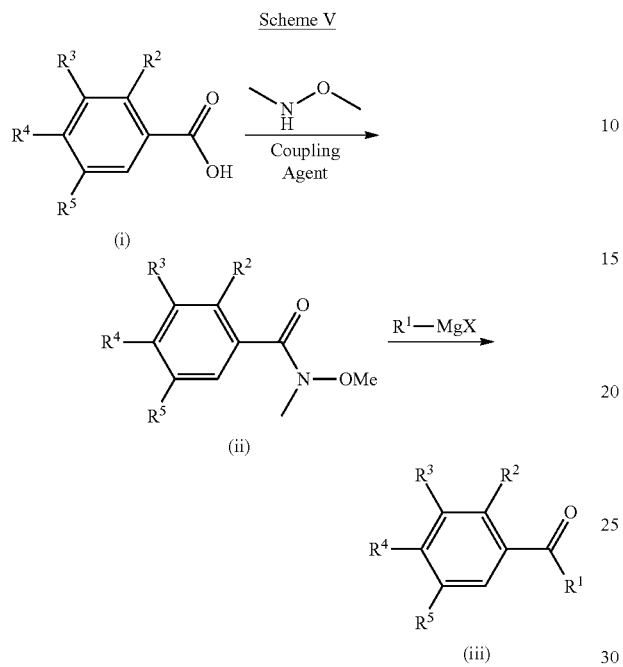

Compounds which can be used in the processes of Schemes I-III can also be formed as shown in Scheme VI. The halo-ketone (i) can be converted to the cyano-ketone (ii) using standard cyanation conditions (e.g., Pd(0) and Zn(CN)$_2$). Hydrolysis of the cyano group of (ii) under acidic or basic conditions can give the carboxylic acid which can be coupled to amines using a coupling agent (e.g., HATU, HBTU, EDC) and appropriate amines (HNR$^c$R$^d$) to give amide (iii) ($R^c$ and $R^d$ are various optionally substituted cyclic groups and non-cyclic groups, or $R^c$ and $R^d$, along with the nitrogen atom to which they are attached can cyclize to form a heterocycloalkyl group). The ketone of amide (iii) can be transformed using similar methods as shown in Schemes I, II and III to afford compounds of Formula I (v).

Scheme VI

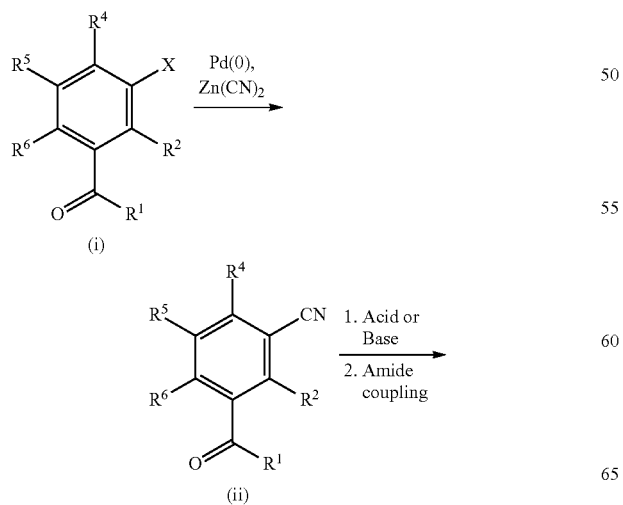

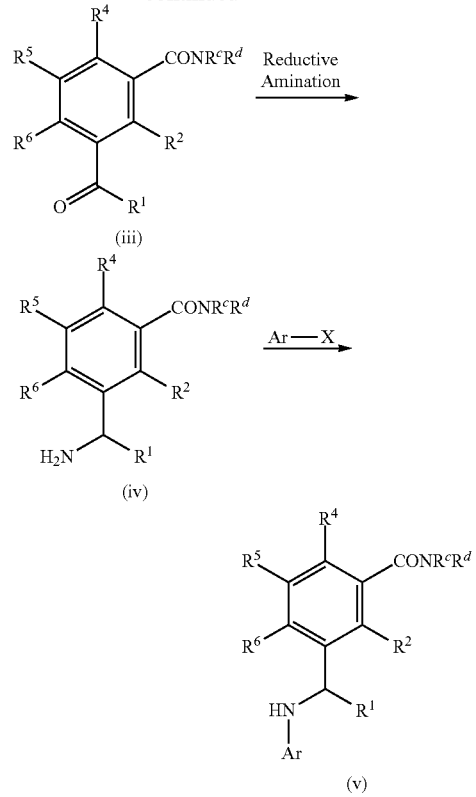

Additional compounds which can be used in the processes of Schemes I-III can be formed as shown in Scheme VII. Ketone (i) can be converted to the nitro-ketone (ii) using standard nitration conditions (e.g., HNO$_3$). Reduction of the nitro group of (ii) under standard conditions (e.g., Fe, Zn, or H$_2$ over Pd/C) can give the amino compound which can be derivatized, including acylated with appropriate acylating agents (e.g., R$^b$C(=O)Cl, R$^a$OC(=O)Cl, and (R$^c$R$^d$)NC(=O)Cl) to give ketone (iii) (R$^a$, R$^b$, R$^c$, and R$^d$, for example, can be various optionally substituted cyclic groups and non-cyclic groups as defined in the claims and throughout). Ketone (iii) can be transformed using similar methods as shown in Schemes I, II and III to afford compounds of Formula I (v).

Scheme VII

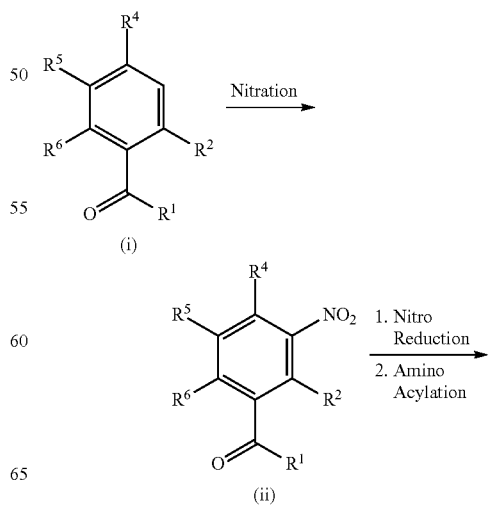

-continued

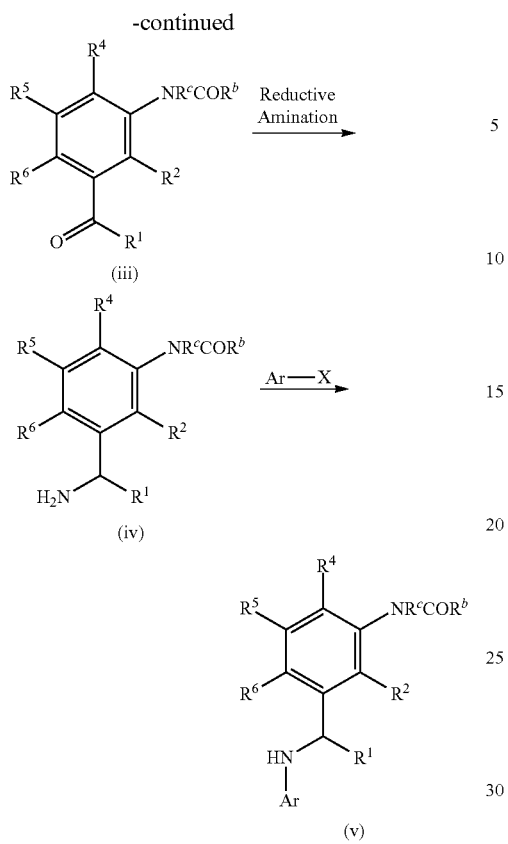

Scheme VIII

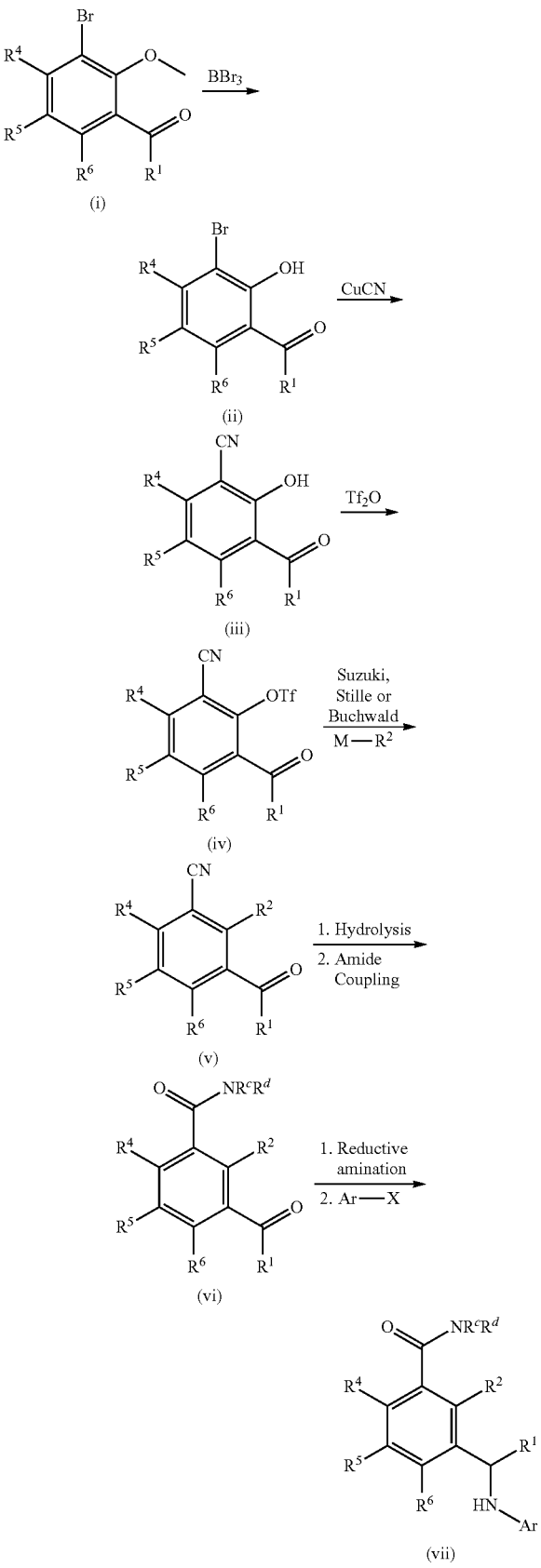

Further compounds which can be used in the processes of Schemes I-III can be formed as shown in Scheme VIII. Ether (i) can be converted to a phenol (ii) using standard conditions (e.g., BBr$_3$). The halo-phenol (ii) can be converted to the cyano-phenol (iii) using standard cyanation conditions (e.g., CuCN or Pd(0) and Zn(CN)$_2$). The phenol (iii) can be converted to the triflate (iv) using Tf$_2$O. The triflate group of (iv) can be coupled to R$^2$-M, where M is a boronic acid, boronic ester, or an appropriately substituted metal (e.g., R$^2$-M is R$^2$—B(OH)$_2$ or R$^2$—Sn(Bu)$_4$), under standard Suzuki conditions or standard Stille conditions (e.g., in the presence of a palladium(0) catalyst, such as tetrakis(triphenylphosphine)palladium(0) and a base (e.g., a bicarbonate or carbonate base)) to give a derivative of formula (v). Alternatively, R$^2$-M can be a cyclic amine (where M is H and attached to the amine nitrogen) with coupling to compound (iv) being performed by heating in base or under Buchwald conditions (e.g., in the presence of a palladium(0) catalyst, such as tetrakis(triphenylphosphine)palladium(0) and a base (e.g., an alkoxide base)) to afford ketone (v). Hydrolysis of the cyano group of (v) under acidic or basic conditions can give the carboxylic acid which can be coupled to amines using a coupling agent (e.g., HATU, HBTU, EDC) and an appropriate amine (HNR$^c$R$^d$) to give amide (vi). The ketone group of amide (vi) can be transformed using similar methods as shown in Schemes I, II and III to afford compounds of Formula I (vii).

Ketones which can be used in the processes of Scheme I, II and III, can also be formed as shown in Scheme IX. The carboxylic acid (i) can be activated with a coupling agent (e.g. HBTU or HATU) and then reacted with N, O-dimethylhydroxylamine to give a N-methoxy-N-methylcarboxamide. The phenols can be alkylated using Mitsunobu conditions (e.g., R'OH, DEAD, Ph$_3$P) or standard alkylating conditions (R$^1$-Lg, Lg=leaving group) to afford ether derivatives (ii). The halo group of (ii) (X$^1$ is halo) can be coupled to R$^3$-M, where M is a boronic acid, boronic ester or an appropriately substituted metal (e.g., R$^3$-M is R$^3$—B(OH)$_2$, R$^3$—Sn(Bu)$_4$, or Zn—R$^3$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of formula (iii). Alternatively, R$^3$-M can be a cyclic amine (where M is H and attached to the amine nitrogen) with coupling to compound (ii) being performed by heating in base or under Buchwald conditions (e.g., in the presence of a palladium(0) catalyst, such as tetrakis(triphenylphosphine)palladium(0) and a base (e.g., an alkoxide base)) to afford amides (iii). Reaction of compound (iii) with a Grignard reagent of formula R$^1$—MgX$^2$ (X$^2$=halo) can give ketone (iv). Ketone (iv) can be transformed using similar methods as shown in Schemes I, II and III to afford compounds of Formula I.

Scheme IX

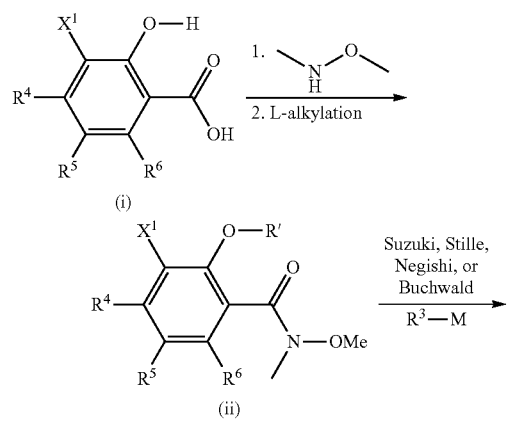

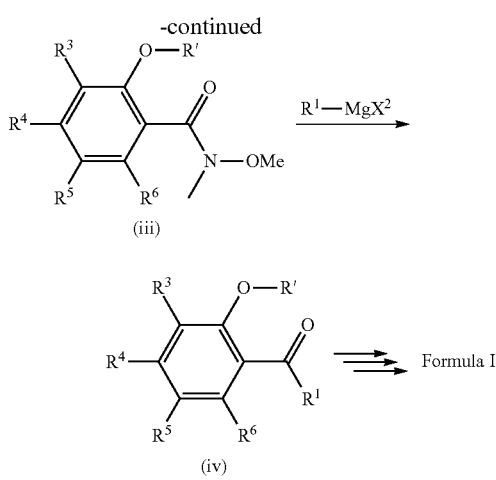

Ketones which can be used in the processes of Schemes I, II and III, can also be formed as shown in Scheme X below. The halo group (e.g., X$^1$=I) of (i) can be coupled to a zinc reagent R$^3$—Zn (e.g., such as tert-butyl 3-iodoazetidine-1-carboxylate with Zn dust) under standard Knochel/Negishi conditions (e.g., in the presence of a palladium(0) catalyst, such as tri-(2-furyl)phosphine and tris(dibenzylideneacetone)dipalladium(0) and 1,2-dibromoethane and chlorotrimethylsilane) to give ketone (ii). The azetidine (ii) can be deprotected (e.g., Pg=Boc, using TFA) and then reacted under alkylating, acylating or reductive amination (e.g., RX such as R—Br, RC(=O)Cl, R—S(O$_2$)Cl, RN=C=O or RCHO and a reducing agent) conditions to afford ketone derivatives (iii) which can be converted to compounds of Formula I (v) by similar methods shown in Schemes I, II, and III. Alternatively, ketone (ii) can be converted to compounds of formula (vii) using similar methods as shown in Schemes I, II and III. The protecting group on the amine of compound (vii) can be removed under standard conditions and then reacted under alkylating, acylating or reductive amination conditions (e.g., RX such as R—Br, RC(=O)Cl, R—S(O$_2$)Cl, RN=C=O or RCHO and a reducing agent) to give compounds of Formula I (v).

Scheme X

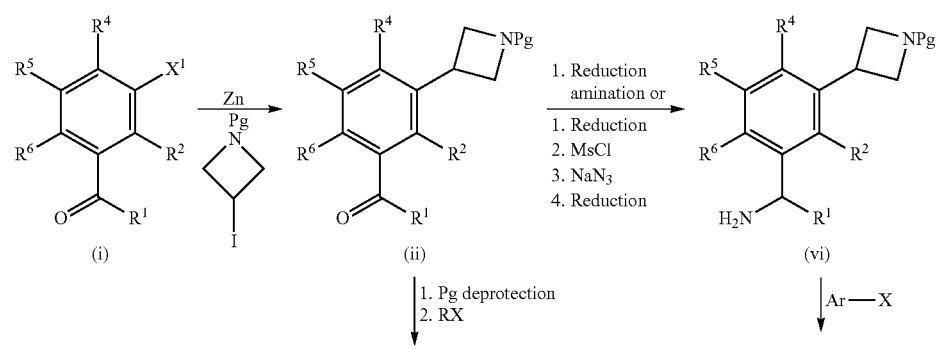

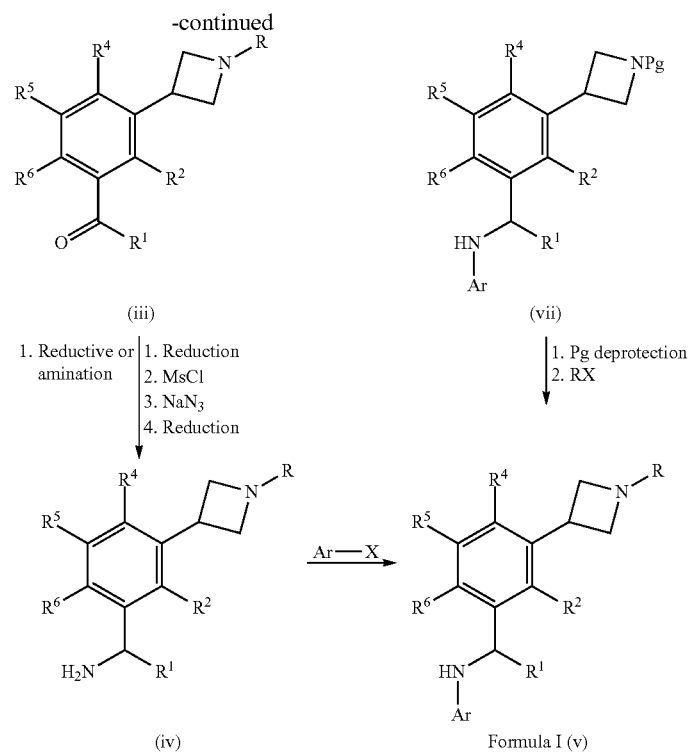

Compounds of Formula I can also be formed as shown in Scheme XI. The halo group of (i) can be coupled to an alkene (e.g., acrylate or acrylamide) under standard Heck conditions (e.g., in the presence of a palladium(II) catalyst, such as palladium acetate) to give an alkene of formula (ii). Reaction of alkene (ii) with nitromethane in the presence of DBU can afford the nitro derivative (iii) which can be reduced under standard conditions (e.g., NiCl$_2$/NaBH$_4$ or Raney Ni) to give a free amine which cyclizes to form lactam (iv). The lactam can be alkylated under standard conditions (e.g., R$^{3a}$—X$^2$, where X$^2$=halo, in the presence of a base, such as TEA or NaH) to give an N-alkyl-lactam (v). Compounds of formula (v), and pyrrolidines derived from the reduction of the lactam (v) with suitable reducing agents, such as LiAlH$_4$, can be converted to compounds of Formula I using conditions described in Schemes I, II and III.

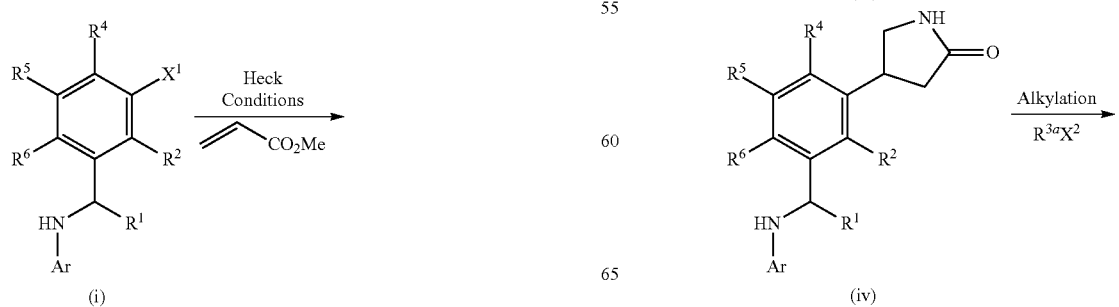

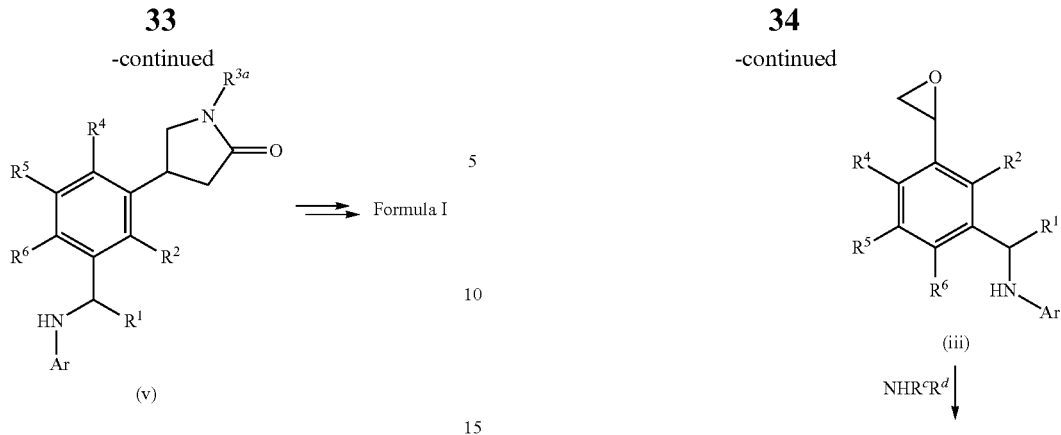

Compounds of Formula I can also be formed as shown in Scheme XII. The halo group of (i) can be coupled to $R^3$-M, where M is an appropriately substituted metal (e.g., $R^3$-M is $R^3B(OH)_2$; appropriate non-limiting starting materials for generating $R^3$-M are shown in Scheme XII) under standard Suzuki conditions (e.g., in the presence of a palladium(0) catalyst, such as tetrakis(triphenylphosphine)palladium(0)) to give an alkene of formula (ii). Epoxidation of alkene (ii) with mCPBA can afford the epoxide (iii) which can be reacted with a secondary or primary amine (amine=$NHR^cR^d$; $R^c$=H for primary amine) to give amino compounds of formula (iv). Secondary or tertiary amine derivatives (iv) can be further reacted with carbonyldiamidazole (CDI) or phosgene to form an oxazolidinone (v) or an acetyl-halide (e.g., chloro-acetylchloride in the presence of base, such as TEA) to give the N-acyl derivative which can be converted to the morpholinone derivative (vi) upon treatment with a base (e.g., NaH). Compounds of formula (iv, v, and vi) can be deprotected using standard conditions (e.g., compounds protected with THP groups may be treated with an acid, such as TFA or HCl) to give compounds of Formula I (iv, v, and vi).

Scheme XII

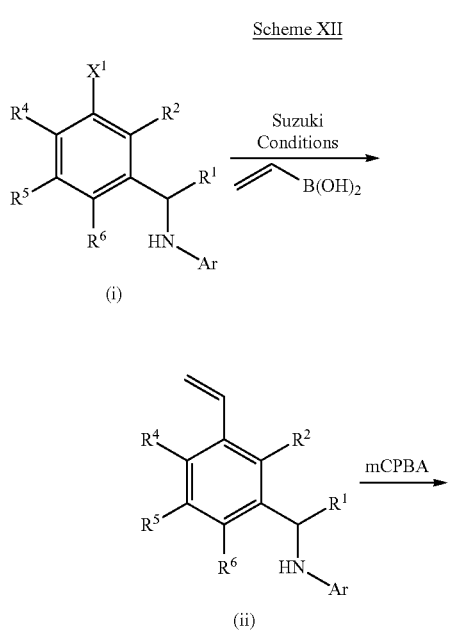

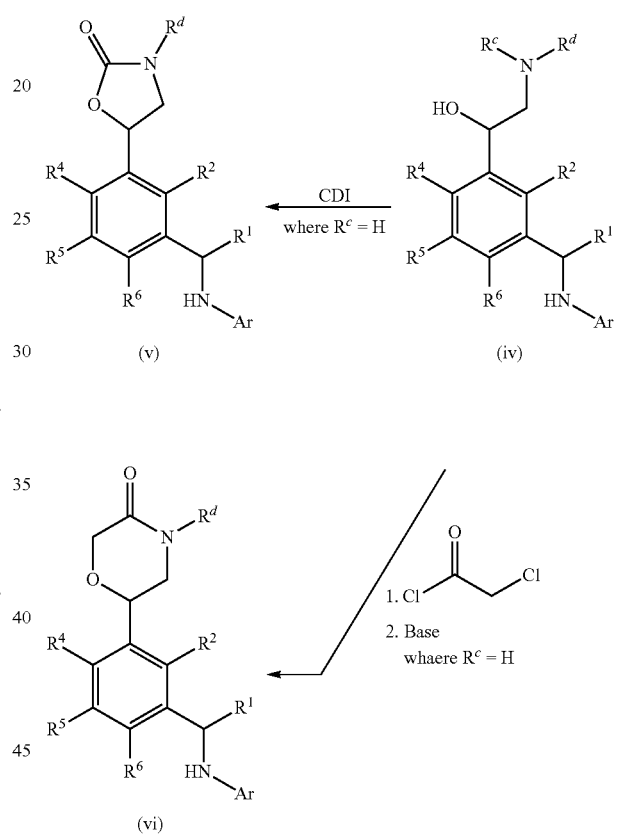

Compounds of Formula I can also be formed as shown in Scheme XIII. Sharpless amino-hydroxylation of an alkene of formula (i) under suitable conditions (A or B, as described in *JACS*, 2001, 123(9), 1862-1871 and *J. Org. Chem.*, 2011, 76, 358-372) can give either amino-hydroxy isomer (ii) or (iii). Compound (ii) can be reacted with carbonyldiamidazole or phosgene to form an oxazolidinone (iv), or an acetyl-halide (e.g., chloro-acetylchloride in the presence of base, such as TEA) to give an N-acyl derivative which can be converted to the morpholinone derivative (v) upon treatment with a base (e.g., NaH). The alternate amino-hydroxy isomer (iii) can be converted to oxazolidinone and morpholinone derivatives as shown in Scheme XII.

Scheme XIII

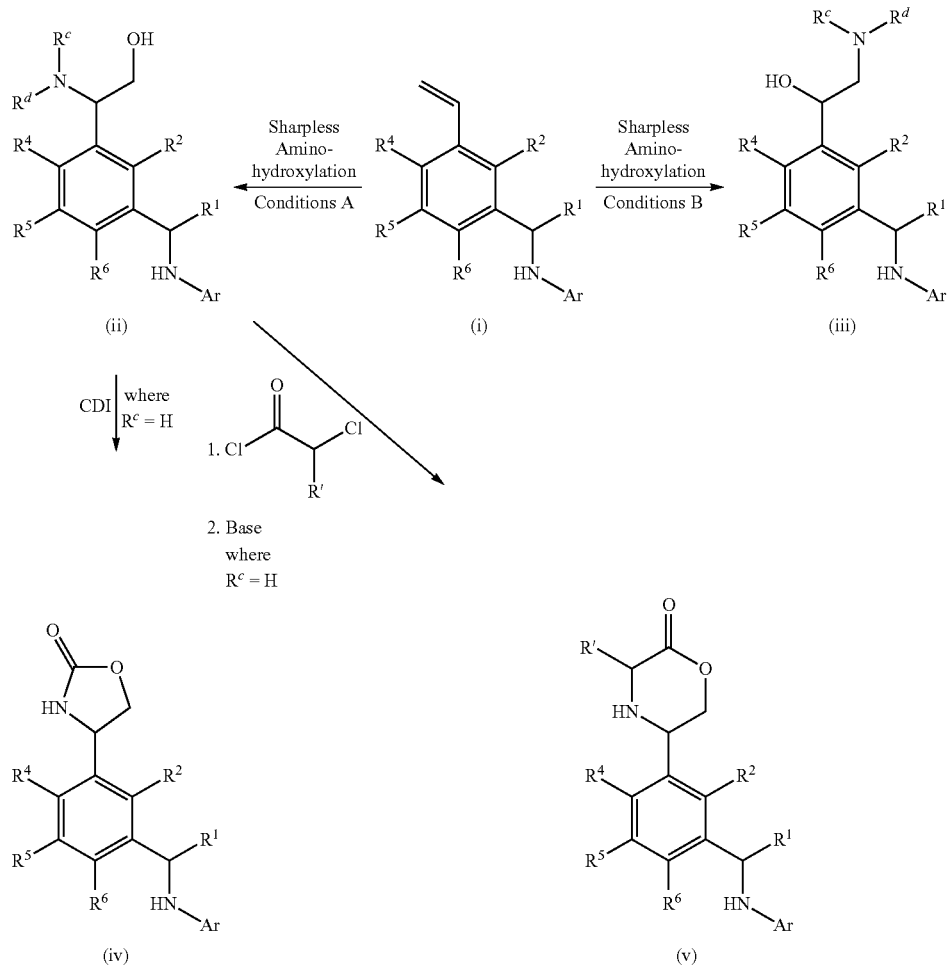

Compounds of Formula I can be synthesized as shown in Scheme XIV. The halo group (e.g., $X^1$=Cl, Br, I) of (i) can be converted to the boronate ester (ii) under standard conditions (e.g., pinacol boronate ester in the presence of a palladium(0) catalyst, such as tetrakis(triphenylphosphine)palladium(0)). Boronate (ii) can be reacted with an arylhalide or heteroarylhalide (e.g., $R^3$—$X^2$) under Suzuki conditions (e.g., in the presence of a palladium(0) catalyst, such as tetrakis(triphenylphosphine)palladium(0) and a base, such as $Na_2CO_3$) to give formula (iii). Formula (iii) can be converted to Formula I using the reaction conditions described in Schemes I, II or III.

Scheme XIV

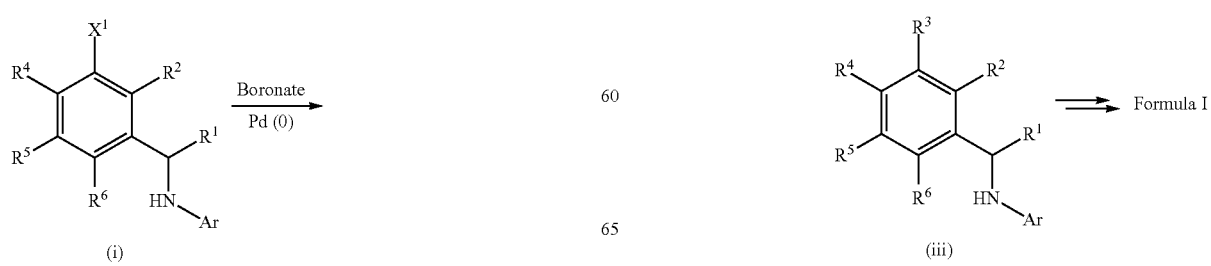

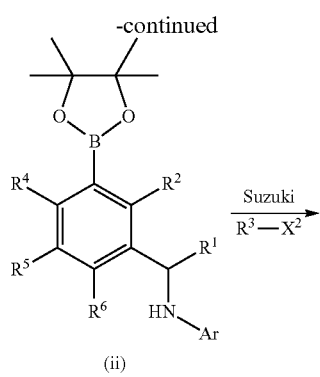

Compounds of Formula I, where $R^4$=F or CN, can be formed as shown in Scheme XV. Compound (i) can be acylated with a suitable acylating reagent (e.g., $R^1$—COCl) to form an ester which can be rearranged under Lewis acid conditions (e.g., $BF_3$/HOAc complex) to afford ketone (ii). Ketone (ii) can be halogenated with N-chlorosuccinamide, N-bromosuccinamide or N-iodosuccinamide to give phenol (iii), where $X^1$=Cl, Br, or I. Compound (iii) can be alkylated (e.g. $R^2$—$X^2$ and a base, such as NaH or $Na_2CO_3$; or under Mitsunobu conditions) to afford the ether (iv). The fluoro group of (iv) can be displaced (e.g., with NaCN or KCN) to give cyano derivative (v). The halo group of (v) can be coupled to $R^3$-M, where M is a boronic acid, boronic ester or an appropriately substituted metal (e.g., $R^3$-M is $R^3$—B$(OH)_2$, $R^3$—$Sn(Bu)_4$, or Zn—$R^3$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0)), to give a derivative of formula (vi). Alternatively, $R^3$-M can be a cyclic amine (where M is H and attached to the amine nitrogen) and coupled to compound (v) by heating in base or under Buchwald conditions (e.g., in the presence of a palladium(0) catalyst, such as tetrakis(triphenylphosphine)palladium(0) and a base (e.g., an alkoxide base)) to afford ketone (vi). Reduction of the ketone (vi) with a suitable reagent, such as sodium tetrahydroborate or the Corey CBS reagent can furnish the alcohol which can be converted to a derivative bearing a leaving group, (e.g., Lg is chloride via reaction with cyanuric chloride or mesylate via reaction with methanesulfonic anhydride) and then converted to amine (vii) via the azide. Amine (vii) can be converted to Formula I (viii) using conditions described in Schemes I, II and III. Alternatively the sequence can be inverted so that ketone (v) can be converted to amine (ix) and (x) and then the Suzuki, Stille, Negishi or Buchwald coupling is performed to give compounds of Formula I (viii) using conditions described in Schemes I, II and III.

Scheme XV

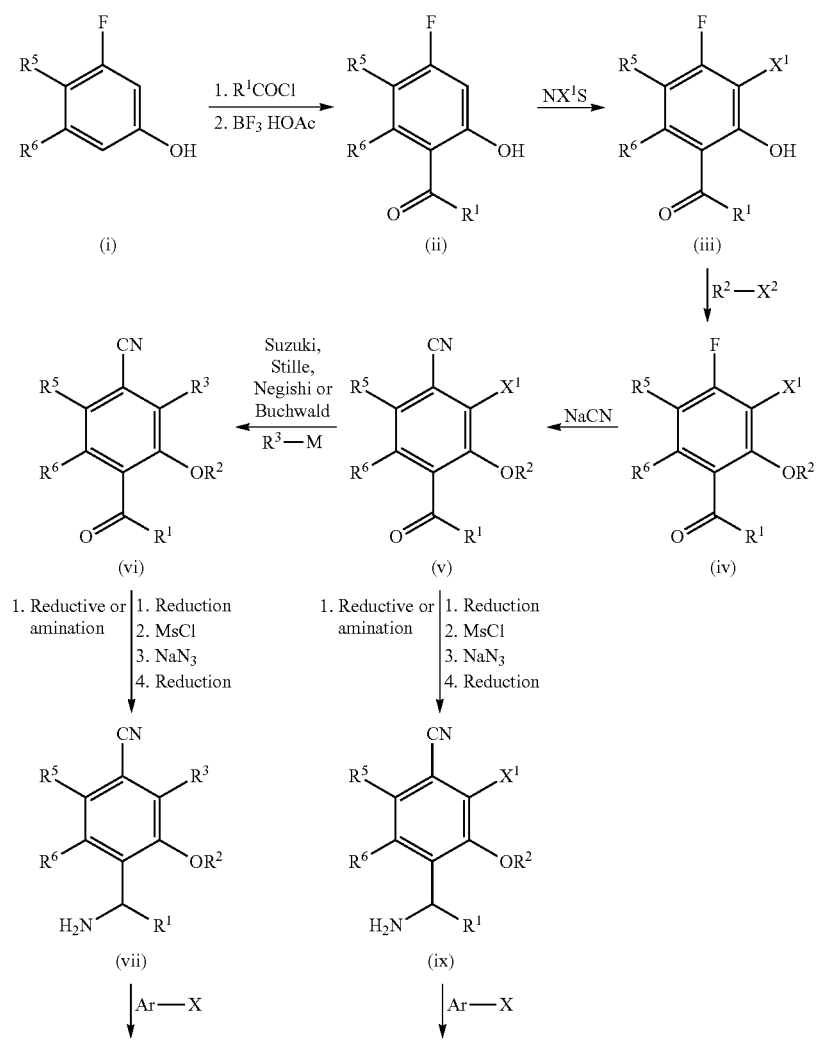

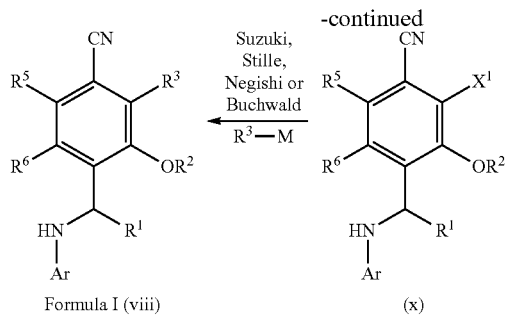

Compounds of Formula I can also be formed as shown in Scheme XVI. Compound (i) can be acylated with a suitable acylating reagent (e.g., $R^1$—C(=O)Cl) to form an ester which can be rearranged under Lewis acid conditions (e.g., $AlCl_3$ or $BF_3$/HOAc complex) to afford ketone (ii). Halogenation of ketone (ii) using $NX^1S$ (e.g., $NX^1S$=N-chlorosuccinamide, N-bromosuccinamide or N-iodosuccinamide) can give compound (iii), where $X^1$=Cl, Br, or I. The phenol can be converted to an ether (iv) using standard conditions (e.g., inorganic base, such as $K_2CO_3$, and an alkyl halide, such as Et-I). The halo group of (iv) can be coupled to $R^3$-M, where M is a boronic acid, boronic ester or an appropriately substituted metal (e.g., $R^3$-M is $R^3$—$B(OH)_2$, $R^3$—$Sn(Bu)_4$, or Zn—$R^3$ and $R^3$ is a substituted or unsubstituted olefin, such as vinyl) under standard Suzuki conditions or standard Stille conditions (e.g., in the presence of a palladium(0) catalyst, such as tetrakis(triphenylphosphine)palladium(0) and a base (e.g., a bicarbonate or carbonate base) to give a derivative of formula (v). The alkene can then be dihydroxylated using Sharpless conditions to afford the diol (vi). Enhancement of one enantiomer of the secondary alcohol can be achieved using standard Sharpless asymmetric dihydroxylation methods. The secondary alcohol can be converted to the N-Boc protected amine via a 6-step process (e.g. silyl protection (e.g., TBS—Cl and DIEA) of the primary alcohol, mesylation of the secondary alcohol, displacement of the mesylate with $NaN_3$, reduction of the azide with $Ph_3P$, Boc protection of the resulting primary amine and then deprotection of the silyl protecting group on the primary alcohol with TBAF) to afford amino-alcohol (vii). The amino-alcohol (vii) can be converted into the oxazolidinone by treatment with phosgene to give ketone (viii). Ketone (viii) can be converted to compounds of Formula I (x) using conditions described in Schemes I, II and III.

Scheme XVI

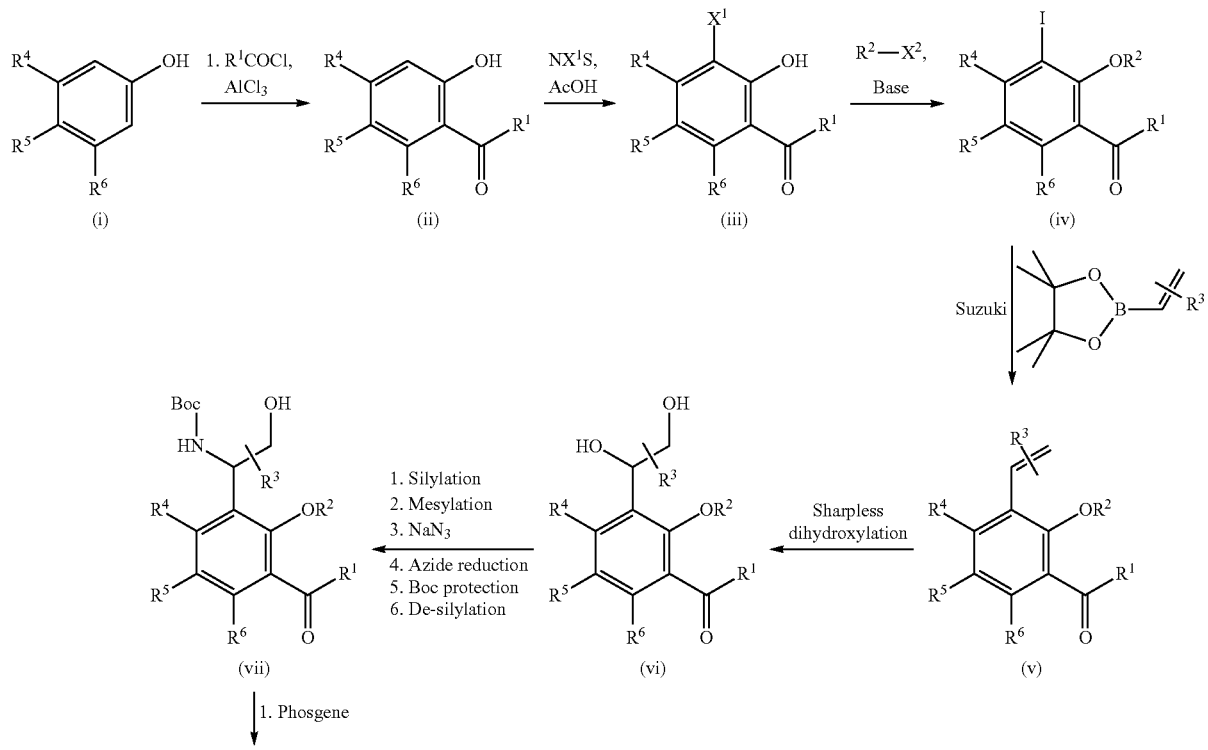

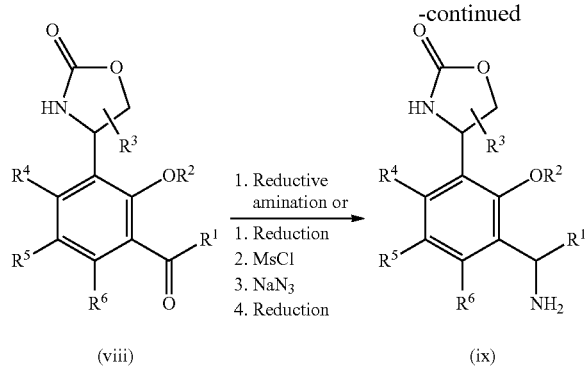
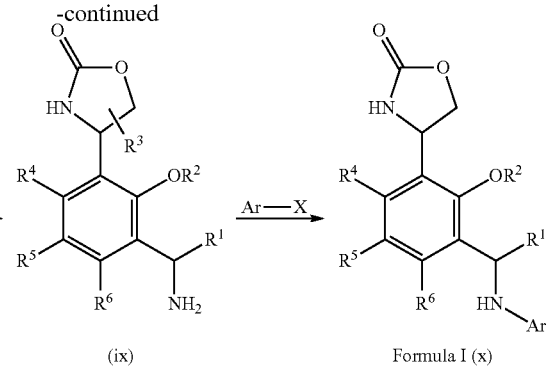

Methods

The compounds of the invention can modulate activity of one or more of various kinases including, for example, phosphoinositide 3-kinases (PI3Ks). The term "modulate" is meant to refer to an ability to increase or decrease the activity of one or more members of the PI3K family. Accordingly, the compounds of the invention can be used in methods of modulating a PI3K by contacting the PI3K with any one or more of the compounds or compositions described herein. In some embodiments, compounds of the present application can act as inhibitors of one or more PI3Ks. In further embodiments, the compounds of the invention can be used to modulate activity of a PI3K in an individual in need of modulation of the receptor by administering a modulating amount of a compound of the invention, or a pharmaceutically acceptable salt thereof. In some embodiments, modulating is inhibiting.

Given that cancer cell growth and survival is impacted by multiple signaling pathways, the present application is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present compounds bind and/or modulate (e.g., inhibit) include any member of the PI3K family. In some embodiments, the PI3K is PI3Kα, PI3β, PI3Kγ, or PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

In some embodiments, more than one compound of the invention is used to inhibit the activity of one kinase (e.g., PI3Kγ or PI3Kδ).

In some embodiments, more than one compound of the invention is used to inhibit more than one kinase, such as at least two kinases (e.g., PI3Kγ and PI3Kδ).

In some embodiments, one or more of the compounds is used in combination with another kinase inhibitor to inhibit the activity of one kinase (e.g., PI3Kγ or PI3Kδ).

In some embodiments, one or more of the compounds is used in combination with another kinase inhibitor to inhibit the activities of more than one kinase (e.g., PI3Kγ or PI3Kδ), such as at least two kinases.

The compounds of the invention can be selective. By "selective" is meant that the compound binds to or inhibits a kinase with greater affinity or potency, respectively, compared to at least one other kinase. In some embodiments, the compounds of the invention are selective inhibitors of PI3Kγ or PI3Kδ over PI3Kα and/or PI3β. In some embodiments, the compounds of the invention are selective inhibitors of PI3Kδ (e.g., over PI3Kα, PI3β and PI3Kγ). In some embodiments, the compounds of the invention are selective inhibitors of PI3Kγ (e.g., over PI3Kα, PI3β and PI3Kδ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase (such as PI3K)-associated disease or disorder in an individual (e.g., patient) by administering to the individual in need of such treatment a therapeutically effective amount or dose of one or more compounds of the present application or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, atherosclerosis, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome, and the like.

Further examples of PI3K-associated diseases include idiopathic thrombocytopenic purpura (ITP), autoimmune hemolytic anemia (AIHA), vasculitis, systemic lupus erythematosus, lupus nephritis, pemphigus, membranous nephropathy, chronic lymphocytic leukemia (CLL), Non-Hodgkin lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma.

In some embodiments, the present application provides a method of treating pemphigus, membranous nephropathy, Hodgkin's lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), or monoclonal gammopathy of undetermined significance (MGUS).

In some embodiments, the present application provides a method of treating osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome.

In some embodiments, the disease is idiopathic thrombocytopenic purpura (ITP), autoimmune hemolytic anemia (AIHA), vasculitis, pemphigus, or membranous nephropathy.

In some embodiments, the idiopathic thrombocytopenic purpura (ITP) is selected from relapsed ITP and refractory ITP.

In some embodiments, the vasculitis is selected from Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schnlein purpura (HSP), hypersensitivity vasculitis, microscopic polyangiitis, Wegener's granulomatosis, and anti-neutrophil cytoplasm antibody associated (ANCA) systemic vasculitis (AASV).

In some embodiments, the present application provides methods of treating an immune-based disease, cancer, or lung disease in a patient.

In some embodiments, the immune-based disease is systemic lupus erythematosus or lupus nephritis.

In some embodiments, the cancer is breast cancer, prostate cancer, colon cancer, endometrial cancer, brain cancer, bladder cancer, skin cancer, cancer of the uterus, cancer of the ovary, lung cancer, pancreatic cancer, renal cancer, gastric cancer, or a hematological cancer.

In some embodiments, the hematological cancer is acute myeloblastic leukemia, chronic myeloid leukemia, B cell lymphoma, chronic lymphocytic leukemia (CLL), Non-Hodgkins lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma.

In some embodiments, the non-Hodgkin lymphoma (NHL) is selected from relapsed NHL, refractory NHL, and recurrent follicular NHL.

In some embodiments, the lung disease is acute lung injury (ALI) or adult respiratory distress syndrome (ARDS).

As used herein, the term "contacting" refers to the bringing together of indicated moieties in an in vitro system or an in vivo system. For example, "contacting" a PI3K with a compound of the invention includes the administration of a compound of the present application to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, EGFR, HER2, JAK (e.g., JAK1 or JAK2), c-MET, VEGFR, PDGFR, cKit, IGF-1R, RAF, FAK, Akt mTOR, PIM, and AKT (e.g., AKT1, AKT2, or AKT3) kinase inhibitors such as, for example, those described in WO 2006/056399, or other agents such as, therapeutic antibodies can be used in combination with the compounds of the present application for treatment of PI3K-associated diseases, disorders or conditions. The one or more additional pharmaceutical agents can be administered to a patient simultaneously or sequentially.

In some embodiments, the additional pharmaceutical agent is a JAK1 and/or JAK2 inhibitor. In some embodiments, the present application provides a method of treating a disease described herein (e.g., a B cell malignancy, such as diffuse B-cell lymphoma) in a patient comprising administering to the patient a compound described herein, or a pharmaceutically acceptable salt thereof, and a JAK1 and/or JAK2 inhibitor. The B cell malignancies can include those described herein and in U.S. Ser. No. 61/976,815, filed Apr. 8, 2014. In some embodiments, the inhibitor of JAK1 and/or JAK2 is 3-cyclopentyl-3-[4-(7H-pyrrolo[2,3-d]pyrimidin-4-yl)-1H-pyrazol-1-yl]propanenitrile. In some embodiments, the inhibitor of JAK1 and/or JAK2 is (3R)-3-cyclopentyl-3-[4-(7H-pyrrolo[2,3-d]pyrimidin-4-yl)-1H-pyrazol-1-yl]propanenitrile (ruxolitinib; also known as INCB018424). Ruxolitinib has an $IC_{50}$ of less than 10 nM at 1 mM ATP (assay J) at JAK1 and JAK2. 3-Cyclopentyl-3-[4-(7H-pyrrolo[2,3-d]pyrimidin-4-yl)-1H-pyrazol-1-yl]propanenitrile and ruxolitinib can be made by the procedure described in U.S. Pat. No. 7,598,257 (Example 67), filed Dec. 12, 2006, which is incorporated herein by reference in its entirety. In some embodiments, the inhibitor of JAK1 and/or JAK2 is (3R)-3-cyclopentyl-3-[4-(7H-pyrrolo[2,3-d]pyrimidin-4-yl)-1H-pyrazol-1-yl]propanenitrile phosphoric acid salt.

In some embodiments, the inhibitor of JAK1 and/or JAK2 is a compound of Table 1, or a pharmaceutically acceptable salt thereof. The compounds in Table 1 are selective JAK1 inhibitors (selective over JAK2, JAK3, and TYK2). The $IC_{50}$s obtained by the method of Assay J at 1 mM ATP are shown in Table 1.

TABLE 1

| # | Prep. | Name | Structure | JAK1 $IC_{50}$ (nM) | JAK2/JAK1 |
|---|---|---|---|---|---|
| 1 | Example J1 herein | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 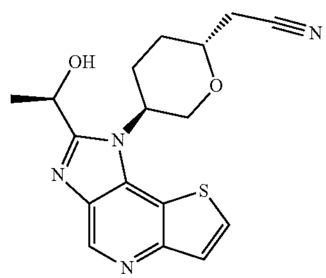 [SMILES: C[C@@H](O)c1nc2cnc3ccsc3c2n1[C@H]1CC[C@H](CC#N)OC1] | ++ | >10 |
| 2 | Example J2 herein | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 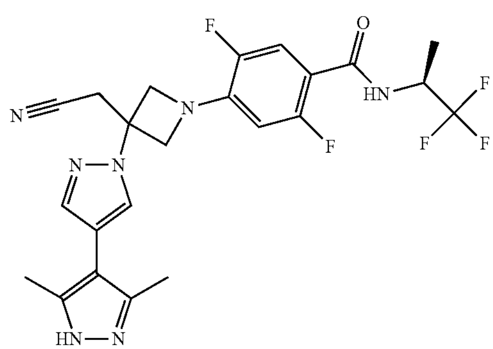 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 3 | US 2010/0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 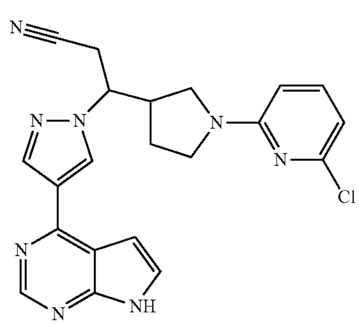 [SMILES: N#CCC(C1CCN(c2cccc(Cl)n2)C1)n1cc(-c2ncnc3[nH]ccc23)cn1] | + | >10 |

TABLE 1-continued

| # | Prep. | Name | Structure | JAK1 IC$_{50}$ (nM) | JAK2/ JAK1 |
|---|---|---|---|---|---|
| 4 | US 2010/ 0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 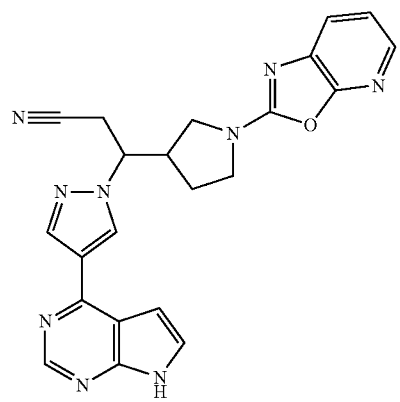 [SMILES: N#CCC(C1CCN(c2nc3cccnc3o2)C1)n1cc(-c2ncnc3[nH]ccc23)cn1] | + | >10 |
| 5 | US 2011/ 0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzamide | 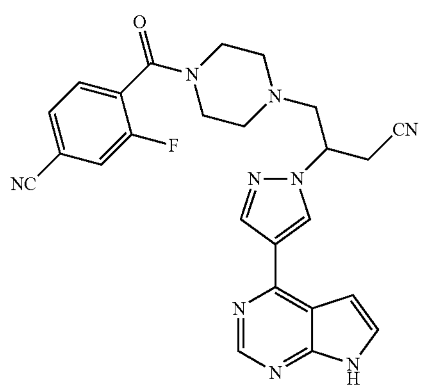 [SMILES: N#CCC(CN1CCN(C(=O)c2ccc(C#N)cc2F)CC1)n1cc(-c2ncnc3[nH]ccc23)cn1] | + | >10 |
| 6 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 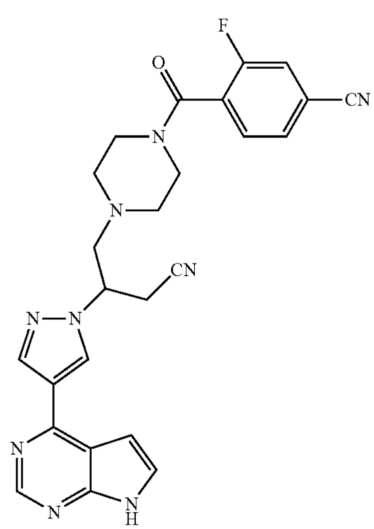 [SMILES: N#CCC(CN1CCN(C(=O)c2ccc(C#N)cc2F)CC1)n1cc(-c2ncnc3[nH]ccc23)cn1] | + | >10 |

TABLE 1-continued

| # | Prep. | Name | Structure | JAK1 IC$_{50}$ (nM) | JAK2/JAK1 |
|---|---|---|---|---|---|
| 7 | US 2011/0224190 Example 1) | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile | 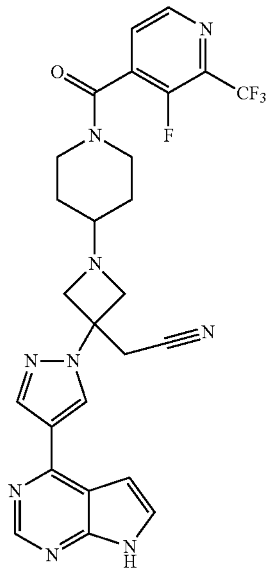 [SMILES: N#CCC1(n2cc(-c3ncnc4[nH]ccc34)cn2)CN(C2CCN(C(=O)c3ccnc(C(F)(F)F)c3F)CC2)C1] | + | >10 |
| 8 | US 2011/0224190 Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 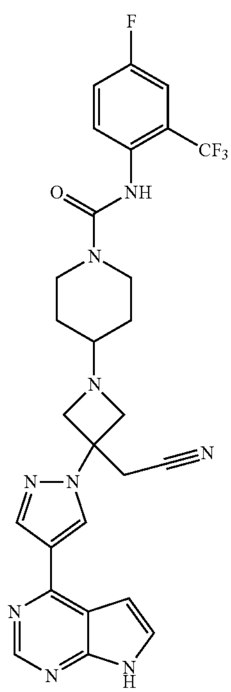 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |

TABLE 1-continued

| # | Prep. | Name | Structure | JAK1 IC$_{50}$ (nM) | JAK2/ JAK1 |
|---|---|---|---|---|---|
| 9 | US 2011/ 0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 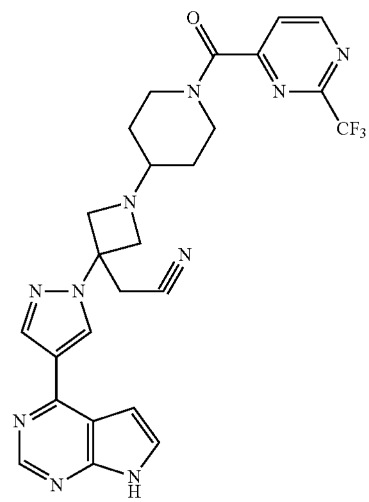 [SMILES: N#CCC1(n2cc(-c3ncnc4[nH]ccc34)cn2)CN(C2CCN(C(=O)c3ccnc(C(F)(F)F)n3)CC2)C1] | + | >10 |
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 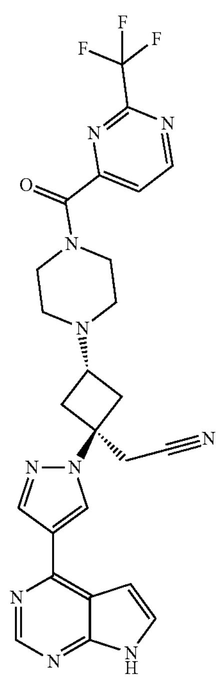 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |

TABLE 1-continued

| # | Prep. | Name | Structure | JAK1 IC$_{50}$ (nM) | JAK2/JAK1 |
|---|---|---|---|---|---|
| 11 | US 2012/0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 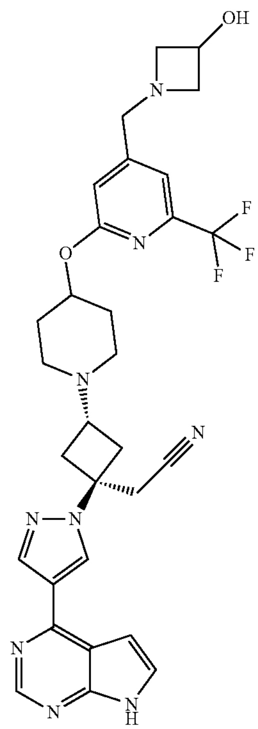 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |
| 12 | US 2012/0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 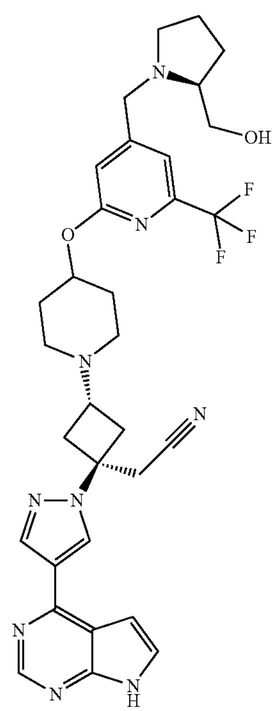 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |

TABLE 1-continued

| # | Prep. | Name | Structure | JAK1 IC$_{50}$ (nM) | JAK2/ JAK1 |
|---|---|---|---|---|---|
| 13 | US 2012/ 0149681 (Example 162) | {trans-3-(4-{[4-{[(2R)-2-(hydroxymethyl) pyrrolidin-1-yl]methyl}-6-(trifluoromethyl) pyridin-2-yl]oxy}piperidin-1-yl)-1-[4-(7H-pyrrolo[2,3-d]pyrimidin-4-yl)-1H-pyrazol-1-yl]cyclobutyl} acetonitrile | 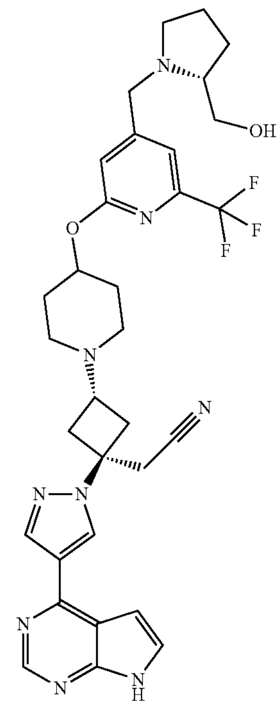 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |
| 14 | US 2012/ 0149682 (Example 20)[b] | 4-(4-{3-[(dimethylamino) methyl]-5-fluorophenoxy}piperidin-1-yl)-3-[4-(7H-pyrrolo[2,3-d]pyrimidin-4-yl)-1H-pyrazol-1-yl]butanenitrile | 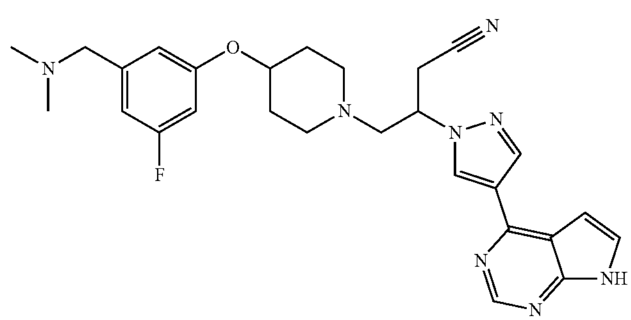 [SMILES: CN(C)Cc1cc(F)cc(OC2CCN(CC(CC#N)n3cc(-c4ncnc5[nH]ccc45)cn3)CC2)c1] | + | >10 |
| 15 | US 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 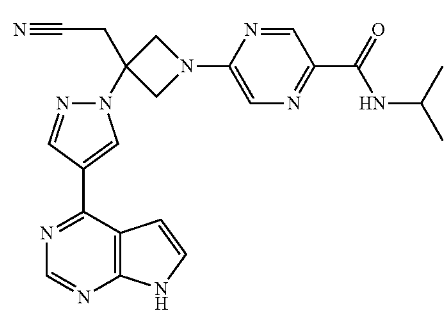 [SMILES: CC(C)NC(=O)c1cnc(N2CC(CC#N)(n3cc(-c4ncnc5[nH]ccc45)cn3)C2)cn1] | + | >10 |

TABLE 1-continued

| # | Prep. | Name | Structure | JAK1 IC$_{50}$ (nM) | JAK2/JAK1 |
|---|---|---|---|---|---|
| 16 | US 2013/0018034 (Example 28) | 4-{3-(cyanomethyl)-3-[4-(7H-pyrrolo[2,3-d]pyrimidin-4-yl]azetidin-1-yl}-2,5-difluoro-N-[(1S)-2,2,2-trifluoro-1-methylethyl]benzamide | 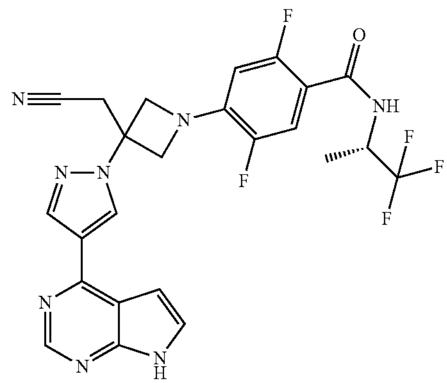 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/0018034 (Example 34) | 5-{3-(cyanomethyl)-3-[4-(1H-pyrrolo[2,3-d]pyridin-4-yl)-1H-pyrazol-1-yl]azetidin-1-yl}-N-isopropylpyrazine-2-carboxamide | 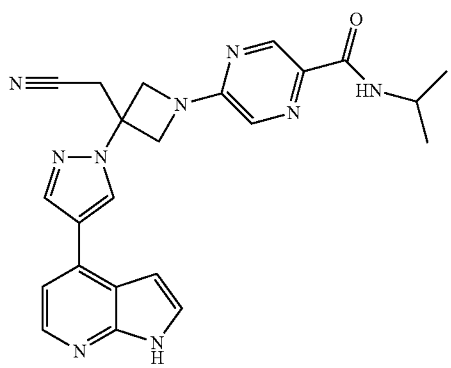 [SMILES: CC(C)NC(=O)c1cnc(N2CC(CC#N)(n3cc(-c4ccnc5[nH]ccc45)cn3)C2)cn1] | + | >10 |
| 18 | US 2013/0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 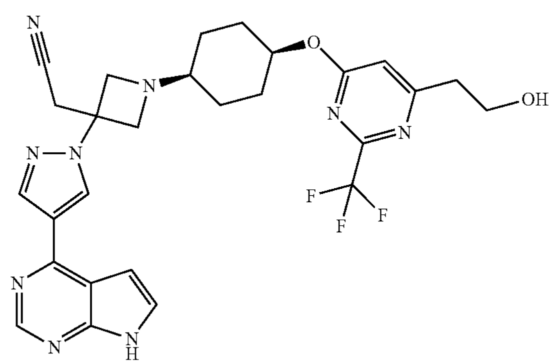 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | US 2013/0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 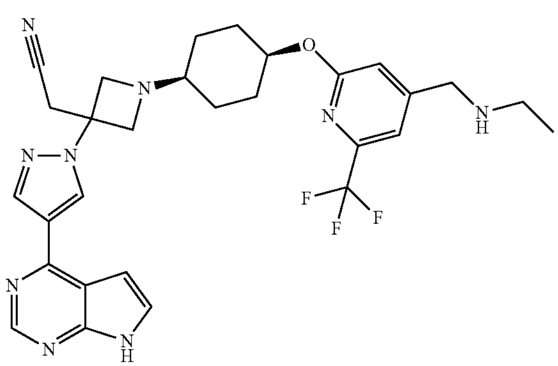 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |

TABLE 1-continued

| # | Prep. | Name | Structure | JAK1 IC$_{50}$ (nM) | JAK2/JAK1 |
|---|---|---|---|---|---|
| 20 | US 2013/0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 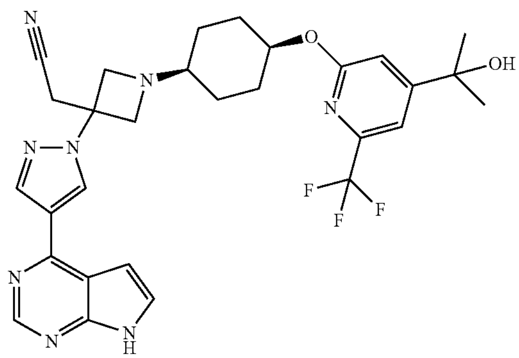 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | US 2013/0045963 (Example 95) | {1-(cis-4-{[4-{[(3R)-3-hydroxypyrrolidin-1-yl]methyl}-6-(trifluoromethyl)pyridin-2-yl]oxy}cyclohexyl-3-[4-(7H-pyrrolo[2,3-d]pyrimidin-4-yl)-1H-pyrazol-1-yl]azetidin-3-yl}acetonitrile | 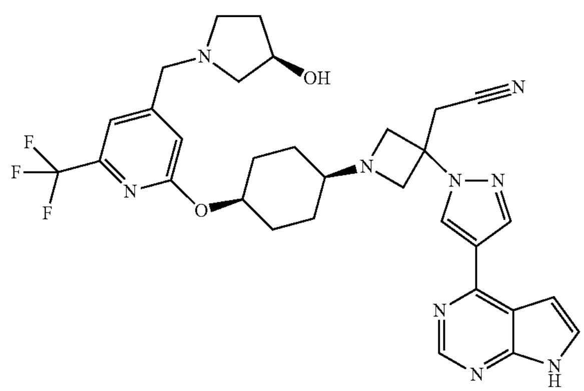 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | US 2013/0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 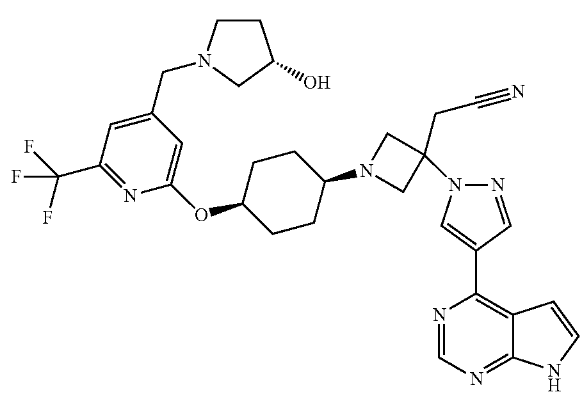 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |

TABLE 1-continued

| # | Prep. | Name | Structure | JAK1 IC$_{50}$ (nM) | JAK2/ JAK1 |
|---|---|---|---|---|---|
| 23 | US 2014/ 0005166 (Example 1) | {trans-3-(4-{[4-({[(1S)-2-hydroxy-1-methylethyl]amino} methyl)-6-(trifluoromethyl) pyridin-2-yl]oxy}piperidin-1-yl)-1-[4-(7H-pyrrolo[2,3-d]pyrimidin-4-yl)-1H-pyrazol-1-yl]cyclobutyl} acetonitrile | 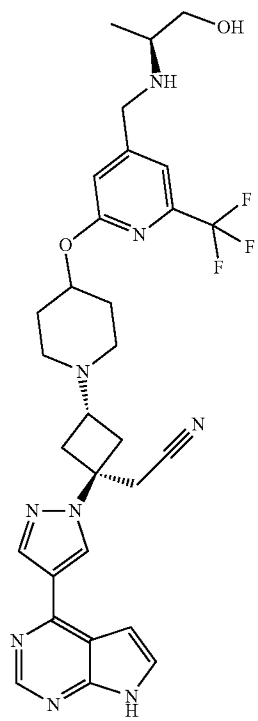 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |
| 24 | US 2014/ 0005166 (Example 14) | {trans-3-(4-{[4-({[(2R)-2-hydroxypropyl] amino}methyl)-6-(trifluoromethyl) pyridin-2-yl]oxy}piperidin-1-yl)-1-[4-(7H-pyrrolo[2,3-d]pyrimidin-4-yl)-1H-pyrazol-1-yl]cyclobutyl} acetonitrile | 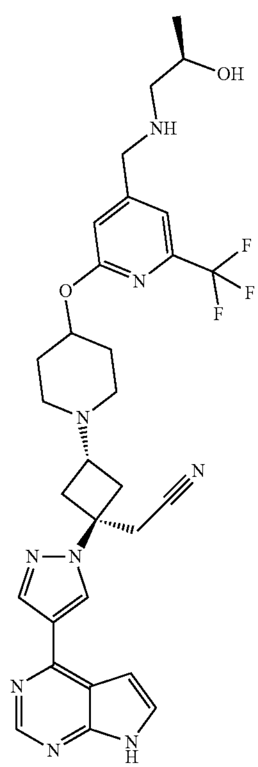 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| # | Prep. | Name | Structure | JAK1 IC$_{50}$ (nM) | JAK2/JAK1 |
|---|---|---|---|---|---|
| 25 | US 2014/0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 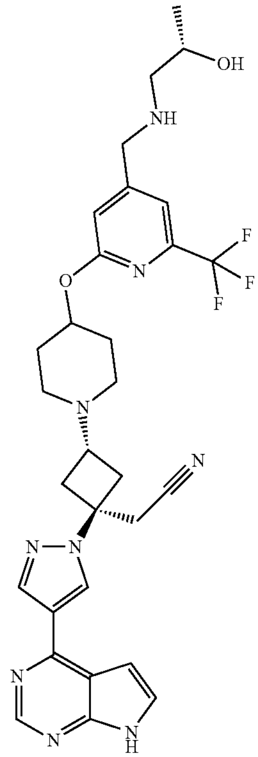 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 26 | US 2014/0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 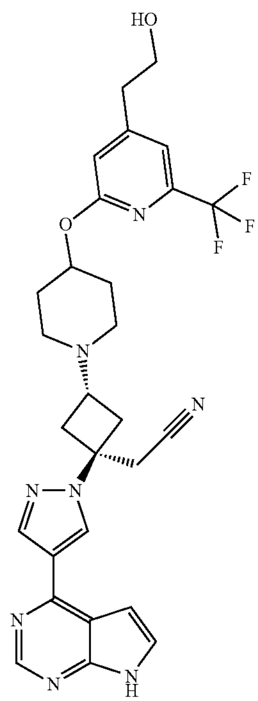 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see Example A for assay conditons)
++ means ≤100 nM (see Example A for assay conditions)
+++ means ≤300 nM (see Example A for assay conditions)
$^a$Data for enantiomer 1
$^b$Data for enantiomer 2

In some embodiments, the inhibitor of JAK1 and/or JAK2 is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the inhibitor of JAK1 and/or JAK2 is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

In some embodiments, the inhibitor of JAK1 and/or JAK2 is 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide, or a pharmaceutically acceptable salt thereof.

In some embodiments, the inhibitor of JAK1 and/or JAK2 is selected from (R)-3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, (R)-3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile, (R)-4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, (R)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, or (R)-4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile, (S)-3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, (S)-3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile, (S)-4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, (S)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, (S)-4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile; and pharmaceutically acceptable salts of any of the aforementioned.

In some embodiments, the compounds of Table 1 are prepared by the synthetic procedures described in US Patent Publ. No. 2010/0298334, filed May 21, 2010, US Patent Publ. No. 2011/0059951, filed Aug. 31, 2010, US Patent Publ. No. 2011/0224190, filed Mar. 9, 2011, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the inhibitor of JAK1 and/or JAK2 is selected from the compounds of US Patent Publ. No. 2010/0298334, filed May 21, 2010, US Patent Publ. No. 2011/0059951, filed Aug. 31, 2010, US Patent Publ. No. 2011/0224190, filed Mar. 9, 2011, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present application and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, MDL-101,731, bendamustine (Treanda), ofatumumab, and GS-1101 (also known as CAL-101).

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable mTOR inhibitors include compounds, and their pharmaceutically acceptable salts, as disclosed in WO 2011/025889.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present application with an additional agent. Furthermore, resistance of multiple myeloma cells to agents such as dexamethasone may be reversible upon treatment with the PI3K inhibitor of the present application. The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

In some further embodiments, combinations of the compounds of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present application. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present application.

The tablets or pills of the present application can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present application can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Labeled Compounds and Assay Methods

Another aspect of the present application relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present application includes PI3K assays that contain such labeled compounds.

The present application further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present application include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. The radionuclide that is incorporated in the instant radio-labeled compounds will depend on the specific application of that radio-labeled compound. For example, for in vitro PI3K labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, one or more H atoms for any compound described herein is each replaced by a deuterium atom.

The present application can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present application also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3K inhibitors according to at least one assay described herein.

EXAMPLES

Experimental procedures for compounds of the invention are provided below. The example compounds below containing one or more chiral centers were obtained in racemate form or as isomeric mixtures, unless otherwise specified. Salt stoichiometry which is indicated any of the products below is meant only to indicate a probable stoichiometry, and should not be construed to exclude the possible formation of salts in other stoichiometries. The abbreviations "h" and "min" refer to hour(s) and minute(s), respectively.

Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity analysis under the following conditions; Instrument; Agilent 1100 series, LC/MSD, Column: Waters Sunfire™ $C_{18}$ 5 lam, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ C18 5 lam, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 lam, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1. 4-{3-Chloro-6-ethoxy-2-fluoro-5-[1-([1,3]thiazolo[5,4-d]pyrimidin-7-ylamino)ethyl]phenyl}pyrrolidin-2-one trifluoroacetate

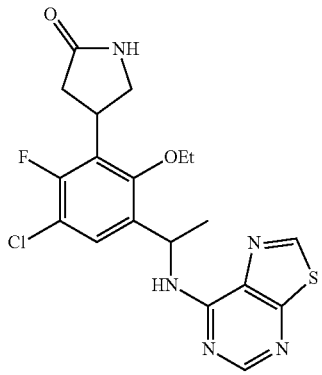 [SMILES: CCOc1c(C(C)Nc2ncnc3scnc23)cc(Cl)c(F)c1C1CNC(=O)C1]

Step 1. 4-(3-(1-Azidoethyl)-5-chloro-2-ethoxy-6-fluorophenyl)pyrrolidin-2-one

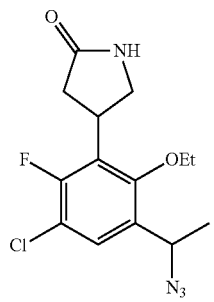 [SMILES: CCOc1c(C(C)N=[N+]=[N-])cc(Cl)c(F)c1C1CNC(=O)C1]

A mixture of 4-[3-chloro-6-ethoxy-2-fluoro-5-(1-hydroxyethyl)phenyl]pyrrolidin-2-one (0.437 g, 1.45 mmol) (from US 2013/0059835, Examples 345-348, Step 6) and N,N-dimethylformamide (0.0112 mL, 0.145 mmol) in dichloromethane (12 mL) was treated with thionyl chloride (0.222 mL, 3.04 mmol) dropwise. The reaction mixture was stirred for 30 min, added dropwise to ice-cooled saturated sodium bicarbonate solution, and extracted with dichloromethane. The organic layer was washed with brine, dried over anhydrous sodium sulfate, filtered, and concentrated to yield a chloride intermediate (0.463 g, 100%) that was used without further purification. The chloride intermediate was dissolved in N,N-dimethylformamide (4.35 mL), treated with sodium azide (0.282 g, 4.34 mmol), and heated at 60° C. for 1 h. The reaction mixture was poured over saturated sodium bicarbonate solution (30 mL) and water (30 mL) and extracted with ethyl acetate (2×50 mL). The combined organic extracts were washed with brine, dried over anhydrous sodium sulfate, filtered, and concentrated to a brown solid. Purification by flash column chromatography (100% DCM to 10% MeOH/DCM) afforded the desired product (0.47 g, 99%) as a white solid. LCMS calculated for $C_{14}H_{17}ClFN_4O_2$ $(M+H)^+$: m/z=327.1. found: 326.9.

Step 2. 4-[3-(1-Aminoethyl)-5-chloro-2-ethoxy-6-fluorophenyl]pyrrolidin-2-one

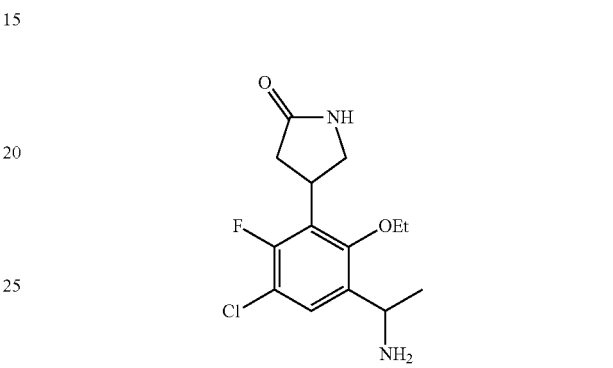

A solution of 4-[3-(1-azidoethyl)-5-chloro-2-ethoxy-6-fluorophenyl]pyrrolidin-2-one (0.461 g, 1.41 mmol) in tetrahydrofuran (7.6 mL) and water (1.5 mL) was treated with 1.0 M trimethylphosphine in THF (1.76 mL, 1.76 mmol) and stirred for 30 min. The reaction mixture was diluted with DCM (50 mL) and washed with water (50 mL). The aqueous layer was separated and re-extracted with DCM (50 mL). The combined organic extracts were washed with saturated sodium bicarbonate solution, dried over anhydrous sodium sulfate, filtered, and concentrated to a colorless foam. Purification by flash column chromatography (100% DCM to 15% MeOH/DCM) afforded the desired product (0.37 g, 86%) as a white foam. LCMS calculated for $C_{14}H_{19}ClFN_2O_2$ $(M+H)^+$: m/z=301.1. found: 301.0.

Step 3. 4-{3-Chloro-6-ethoxy-2-fluoro-5H-([1-([1,3]thiazolo[5,4-d]pyrimidin-7-ylamino)ethyl]phenyl}pyrrolidin-2-one A solution of 4-[3-(1-aminoethyl)-5-chloro-2-ethoxy-6-fluorophenyl]pyrrolidin-2-one (30 mg, 0.333 mmol) and 7-chloro[1,3]thiazolo[5,4-d]pyrimidine (25.7 mg, 0.15 mmol) [AK-58025, Ark Pharm] in 1-butanol (6.6 mL) was treated with N,N-diisopropylethylamine (0.052 mL, 0.30 mmol) and heated at 114° C. for 2.5 h. The reaction mixture was then concentrated to a yellow residue. Purification by preparative LCMS (pH 2) afforded the title product (0.033 g, 60%) as a white solid as a mixture of four diastereoisomers. $^1$H NMR (300 MHz, DMSO-$d_6$) δ 9.30 (s, 1H), 8.78 (d, J=8.4 Hz, 1H), 8.37 (d, J=1.8 Hz, 1H), 7.82 (s, 1H), 7.71 (d, J=8.3 Hz, 1H), 5.91-5.70 (m, 1H), 4.29-4.14 (m, 1H), 4.13-3.96 (m, 1H), 3.95-3.81 (m, 1H), 3.60 (dd, J=9.3, 9.3 Hz, 1H), 3.26 (dd, J=7.8, 7.3 Hz, 1H), 2.42-2.21 (m, 2H), 1.59-1.32 (m, 6H); LCMS calculated for $C_{19}H_{20}ClFN_5O_2S$ $(M+H)^+$: m/z=436.1. found: 435.9.

Example 1A, 1B, 1C, and 1D: 4-{3-chloro-6-ethoxy-2-fluoro-5-[1-([1,3]thiazolo[5,4-d]pyrimidin-7-ylamino)ethyl]phenyl}pyrrolidin-2-one (Four diastereoisomers)

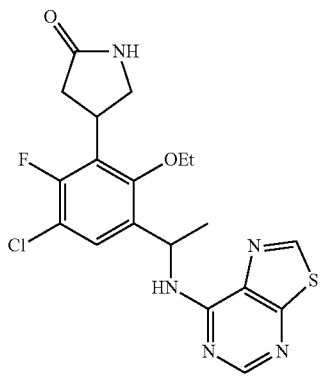 [SMILES: CCOc1c(C(C)Nc2ncnc3scnc23)cc(Cl)c(F)c1C1CNC(=O)C1]

The mixture of diastereoisomers of 4-{3-chloro-6-ethoxy-2-fluoro-5-[1-([1,3]thiazolo[5,4-d]pyrimidin-7-ylamino)ethyl]phenyl}pyrrolidin-2-one from Example 1 were separated by chiral HPLC (Phenomenex Lux Cellulose C-4, 5 micron, 21.2×250 mm, 35% ethanol in hexanes, 18 mL/min) to afford the individual diastereoisomers.

Example 1A (Peak 1): $^1$H NMR (300 MHz, DMSO-$d_6$) δ 9.29 (s, 1H), 8.75 (d, J=8.4 Hz, 1H), 8.36 (s, 1H), 7.82 (s, 1H), 7.71 (d, J=8.6 Hz, 1H), 5.88-5.70 (m, 1H), 4.30-4.13 (m, 1H), 4.12-3.96 (m, 1H), 3.95-3.82 (m, 1H), 3.58 (dd, J=9.4, 9.4 Hz, 1H), 3.30-3.19 (m, 1H), 2.64-2.52 (m, 1H), 2.32 (dd, J=18.2, 8.9 Hz, 1H), 1.57-1.34 (m, 6H); LCMS calculated for $C_{19}H_{20}ClFN_5O_2S$ (M+H)$^+$: m/z=436.1. found: 435.9.

Example 1B (Peak 2): $^1$H NMR (300 MHz, DMSO-$d_6$) δ 9.29 (s, 1H), 8.76 (d, J=8.6 Hz, 1H), 8.36 (s, 1H), 7.82 (s, 1H), 7.72 (d, J=8.6 Hz, 1H), 5.90-5.70 (m, 1H), 4.32-4.13 (m, 1H), 4.12-3.95 (m, 1H), 3.94-3.79 (m, 1H), 3.62 (dd, J=9.0, 9.0 Hz, 2H), 3.33-3.21 (m, 1H), 2.65-2.52 (m, 1H), 2.29 (dd, J=17.3, 7.9 Hz, 1H), 1.61-1.37 (m, 6H); LCMS calculated for $C_{19}H_{20}ClFN_5O_2S$ (M+H)$^+$: m/z=436.1. found: 435.9.

Example 1C (Peak 3): $^1$H NMR (300 MHz, DMSO-$d_6$) δ 9.29 (s, 1H), 8.76 (d, J=8.5 Hz, 1H), 8.36 (s, 1H), 7.82 (s, 1H), 7.72 (d, J=8.6 Hz, 1H), 5.89-5.71 (m, 1H), 4.30-4.15 (m, 1H), 4.12-3.95 (m, 1H), 3.93-3.79 (m, 1H), 3.62 (dd, J=9.6, 9.6 Hz, 1H), 3.30-3.21 (m, 1H), 2.63-2.51 (m, 1H), 2.29 (dd, J=16.5, 7.3 Hz, 1H), 1.58-1.35 (m, 6H); LCMS calculated for $C_{19}H_{20}ClFN_5O_2S$ (M+H)$^+$: m/z=436.1. found: 435.9.

Example 1D (Peak 4): $^1$H NMR (300 MHz, DMSO-$d_6$) δ 9.29 (s, 1H), 8.75 (d, J=8.5 Hz, 1H), 8.36 (s, 1H), 7.82 (s, 1H), 7.71 (d, J=8.6 Hz, 1H), 5.94-5.64 (m, 1H), 4.28-4.15 (m, 1H), 4.11-3.96 (m, 1H), 3.95-3.82 (m, 1H), 3.58 (dd, J=9.8, 9.8 Hz, 1H), 3.30-3.20 (m, 1H), 2.67-2.53 (m, 1H), 2.32 (dd, J=18.4, 8.9 Hz, 1H), 1.58-1.37 (m, 6H); LCMS calculated for $C_{19}H_{20}ClFN_5O_2S$ (M+H)$^+$: m/z=436.1. found: 435.9.

Example 2. 4-{3-Chloro-6-ethoxy-2-fluoro-5-[1-(pyrido[3,2-d]pyrimidin-4-ylamino)ethyl]phenyl}pyrrolidin-2-one

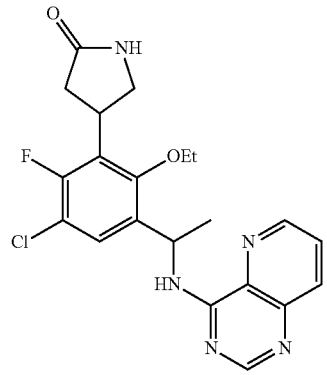 [SMILES: CCOc1c(C(C)Nc2ncnc3cccnc23)cc(Cl)c(F)c1C1CNC(=O)C1]

A suspension of 4-[3-(1-aminoethyl)-5-chloro-2-ethoxy-6-fluorophenyl]pyrrolidin-2-one (93.0 mg, 0.309 mmol) and 4-chloropyrido[3,2-c]pyrimidine (76.8 mg, 0.464 mmol) [093654, Oakwood Chemical] in 1-butanol (6.2 mL) was treated with N,N-diisopropylethylamine (0.162 mL, 0.928 mmol) and heated at 105° C. for 30 min. The reaction mixture was then concentrated to a yellow residue. Purification by flash column chromatography (100% DCM to 10% MeOH/DCM) afforded the crude product. Further purification by preparative LCMS (pH 10) afforded the title product (0.101 g, 76%) as a white solid as a mixture of four diastereoisomers. $^1$H NMR (300 MHz, DMSO-$d_6$) δ 8.93 (d, J=8.2 Hz, 1H), 8.85 (dd, J=4.2, 1.5 Hz, 1H), 8.45 (d, J=1.5 Hz, 1H), 8.16-8.07 (m, 1H), 7.90-7.73 (m, 3H), 5.90-5.69 (m, 1H), 4.32-4.15 (m, 1H), 4.12-3.96 (m, 1H), 3.96-3.80 (m, 1H), 3.60 (dd, J=10.7, 10.7 Hz, 1H), 3.29-3.21 (m, 1H), 2.63-2.55 (m, 1H), 2.39-2.21 (m, 1H), 1.52 (d, J=6.8 Hz, 3H), 1.45 (t, J=6.3 Hz, 3H); LCMS calculated for $C_{21}H_{22}ClFN_5O_2$ (M+H)$^+$: m/z=430.1. found: 429.9.

Example 2A, 2B, 2C, and 2D. 4-{3-chloro-6-ethoxy-2-fluoro-5-[1-(pyrido[3,2-d]pyrimidin-4-ylamino)ethyl]phenyl}pyrrolidin-2-one (Four diastereoisomers)

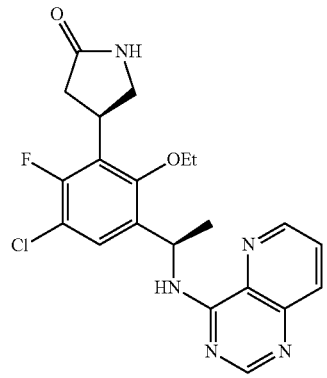

(R)-4-(3-chloro-6-ethoxy-2-fluoro-5-((R)-1-(pyrido[3,2-d]pyrimidin-4-ylamino)ethyl)phenyl)pyrrolidin-2-one The mixture of diastereoisomers of 4-{3-chloro-6-ethoxy-2-fluoro-5-[1-(pyrido[3,2-d]pyrimidin-4-ylamino)ethyl]phenyl}pyrrolidin-2-one were separated by chiral HPLC (Phenomenex Lux Cellulose C-4, 5 micron, 21.2×250 mm, 30% ethanol in hexanes, 18 mL/min) to afford the diastereoisomers of Examples 2A and 2B. The diastereoisomers of Examples 2C and 2D eluted together and were further purified by chiral HPLC (CHIRALPAK IA, 5 micron, 20×250 mm, 30% ethanol in hexanes, 12 mL/min) to yield individual diastereoisomers.

Example 2A (Peak 1): $^1$H NMR (300 MHz, DMSO-$d_6$) δ 8.93 (d, J=8.5 Hz, 1H), 8.85 (dd, J=4.2, 1.5 Hz, 1H), 8.45 (s, 1H), 8.11 (dd, J=8.5, 1.5 Hz, 1H), 7.90-7.74 (m, 3H), 5.87-5.74 (m, 1H), 4.30-4.16 (m, 1H), 4.12-3.96 (m, 1H), 3.96-3.82 (m, 1H), 3.58 (dd, J=9.6, 9.6 Hz, 1H), 3.30-3.18 (m, 1H), 2.65-2.54 (m, 1H), 2.33 (dd, J=17.4, 9.6 Hz, 1H), 1.52 (d, J=6.9 Hz, 3H), 1.45 (t, J=6.9 Hz, 3H); LCMS calculated for $C_{21}H_{22}ClFN_5O_2$ (M+H)$^+$: m/z=430.1. found: 430.0.

Example 2B (Peak 2): $^1$H NMR (300 MHz, DMSO-$d_6$) δ 8.93 (d, J=8.6 Hz, 1H), 8.85 (dd, J=4.2, 1.5 Hz, 1H), 8.44 (s, 1H), 8.11 (dd, J=8.5, 1.5 Hz, 1H), 7.90-7.73 (m, 3H), 5.88-5.75 (m, 1H), 4.32-4.16 (m, 1H), 4.13-3.96 (m, 1H), 3.94-3.80 (m, 1H), 3.62 (dd, J=9.2, 9.2 Hz, 1H), 3.31-3.24 (m, 1H), 2.62-2.52 (m, 1H), 2.30 (dd, J=17.0, 8.6 Hz, 1H), 1.52 (d, J=6.9 Hz, 3H), 1.45 (t, J=6.9 Hz, 3H); LCMS calculated for $C_{21}H_{22}ClFN_5O_2$ (M+H)$^+$: m/z=430.1. found: 429.9.

Example 2C (Peak 3)

$^1$H NMR (300 MHz, DMSO-$d_6$) δ 8.93 (d, J=8.6 Hz, 1H), 8.85 (dd, J=4.2, 1.5 Hz, 1H), 8.44 (s, 1H), 8.11 (dd, J=8.5, 1.5 Hz, 1H), 7.89-7.74 (m, 3H), 5.87-5.75 (m, 1H), 4.33-4.16 (m, 1H), 4.13-3.96 (m, 1H), 3.94-3.80 (m, 1H), 3.62 (dd, J=9.5, 9.5 Hz, 1H), 3.30-3.23 (m, 1H), 2.61-2.52 (m, 1H), 2.30 (dd, J=16.7, 8.7 Hz, 1H), 1.53 (d, J=6.9 Hz, 3H), 1.45 (t, J=6.9 Hz, 3H); LCMS calculated for $C_{21}H_{22}ClFN_5O_2$ (M+H)$^+$: m/z=430.1. found: 429.9.

Example 2D (Peak 4)

$^1$H NMR (300 MHz, DMSO-$d_6$) δ 8.93 (d, J=8.6 Hz, 1H), 8.85 (dd, J=4.2, 1.5 Hz, 1H), 8.45 (s, 1H), 8.11 (dd, J=8.5, 1.5 Hz, 1H), 7.88-7.74 (m, 3H), 5.87-5.74 (m, 1H), 4.30-4.15 (m, 1H), 4.12-3.96 (m, 1H), 3.96-3.83 (m, 1H), 3.59 (dd, J=9.2, 9.2 Hz, 1H), 3.31-3.21 (m, 1H), 2.65-2.54 (m, 1H), 2.33 (dd, J=16.6, 8.8 Hz, 1H), 1.52 (d, J=6.9 Hz, 3H), 1.45 (t, J=6.9 Hz, 3H); LCMS calculated for $C_{21}H_{22}ClFN_5O_2$ (M+H)$^+$: m/z=430.1. found: 429.9.

Example 3. 5-{3-Chloro-6-methoxy-2-methyl-5-[(1S)-1-(pyrido[3,2-d]pyrimidin-4-ylamino)ethyl]phenyl}-N,N-dimethylpyridine-2-carboxamide bis (trifluoroacetate)

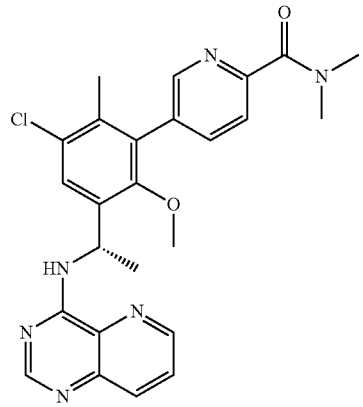 [SMILES: COc1c([C@H](C)Nc2ncnc3cccnc23)cc(Cl)c(C)c1-c1ccc(C(=O)N(C)C)nc1]

Step 1. tert-Butyl {(1S)-1-[5-chloro-3-(6-cyanopyridin-3-yl)-2-methoxy-4-methylphenyl]ethyl}carbamate

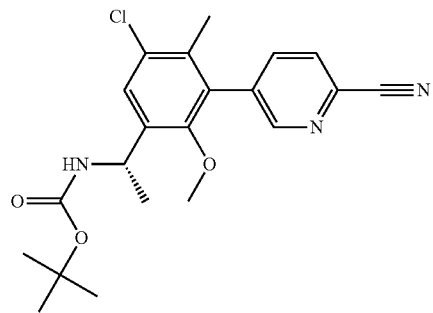 [SMILES: COc1c([C@H](C)NC(=O)OC(C)(C)C)cc(Cl)c(C)c1-c1ccc(C#N)nc1]

A mixture of tert-butyl[(1S)-1-(3-bromo-5-chloro-2-methoxy-4-methylphenyl)ethyl]carbamate (0.31 g, 0.82 mmol), 5-(4,4,5,5-tetramethyl-1,3,2-dioxaborolan-2-yl)pyridine-2-carbonitrile (0.24 g, 1.1 mmol), and [1,1'-bis(diphenylphosphino)ferrocene]dichloropalladium(II), complex with dichloromethane (1:1) (0.13 g, 0.16 mmol) in acetonitrile (3.7 mL) was purged with $N_2$ and then stirred at 95° C. for 2 h. The mixture was then diluted with ethyl acetate and washed with water. The organic layer was dried over $MgSO_4$, concentrated, and purified by silica gel (eluting with 0-30% EtOAc/hexanes) to afford the desired product (0.3 g, 91%). LCMS calculated for $C_{21}H_{25}ClN_3O_3$ (M+H)$^+$: m/z=402.2. found: 402.1.

Step 2. 5-(3-{(1S)-1-[(tert-Butoxycarbonyl)amino]ethyl}-5-chloro-2-methoxy-6-methylphenyl)pyridine-2-carboxylic acid

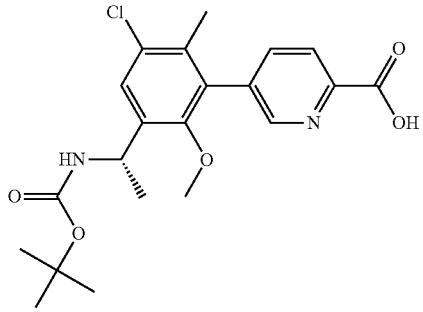 [SMILES: COc1c([C@H](C)NC(=O)OC(C)(C)C)cc(Cl)c(C)c1-c1ccc(C(=O)O)nc1]

A mixture of tert-butyl {(1S)-1-[5-chloro-3-(6-cyanopyridin-3-yl)-2-methoxy-4-methylphenyl]ethyl}carbamate (0.30 g, 0.75 mmol) and 1.0 M sodium hydroxide in water (3.7 mL, 3.7 mmol) in ethanol (3.7 mL) was heated at 90° C. for 6 h in a sealed tube. The mixture was then concentrated to remove ethanol. The resulting residue was cooled to 0° C., acidified with 1N HCl to pH=3, and then extracted with ethyl acetate. The combined extracts were dried over MgSO$_4$ and concentrated to afford the desired product (0.27 g, 86%). LCMS calculated for C$_{21}$H$_{26}$ClN$_2$O$_5$ (M+H)$^+$: m/z=421.2. found: 421.1.

Step 3. tert-Butyl[(1S)-1-(5-chloro-3-{6-[(dimethylamino)carbonyl]pyridin-3-yl}-2-methoxy-4-methylphenyl)ethyl]carbamate

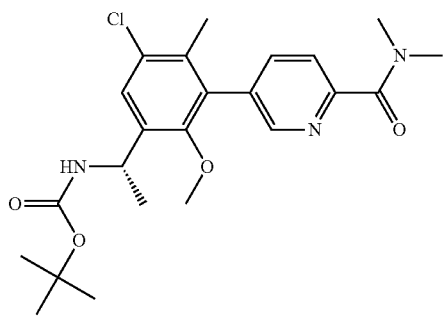 [SMILES: COc1c([C@H](C)NC(=O)OC(C)(C)C)cc(Cl)c(C)c1-c1ccc(C(=O)N(C)C)nc1]

To a solution of 5-(3-{(1S)-1-[(tert-butoxycarbonyl)amino]ethyl}-5-chloro-2-methoxy-6-methylphenyl)pyridine-2-carboxylic acid (80 mg, 0.2 mmol), dimethylamine hydrochloride (18 mg, 0.22 mmol) and benzotriazol-1-yloxytris(dimethylamino)phosphonium hexafluorophosphate (100 mg, 0.23 mmol) in N,N-dimethylformamide (1 mL) was added N,N-diisopropylethylamine (0.099 mL, 0.57 mmol). The mixture was stirred at room temperature for 2 h then diluted with water. The resulting mixture was extracted with ethyl acetate and the combined organic layers were dried over MgSO$_4$, filtered, and concentrated. The resulting residue was purified on silica gel (eluting with 0-40% EtOAc/dichloromethane) to afford the desired product.

Step 4. 5-{3-[(1S)-1-Aminoethyl]-5-chloro-2-methoxy-6-methylphenyl}-N,N-dimethylpyridine-2-carboxamide dihydrochloride

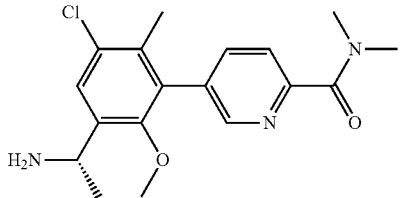 [SMILES: COc1c([C@H](C)N)cc(Cl)c(C)c1-c1ccc(C(=O)N(C)C)nc1]

A mixture of tert-butyl[(1S)-1-(5-chloro-3-{6-[(dimethylamino)carbonyl]pyridin-3-yl}-2-methoxy-4-methylphenyl)ethyl]carbamate (0.34 g, 0.76 mmol) in methylene chloride (0.5 mL) was treated with 4.0 M hydrogen chloride in dioxane (1.5 mL) at room temperature for 2 h and then concentrated to dryness to afford the desired product which was used directly in the next step. LCMS calculated for C$_{18}$H$_{23}$ClN$_3$O$_2$ (M+H)$^+$: m/z=348.1. found: 348.1.

Step 5. 5-{3-Chloro-6-methoxy-2-methyl-5[(1S)-1-(pyrido[3,2-d]pyrimidin-4-ylamino)ethyl]phenyl}-N,N-dimethylpyridine-2-carboxamide bis(trifluoroacetate)

A mixture of 5-{3-[(1S)-1-aminoethyl]-5-chloro-2-methoxy-6-methylphenyl}-N,N-dimethylpyridine-2-carboxamide dihydrochloride (17 mg, 0.040 mmol), 4-chloropyrido[3,2-d]pyrimidine (6.7 mg, 0.040 mmol) and N,N-diisopropylethylamine (35 µL, 0.20 mmol) in 1-butanol (0.4 mL) was heated at 120° C. for 2 h. The mixture was purified on prep-LCMS (Sunfire Prep C18 5 µm 30×10 mm column, flow rate 60 mL/min, eluting with a gradient of acetonitrile and water with 0.05% TFA) to afford the title product (2.7 mg, 14%). LCMS calculated for C$_{25}$H$_{26}$ClN$_6$O$_2$ (M+H)$^+$: m/z=477.2. found: 477.2.

Example 4. 4-Chloro-N-ethyl-3',5'-difluoro-3-methyl-6-[1-(pyrido[3,2-d]pyrimidin-4-ylamino)ethyl]biphenyl-2-carboxamide

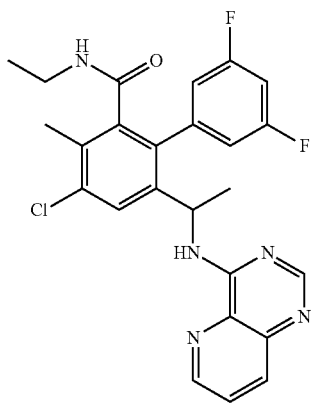 [SMILES: CCNC(=O)c1c(C)c(Cl)cc(C(C)Nc2ncnc3cccnc23)c1-c1cc(F)cc(F)c1]

Step 1. 3-Acetyl-5-chloro-2-hydroxy-6-methylbenzonitrile

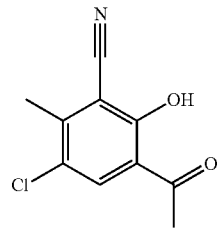

A mixture of 1-(3-bromo-5-chloro-2-hydroxy-4-methylphenyl)ethanone (4.85 g, 18.4 mmol) and copper cyanide (2.47 g, 27.6 mmol) in N-methylpyrrolidinone (15 mL) was heated at 200° C. for 1 h. After cooling to room temperature, the mixture was diluted with ethyl acetate and 1 N HCl. The layers were separated and the aqueous layer was extracted with ethyl acetate. The combined organic layers were washed with water, brine, dried over magnesium sulfate, then filtered and concentrated to dry under reduced pressure. The residue (3.7 g, 96%) was used directly in the next step without further purification. LCMS calculated for $C_{10}H_9ClNO_2$ (M+H)$^+$: m/z=210.0. found: 210.1.

Step 2. 6-Acetyl-4-chloro-2-cyano-3-methylphenyl trifluoromethanesulfonate

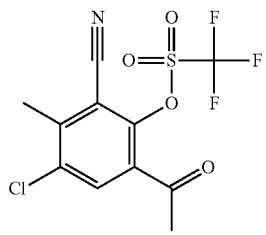 [SMILES: CC(=O)c1cc(Cl)c(C)c(C#N)c1OS(=O)(=O)C(F)(F)F]

To a mixture of 3-acetyl-5-chloro-2-hydroxy-6-methylbenzonitrile (3.70 g, 17.6 mmol) in methylene chloride (70 mL) was added triethylamine (7.4 mL, 53 mmol) followed by trifluoromethanesulfonic anhydride (4.4 mL, 26 mmol) at −78° C. The reaction mixture was gradually warmed to room temperature and stirred at room temperature for 30 min. After quenching with water, the mixture was extracted with dichloromethane. The combined organic layers were washed with brine, dried over sodium sulfate, filtered, and concentrated to dryness. The residue was purified on silica gel (eluting with 0 to 40% EtOAc in hexanes) to afford the desired product (2.54 g, 42%). LCMS calculated for $C_{11}H_8ClF_3NO_4S$ (M+H)$^+$: m/z=342.0. found: 342.1.

Step 3. 6-Acetyl-4-chloro-3',5'-difluoro-3-methylbiphenyl-2-carbonitrile

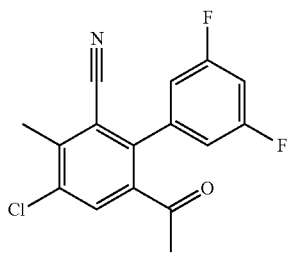 [SMILES: CC(=O)c1cc(Cl)c(C)c(C#N)c1-c1cc(F)cc(F)c1]

A biphasic solution of 6-acetyl-4-chloro-2-cyano-3-methylphenyl trifluoromethanesulfonate (4.51 g, 13.2 mmol) and (3,5-difluorophenyl)boronic acid (2.50 g, 15.8 mmol) in toluene (50 mL)/0.8 M sodium hydrogencarbonate in water (50 mL, 40 mmol) was degassed with $N_2$. Tetrakis(triphenylphosphine)palladium(0) (0.609 g, 0.527 mmol) was then added. The mixture was bubbled with $N_2$ for 5 min and then heated at 80° C. for 2 h. After cooling to room temperature, the mixture was diluted with ethyl acetate. The layers were separated and the aqueous layer was extracted with ethyl acetate. The combined extracts were washed with brine, dried over $Na_2SO_4$, filtered, and concentrated to a crude dark solid. This material was then dissolved in $CHCl_3$ and purified on a silica gel column (eluting with 0-30% ethyl acetate/hexanes) to afford the desired product (1.94 g, 48%). LCMS calculated for $C_{16}H_{11}ClF_2NO$ (M+H)$^+$: m/z=306.0. found: 306.0.

Step 4. 4-Chloro-3',5'-difluoro-6-(1-hydroxyethyl)-3-methylbiphenyl-2-carbaldehyde

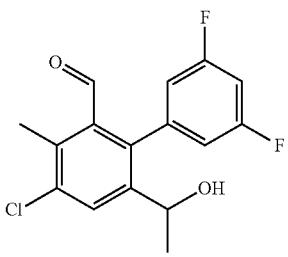 [SMILES: Cc1c(Cl)cc(C(C)O)c(-c2cc(F)cc(F)c2)c1C=O]

To a mixture of 6-acetyl-4-chloro-3',5'-difluoro-3-methylbiphenyl-2-carbonitrile (2.43 g, 7.95 mmol) in methylene chloride (50 mL) was added 1.0 M diisobutylaluminum hydride in hexane (19.9 mL, 19.9 mmol) at −78° C. The reaction mixture was warmed to room temperature over 2 h with stirring. 5.0 M Hydrogen chloride in water (70 mL, 400 mmol) was then added slowly and stirring was continued for 1 h. The resultant mixture was extracted with ethyl acetate. The combined organic layers were washed with brine, dried over sodium sulfate, filtered, and concentrated to dryness. The residue was purified on silica gel (eluting with 0 to 50% ethyl acetate in hexanes) to afford the desired product (2.4 g, 97%). LCMS calculated for $C_{16}H_{12}ClF_2O$ (M−OH)$^+$: m/z=293.1. found: 293.1.

Step 5. 4-Chloro-3',5'-difluoro-6-(1-hydroxyethyl)-3-methylbiphenyl-2-carboxylic acid

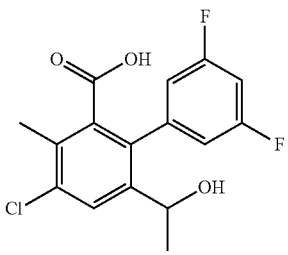 [SMILES: Cc1c(Cl)cc(C(C)O)c(-c2cc(F)cc(F)c2)c1C(=O)O]

To a solution of 4-chloro-3',5'-difluoro-6-(1-hydroxyethyl)-3-methylbiphenyl-2-carbaldehyde (1.00 g, 3.22 mmol) in methanol (40 mL) was added 1.0 M sodium hydroxide in water (16 mL, 16 mmol), followed by urea hydrogen peroxide (CAS #124-43-6 purchased from Sigma-Aldrich, 1.00 g, 10.6 mmol). After stirring overnight at room temperature, the mixture was slowly acidified to pH 5 with 1 N HCl then extracted with ethyl acetate. The combined organic layers were washed with brine, dried over magnesium sulfate, filtered, and concentrated to dryness under reduced pressure. The crude residue (1.05 g, 99.8%) was used directly in the next step.

Step 6. 4-Chloro-N-ethyl-3',5'-difluoro-6-(1-hydroxyethyl)-3-methylbiphenyl-2-carboxamide

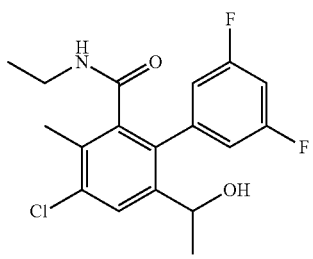 [SMILES: CCNC(=O)c1c(C)c(Cl)cc(C(C)O)c1-c1cc(F)cc(F)c1]

A mixture of 4-chloro-3',5'-difluoro-6-(1-hydroxyethyl)-3-methylbiphenyl-2-carboxylic acid (250 mg, 0.76 mmol), ethylamine hydrochloride (94 mg, 1.1 mmol) and benzotriazol-1-yloxytris(dimethylamino)phosphonium hexafluorophosphate (0.51 g, 1.1 mmol) in N,N-dimethylformamide (4 mL) was stirred at room temperature for 10 min. To the resulting mixture was added N,N-diisopropylethylamine (0.40 mL, 2.3 mmol). After stirring overnight at room temperature, the reaction mixture was quenched with water and extracted with ethyl acetate. The combined organic layers were washed with water and brine, dried over magnesium sulfate, filtered, and concentrated to dryness. The residue was purified on silica gel (eluting with 0 to 80% ethyl acetate in hexanes) to afford the desired product (0.185 g, 68%). LCMS calculated for $C_{18}H_{19}ClF_2NO_2$ $(M+H)^+$: m/z=354.1. found: 354.0.

Step 7. 1-{4-Chloro-6-[(ethylamino)carbonyl]-3',5'-difluoro-5-methylbiphenyl-2-yl}ethyl methanesulfonate

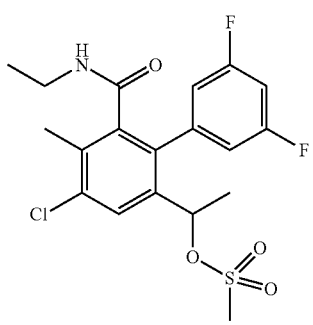 [SMILES: CCNC(=O)c1c(C)c(Cl)cc(C(C)OS(C)(=O)=O)c1-c1cc(F)cc(F)c1]

To a mixture of 4-chloro-N-ethyl-3',5'-difluoro-6-(1-hydroxyethyl)-3-methylbiphenyl-2-carboxamide (185 mg, 0.523 mmol) in methylene chloride (3 mL) was added N,N-diisopropylethylamine (0.18 mL, 1.0 mmol), followed by methanesulfonyl chloride (0.061 mL, 0.78 mmol). The reaction was stirred at room temperature for 10 min, quenched by pouring over ice water, and then extracted with dichloromethane. The combined organic layers were washed with aqueous sodium bicarbonate, dried over magnesium sulfate, filtered, and evaporated to dryness. The resulting residue (0.226 g, 100%) was used directly in the next step without further purification. LCMS calculated for $C_{19}H_{21}ClF_2NO_4S$ $(M+H)^+$: m/z=432.1. found: 432.1.

Step 8. 6-(1-Azidoethyl)-4-chloro-N-ethyl-3',5'-difluoro-3-methylbiphenyl-2-carboxamide

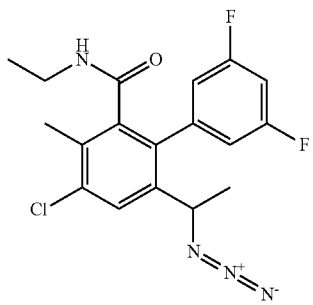 [SMILES: CCNC(=O)c1c(C)c(Cl)cc(C(C)N=[N+]=[N-])c1-c1cc(F)cc(F)c1]

To a mixture of 1-{4-chloro-6-[(ethylamino)carbonyl]-3',5'-difluoro-5-methylbiphenyl-2-yl}ethyl methanesulfonate (390 mg, 0.90 mmol) in N,N-dimethylformamide (5 mL) was added sodium azide (290 mg, 4.5 mmol). The reaction was stirred overnight at room temperature, then quenched with water and extracted with ethyl acetate. The combined organic layers were washed with water and brine, dried over magnesium sulfate, filtered, and concentrated to dryness. The crude residue (0.34 g, 99%) was used directly in the next step without further purification. LCMS calculated for $C_{18}H_{18}ClF_2N_4O$ $(M+H)^+$: m/z=379.1. found: 379.0.

Step 9. 6-(1-Aminoethyl)-4-chloro-N-ethyl-3',5'-difluoro-3-methylbiphenyl-2-carboxamide

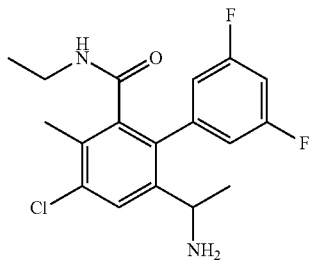 [SMILES: CCNC(=O)c1c(C)c(Cl)cc(C(C)N)c1-c1cc(F)cc(F)c1]

To a stirred mixture of 6-(1-azidoethyl)-4-chloro-N-ethyl-3',5'-difluoro-3-methylbiphenyl-2-carboxamide (0.34 g, 0.90 mmol) in tetrahydrofuran (6 mL) and water (1 mL) was added 1.0 M trimethylphosphine in THF (1.1 mL, 1.1 mmol). The mixture was then stirred at room temperature for 1 h. After nitrogen was passed through the mixture, the reaction mixture was extracted with dichloromethane. The extracts were washed with brine, dried over magnesium sulfate, filtered, and evaporated to dryness. The crude residue (0.135 g, 43%) was used directly in the next step without further purification. LCMS calculated for $C_{18}H_{20}ClF_2N_2O$ $(M+H)^+$: m/z=353.1. found: 353.1.

Step 10. 4-Chloro-N-ethyl-3',5'-difluoro-3-methyl-6-[1-(pyrido[3,2-d]pyrimidin-4-ylamino)ethyl]biphenyl-2-carboxamide A mixture of 6-(1-aminoethyl)-4-chloro-N-ethyl-3',5'-difluoro-3-methylbiphenyl-2-carboxamide (30 mg, 0.08 mmol), 4-chloropyrido[3,2-d]pyrimidine (30 mg, 0.2 mmol) and N,N-diisopropylethylamine (0.04 mL, 0.2 mmol) in 1-butanol (0.5 mL) was heated at 100° C. overnight. After evaporating to dryness, the residue was purified on RP-HPLC (Sunfire Prep C18 5 μm 30×10 mm column, flow rate 60 mL/min, eluting with a gradient of MeCN and water with 0.1% ammonium hydroxide) to afford the desired product. LCMS calculated for $C_{25}H_{23}ClF_2N_5O(M+H)^+$: m/z=482.2. found: 482.1.

Example J1. ((2R,5S)-5-{2-[(1R)-1-Hydroxyethyl]-1H-imidazo[4,5-d]thieno[3,2-b]pyridin-1-yl}tetrahydro-2H-pyran-2-yl)acetonitrile

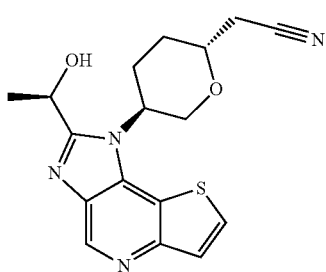 [SMILES: C[C@@H](O)c1nc2cnc3ccsc3c2n1[C@H]1CC[C@H](CC#N)OC1]

Step 1. tert-Butyl(4S)-2,2-dimethyl-4-vinyl-1,3-oxazolidine-3-carboxylate

To a suspension of methyl triphenylphosphonium bromide (5.63 g, 15.8 mmol) in tetrahydrofuran (140 mL) was added 2.5 M n-butyllithium in hexane (7.35 mL, 18.4 mmol). The deep red solution was stirred at 0° C. for 1 h. Then a solution of tert-butyl(4R)-4-formyl-2,2-dimethyl-1,3-oxazolidine-3-carboxylate (from Aldrich, 3.01 g, 13.1 mmol) in tetrahydrofuran (7.3 mL) was added drop wise at 0° C. The red solution was warmed to room temperature and stirred for 12 h. Hexanes was added to the reaction mixture in 4:1 (v/v) ratio. The suspension was filtered through Celite and the filtrate concentrated. The resultant residue was purified by flash chromatography (eluting with 10% ethyl acetate in hexanes) to give the desired compound as colorless oil (1.92 g, 64%).

Step 2. tert-Butyl[(1S)-1-(hydroxymethyl)prop-2-en-1-yl]carbamate

To a solution of tert-butyl(4S)-2,2-dimethyl-4-vinyl-1,3-oxazolidine-3-carboxylate (1.90 g, 8.36 mmol) in methanol (83 mL) was added p-toluenesulfonic acid monohydrate (0.80 g, 4.2 mmol) at 0° C. The mixture was slowly warmed to room temperature overnight. The reaction mixture was diluted with saturated $NaHCO_3$ solution, concentrated, and then diluted with ethyl acetate. The organic layer was washed with sat. $NaHCO_3$ (2×) and brine, dried over $Na_2SO_4$, filtered and concentrated to give the desired product as colorless oil (1.187 g, 76%). $^1H$ NMR (400 MHz, $CDCl_3$) δ 5.81 (1H, m), 5.25 (2H, m), 4.90 (1H, m), 4.25 (1H, br s), 3.67 (2H, m), 1.45 (9H, s) ppm.

Step 3. tert-Butyl[(1S)-1-({[1-(hydroxymethyl)prop-2-en-1-yl]oxy}methyl)prop-2-en-1-yl]carbamate To a flask was charged with tert-butyl[(1S)-1-(hydroxymethyl)prop-2-en-1-yl]carbamate (0.401 g, 2.14 mmol), tris(dibenzylideneacetone)dipalladium(0) (59 mg, 0.064 mmol), N,N'-(1S,2S)-cyclohexane-1,2-diylbis[2-(diphenylphosphino)-1-naphthamide] (150 mg, 0.19 mmol), and 4-dimethylaminopyridine (78 mg, 0.64 mmol). The reaction mixture was purged with $N_2$ three times, and then methylene chloride (21.3 mL), and 1.0 M triethylborane in THF (130 μL, 0.13 mmol) was added sequentially. After stirring for 10 min, 2-vinyloxirane (0.150 g, 2.14 mmol) was added and the resulting mixture was stirred overnight. The reaction was diluted with dichloromethane and sat. $NaHCO_3$ solution. The organic layer was separated and dried over $Na_2SO_4$, filtered and concentrated. The crude residue was purified with flash chromatography (eluting with 0-50% ethyl acetate/hexanes) to give the desired product (0.271 g, 49%). $^1H$ NMR (300 MHz, $CDCl_3$) δ 5.85 (1H, m), 5.67 (1H, m), 5.845.17 (4H, m), 4.83 (1H, m), 4.30 (1H, br s), 3.83 (1H, m), 3.69 (1H, dd, J=4.5 and 6.9 Hz), 3.54 (2H, m), 3.36 (1H, dd, J=4.5 and 6.9 Hz), 1.45 (9H, s) ppm.

Step 4. 2-({(2S)-2-[(tert-Butoxycarbonyl)amino]but-3-en-1-yl}oxy)but-3-en-1-yl acetate To a mixture of tert-butyl[(1S)-1-({[1-(hydroxymethyl)prop-2-en-1-yl]oxy}methyl)prop-2-en-1-yl]carbamate (268 mg, 1.04 mmol) in methylene chloride (10 mL) was added with triethylamine (435 μL, 3.12 mmol). The mixture was cooled to 0° C., and acetyl chloride (150 μL, 2.1 mmol) was added drop wise. The reaction was stirred at room temperature for 2 h, then quenched with water. The organic layer was concentrated and the resultant residue purified on silica gel (eluting with 20% ethyl acetate/hexanes) to give the desired product (0.26 g, 85%). LCMS calculated for $C_{10}H_{18}NO_3$ $(M-100+H)^+$: m/z=200.1. Found: 200.1.

Step 5. {(5S)-5-[(tert-Butoxycarbonyl)amino]-5,6-dihydro-2H-pyran-2-yl}methyl acetate To a 500 mL 2-neck round bottom flask, benzylidene(dichloro)(1,3-dimesitylimidazolidin-2-id-2-yl)(tricyclohexylphosphoranyl)ruthenium (38 mg, 0.044 mmol) was added. After purged with nitrogen for 3 times, dichloromethane (anhydrous, 8 mL) was added followed by 2-({(2S)-2-[(tert-butoxycarbonyl)amino]but-3-en-1-yl}oxy)but-3-en-1-yl acetate (265 mg, 0.885 mmol). The reaction mixture was stirred at room temperature for 15 h. The mixture was concentrated in vacuo. The residue was purified via flash chromatography (eluting with hexanes to 25% EtOAc in hexanes) to give the desired product as a brown oil (0.205 g, 85%). LCMS calculated for $C_9H_{14}NO_5$ $(M+H-Bu+H)^+$: m/z=216.1. Found: 216.1. $^1H$ NMR (300 MHz, $CDCl_3$) δ 5.94 (0.17H, m), 5.84 (0.83H, m), 5.69 (1H, m), 4.89 (0.13H, m), 4.70 (0.83H, m), 4.25 (1H, m), 4.05 (4H, m), 3.56 (0.13H, m), 3.38 (0.87H, m), 2.04 (2.49H, s), 2.03 (0.51H, m), 1.38 (9H, s) ppm (The product was a 5:1 mixture of trans- and cis-isomers).

Step 6. [(5S)-5-Amino-5,6-dihydro-2H-pyran-2-yl]methyl acetate

To a solution of {(5S)-5-[(tert-butoxycarbonyl)amino]-5,6-dihydro-2H-pyran-2-yl}methyl acetate (205 mg, 0.756 mmol) in methylene chloride (5.2 mL) was added 4.0 M hydrogen chloride in dioxane (1.5 mL, 6.0 mmol). The reaction solution was stirred at room temperature for 6 h. The solvent was removed under reduced pressure to give the desired product as white solid. LCMS calculated for $C_8H_{14}NO_3$ (M+H)$^+$: m/z=172.1. Found: 172.1.

Step 7. {(5S)-5-[(6-Nitrothieno[3,2-b]pyridin-7-yl)amino]-5,6-dihydro-2H-pyran-2-yl}methyl acetate A mixture of 7-chloro-6-nitrothieno[3,2-b]pyridine (156 mg, 0.727 mmol), [(5S)-5-amino-5,6-dihydro-2H-pyran-2-yl]methyl acetate (129 mg, 0.754 mmol) and N,N-diisopropylethylamine (0.26 mL, 1.5 mmol) in isopropyl alcohol (1.7 mL) was heated at 90° C. for 2 h. The reaction mixture was concentrated and purified with flash chromatography to give the desired product (0.21 g 83%). LCMS calculated for $C_{15}H_{16}N_3O_5S$ (M+H)$^+$: m/z=350.1. Found: 350.0.

Step 8. {(5S)-5-[(6-Aminothieno[3,2-b]pyridin-7-yl)amino]tetrahydro-2H-pyran-2-yl}methyl acetate A mixture of {(5S)-5-[(6-nitrothieno[3,2-b]pyridin-7-yl)amino]-5,6-dihydro-2H-pyran-2-yl}methyl acetate (210 mg, 0.600 mmol) and 10% palladium on carbon (0.21 g) in methanol (4.0 mL) was subjected to balloon pressure of $H_2$ at room temperature for 2 h. The mixture was filtered, and the filtrate was concentrated and purified with flash chromatography (eluting with 15% methanol in dichloromethane) to give the desired product (145 mg, 75%). LCMS calculated for $C_{15}H_{20}N_3O_3S$ (M+H)$^+$: m/z=322.1. Found: 322.0.

Step 9. (1R)-1-{1-[(3S)-6-(Hydroxymethyl)tetrahydro-2H-pyran-3-yl]-1H-imidazo[4,5-d]thieno[3,2-b]pyridin-2-yl}ethanol A mixture of (2R)-2-hydroxypropanamide (131 mg, 1.47 mmol) and triethyloxonium tetrafluoroborate (263 mg, 1.38 mmol) in THF (2 mL) was stirred at room temperature for 2 h. The solvent was removed and the residue dissolved in ethanol (0.85 mL) and added to a suspension of {(5S)-5-[(6-aminothieno[3,2-b]pyridin-7-yl)amino]tetrahydro-2H-pyran-2-yl}methyl acetate (145 mg, 0.451 mmol) in ethanol (3.1 mL). The mixture was stirred at 80° C. for 1 h. The reaction was cooled to room temperature and diluted with water (1.0 mL). Lithium hydroxide (32.4 mg, 1.35 mmol) was added, and the mixture was stirred for 2 h. The reaction mixture was diluted with methanol and purified with prep-LCMS (XBridge C18 column, eluting with a gradient of acetonitrile/water containing 0.1% ammonium hydroxide, at flow rate of 60 mL/min) to give the desired product as white solid (95 mg, 63%). LCMS calculated for $C_{16}H_{20}N_3O_3S$ (M+H)$^+$: m/z=334.1. Found: 334.0.

Step 10: ((2R,5S)-5-{2-[(1R)-1-Hydroxyethy]-M-imidazo[4,5-d]thieno[3,2-b]pyridin-1-yl}tetrahydro-2H-pyran-2-yl)methyl 4-methylbenzenesulfonate and ((2S,5S)-5-{2-[(1R)-1-hydroxyethyl]-M-imidazo[4,5-d]thieno[3,2-b]pyridin-1-yl}tetrahydro-2H-pyran-2-yl)methyl 4-methylbenzenesulfonate To a solution of (1R)-1-{1-[(3S)-6-(hydroxymethyl)tetrahydro-2H-pyran-3-yl]-1H-imidazo[4,5-d]thieno[3,2-b]pyridin-2-yl}ethanol (100 mg, 0.300 mmol) (previous step) in methylene chloride (3.4 mL) and pyridine (0.146 mL, 1.80 mmol) was added p-toluenesulfonyl chloride (57.2 mg, 0.300 mmol) and 4-dimethylaminopyridine (1.8 mg, 0.015 mmol) at 0° C. The reaction mixture was allowed to warm to room temperature overnight. The reaction mixture was concentrated, diluted with methanol, and purified with prep-LCMS (XBridge C18 column, eluting with a gradient of acetonitrile/water containing 0.1% ammonium hydroxide, at flow rate of 60 mL/min) to give two peaks. On analytic HPLC (Waters SunFire $C_{18}$, 2.1×50 mm, 5 µM; Flow rate 3 mL/min; Injection volume 2 µL; At gradient from 2 to 80% B in 3 minutes (A=water with 0.025% TFA, B=acetonitrile)): First peak (45.3 mg, 31%) retention time 1.81 min, LCMS calculated for $C_{23}H_{26}N_3O_5S_2$ (M+H)$^+$: m/z=488.1. Found: 488.1. Second peak (8.5 mg, 5.8%) retention time 1.88 min, LCMS calculated for $C_{23}H_{26}N_3O_5S_2$ (M+H)$^+$: m/z=488.1. Found: 488.1.

Step 11. ((2R,5S)-5-{2-[(1R)-1-Hydroxyethyl]-1H-imidazo[4,5-d]thieno[3,2-b]pyridin-1-yl}tetrahydro-2H-pyran-2-yl)acetonitrile A mixture of ((2R,5S)-5-{2-[(1R)-1-hydroxyethyl]-1H-imidazo[4,5-d]thieno[3,2-b]pyridin-1-yl}tetrahydro-2H-pyran-2-yl)methyl 4-methylbenzenesulfonate (from 1st peak of previous step, 27 mg, 0.055 mmol) and sodium cyanide (4.5 mg, 0.092 mmol) in dimethyl sulfoxide (0.4 mL) was stirred at 50° C. for 4 h. After cooling, the mixture was diluted with methanol and purified with prep-LCMS (XBridge C18 column, eluting with a gradient of acetonitrile/water containing 0.1% ammonium hydroxide, at flow rate of 30 mL/min) to give the desired product (14.5 mg, 76%). LCMS calculated for $C_{17}H_{19}N_4O_2S$ (M+H)$^+$: m/z=343.1. Found: 343.0. $^1$H NMR (DMSO-$d_6$, 500 MHz) δ 9.51 (1H, s), 8.45 (1H, d, J=5.5 Hz), 7.97 (1H, d, J=5.5 Hz), 5.31 (1H, m), 5.20 (1H, m), 4.31 (1H, m), 4.23 (1H, m), 4.02 (1H, m), 2.96 (1H, dd, J=17.0 and 4.5 Hz), 2.85 (1H, dd, J=17.0 and 4.5 Hz), 2.66 (1H, m), 2.26 (1H, m), 2.09 (1H, m), 1.73 (1H, m), 1.69 (3H, d, J=6.5 Hz) ppm.

Example J1a. ((2R,5S)-5-{2-[(1R)-1-Hydroxyethyl]-1H-imidazo[4,5-d]thieno[3,2-b]pyridin-1-yl}tetrahydro-2H-pyran-2-yl)acetonitrile hydrate

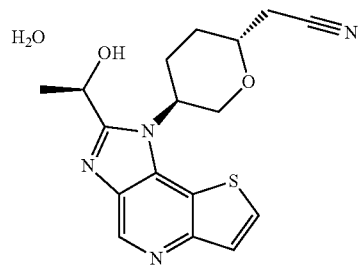

((2R,5S)-5-{2-[(1R)-1-Hydroxyethyl]-1H-imidazo[4,5-d]thieno[3,2-b]pyridin-1-yl}tetrahydro-2H-pyran-2-yl)acetonitrile (52 mg, 0.15 mmol) from Example 25 was crystallized from a mixture of acetonitrile (8 mL) and water (4 mL). The resulting colorless prism crystal collected was suitable for X-ray crystal structure analysis.

Crystal data shows: ~0.520×0.180×0.100 mm, orthorhombic, P212121, a=6.962(3) Å, b=11.531(4) Å, c=20.799(7) Å, Vol=1669.6(10) Å$^3$, Z=4, T=−100.° C., Formula weight=359.42, Density=1.430 g/cm$^3$, µ(Mo)=0.22 mm$^{-1}$.

Data collection was done on a Bruker SMART APEX-II CCD system, MoKalpha radiation, standard focus tube, anode power=50 kV×42 mA, crystal to plate distance=5.0 cm, 512×512 pixels/frame, beam center=(256.13, 253.14), total frames=1151, oscillation/frame=0.50°, exposure/frame=10.1 sec/frame, SAINT integration, hid min/max=(−9, 9, −15, 15, −27, 27), data input to shelx=17025, unique data=3975, two-theta range=3.92 to 55.72°, completeness to two-theta 55.72=99.80%, R(int-xl)=0.0681, SADABS correction applied.

Structure was solved using XS(Shelxtl), refined using shelxtl software package, refinement by full-matrix least squares on $F^2$, scattering factors from Int. Tab. Vol C Tables 4.2.6.8 and 6.1.1.4, number of data=3975, number of restraints=0, number of parameters=235, data/parameter ratio=16.91, goodness-of-fit on $F^2$=1.04, R indices [I>4sigma(I)] R1=0.0505, wR2=0.1242, R indices(all data) R1=0.0769, wR2=0.1401, max difference peak and hole=0.724 and −0.277 e/Å$^3$, refined flack parameter=−0.12 (13), All of the CH hydrogen atoms were refined using a riding model. The OH hydrogens were found from a difference map and fully refined.

Results showed that the asymmetric unit contains one molecule and one water as shown with thermal ellipsoids drawn to the 50% probability level. The stereochemistry at each of three stereo centers (as indicated in the name and structure of the compound above) was confirmed. The flack parameter refined to 0.28(24) indicating the correct enantiomeric setting.

Example J2. 4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide

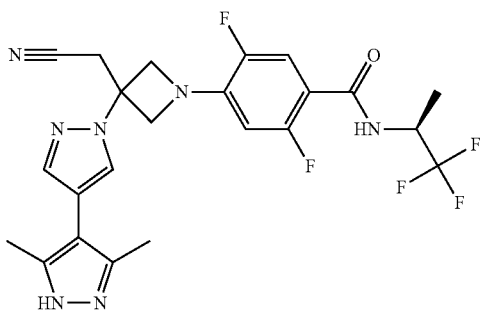 [SMILES: Cc1n[nH]c(C)c1-c1cnn(C2(CC#N)CN(c3cc(F)c(C(=O)N[C@@H](C)C(F)(F)F)cc3F)C2)c1]

Step 1: 2,4,5-Trifluoro-N-[(1S)-2,2,2-trifluoro-1-methylethyl]benzamide

To a solution of 2,4,5-trifluorobenzoic acid (5.00 g, 28.4 mmol) in acetonitrile (50 mL) was added N,N-dimethylformamide (40 μL) followed by addition of oxalyl chloride (3.60 mL, 42.6 mmol). After 90 min, the volatiles were removed under reduced pressure. The residue was co-evaporated with acetonitrile (50 mL). The residue was then dissolved in methylene chloride (50 mL). This solution was added drop-wise into a cooled (ice bath) mixture of (2S)-1,1,1-trifluoropropan-2-amine hydrochloride (5.52 g, 36.9 mmol) (from Synquest, 98% ee) in toluene (100 mL) and 0.5 M sodium hydroxide aqueous solution (142 mL, 71.0 mmol). After addition, the ice bath was removed, and the reaction was allowed to warm to rt. The reaction was stirred overnight. The organic layer was separated. The aqueous layer was extracted with methylene chloride (50 mL). The combined organic layers were washed with 20% brine (75 mL) and water (2×75 mL), dried over MgSO$_4$, filtered and concentrated under reduced pressure to afford the desired product (6.49 g, 84%) which was directly used in the next step without further purification. $^1$H NMR (300 MHz, DMSO-d$_6$) δ 9.01 (d, J=7.6 Hz, 1H), 7.92-7.50 (m, 2H), 4.76 (m, 1H), 1.31 (d, J=7.0 Hz, 3H) ppm. LCMS cacld. for $C_{10}H_8F_6NO$ (M+1)$^+$: m/z=272.0. Found: 272.0.

Step 2: 2,5-Difluoro-4-(3-hydroxyazetidin-1-yl)-N-[(1S)-2,2,2-trifluoro-1-methylethyl]benzamide A mixture of 2,4,5-trifluoro-N-[(1S)-2,2,2-trifluoro-1-methylethyl]benzamide (6.39 g, 23.6 mmol), azetidin-3-ol hydrochloride (3.19 g, 28.3 mmol) and 1,8-diazabicyclo[5.4.0]undec-7-ene (8.81 mL, 58.9 mmol) in acetonitrile (25 mL) was stirred at 80° C. for 2 h. The reaction mixture was diluted with EtOAc (75 mL) and washed with 1N HCl (50 mL), 1N NaHCO$_3$ (60 mL), 20% brine (50 mL) and water (75 mL). The aqueous layers were extracted with EtOAc (100 mL). The organic layers were combined, dried over MgSO$_4$, filtered and concentrated under reduced pressure to yield the desired product (7.59 g, 91.8%). $^1$H NMR (300 MHz, DMSO-d$_6$) δ 8.38 (dd, J=8.9, 1.9 Hz, 1H), 7.27 (dd, J=12.8, 6.5 Hz, 1H), 6.38 (dd, J=12.3, 7.5 Hz, 1H), 5.71 (d, J=6.4 Hz, 1H), 4.74 (dp, J=15.3, 7.6 Hz, 1H), 4.62-4.46 (m, 1H), 4.30-4.15 (m, 2H), 3.71 (m, 2H), 1.29 (d, J=7.1 Hz, 3H) ppm. LCMS cacld. for $C_{13}H_{14}F_5N_2O_2$ (M+1)$^+$: m/z=325.1. Found: 325.1.

Step 3: 2,5-Difluoro-4-(3-oxoazetidin-1-yl)-N-[(1S)-2,2,2-trifluoro-1-methylethyl]benzamide To a solution of 2,5-difluoro-4-(3-hydroxyazetidin-1-yl)-N-[(1S)-2,2,2-trifluoro-1-methylethyl]benzamide (7.57 g, 23.3 mmol) in methylene chloride (93 mL) was added iodobenzene diacetate (9.40 g, 29.2 mmol) and 2,2,6,6-tetramethyl-1-piperidinyloxy free radical (1.82 g, 11.7 mmol) (TEMPO) at room temperature. The reaction mixture was stirred at room temperature overnight. The mixture was diluted with EtOAc (100 mL), washed with 0.5N NaHCO$_3$ (2×80 mL), 20% brine (100 mL) and water (100 mL). The aqueous layers were extracted with ethyl acetate (75 mL). The organic extracts were combined, dried over MgSO$_4$, filtered and concentrated under reduced pressure. The residue was purified by flash chromatography on a silica gel column eluting with 0% to 5% ethyl acetate in methylene chloride to afford the crude product which was recrystallized from MTBE (50 mL) and heptane (100 mL) to give the desired product (5.44 g, 72%) as colorless solid. $^1$H NMR (300 MHz, DMSO-d$_6$) δ 8.52 (d, J=8.0 Hz, 1H), 7.36 (dd, J=12.5, 6.5 Hz, 1H), 6.63 (dd, J=12.1, 7.6 Hz, 1H), 4.90 (d, J=2.1 Hz, 4H), 4.86-4.68 (m, 1H), 1.31 (d, J=7.1 Hz, 3H) ppm. LCMS cacld. for $C_{13}H_{12}F_5N_2O_2$ (M+1)$^+$: m/z=323.1. Found: 323.0.

Step 4: 4-[3-(Cyanomethylene)azetidin-1-yl]-2,5-difluoro-N-[(1S)-2,2,2-trifluoro-1-methylethyl]benzamide Diethyl cyanomethylphosphonate (1.95 mL, 11.8 mmol) was added drop-wise to a cooled (ice bath) solution of 1.0 M potassium tert-butoxide in THF (11.8 mL, 11.8 mmol) which was diluted with tetrahydrofuran (12 mL). The bath was removed and the reaction was warmed to room temperature, and stirred for 90 min. The reaction solution was cooled with an ice bath again. The above prepared solution was then added over 12 min to a cooled (ice-bath) solution of 2,5-difluoro-4-(3-oxo azetidin-1-yl)-N-[(1S)-2,2,2-trifluoro-1-methylethyl]benzamide (4.00 g, 12.4 mmol) in tetrahydrofuran (50 mL). The reaction mixture was stirred for 30 min. The ice bath was removed, and the reaction was stirred at room temperature overnight, then quenched by the addition of 20% brine (75 mL) and ethyl acetate (75 mL). The organic layer was separated. The aqueous layer was extracted with ethyl acetate (50 mL). The combined organic layers were dried over $MgSO_4$, filtered and concentrated under reduced pressure. The residue was purified by flash chromatography on a silica gel column with ethyl acetate in hexanes (0% to 30%) to yield the desired product (2.6 g). $^1H$ NMR (400 MHz, DMSO-$d_6$) δ 8.59-8.37 (m, 1H), 7.33 (dd, J=12.5, 6.4 Hz, 1H), 6.59 (dd, J=12.0, 7.4 Hz, 1H), 5.88 (m, 1H), 4.94-4.75 (m, 4H), 4.76 (m, 1H), 1.31 (d, J=7.1 Hz, 3H) ppm. LCMS cacld. for $C_{15}H_{13}F_5N_3O$ (M+1)$^+$: m/z=346.1. Found: 346.1.

Step 5: 4-{3-(Cyanomethyl)-3-[4-(4,4,5,5-tetramethyl-1,3,2-dioxaborolan-2-yl)-1H-pyrazol-1-yl]azetidin-1-yl}-2,5-difluoro-N-[(1S)-2,2,2-trifluoro-1-methylethyl]benzamide A mixture of 4-(4,4,5,5-tetramethyl-1,3,2-dioxaborolan-2-yl)-1H-pyrazole (1.00 g, 5.15 mmol), 4-[3-(cyanomethylene)azetidin-1-yl]-2,5-difluoro-N-[(1S)-2,2,2-trifluoro-1-methylethyl]benzamide (1.78 g, 5.15 mmol) and 1,8-diazabicyclo[5.4.0]undec-7-ene (0.31 mL, 2.1 mmol) in acetonitrile (20.2 mL) was heated at 50° C. overnight. After cooling, the solvent was removed under reduced pressure. The residue was used in the next step without further purification. LCMS cacld. for $C_{24}H_{28}BF_5N_5O_3$ (M+1)$^+$: m/z=540.2. Found: 540.1.

Step 6: 4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide A mixture of 4-{3-(cyanomethyl)-3-[4-(4,4,5,5-tetramethyl-1,3,2-dioxaborolan-2-yl)-1H-pyrazol-1-yl]azetidin-1-yl}-2,5-difluoro-N-[(1S)-2,2,2-trifluoro-1-methylethyl]benzamide (329 mg, 0.610 mmol), 4-bromo-3,5-dimethyl-1H-pyrazole (206 mg, 1.18 mmol), tetrakis(triphenylphosphine)palladium(0) (110 mg, 0.098 mmol) and sodium carbonate (320 mg, 3.0 mmol) in 1,4-dioxane (10 mL)/water (5 mL) was purged with nitrogen and stirred at 110° C. for 1 h. The reaction mixture was diluted with EtOAc, washed with water and brine, concentrated. The residue was purified first with silica gel (eluting with 0-100% EtOAc/hexanes followed by 10% methanol/dichloromethane), and then by prep-LCMS (XBridge C18 column, eluting with a gradient of acetonitrile/water containing 0.1% ammonium hydroxide, at flow rate of 60 mL/min) to give the desired product (30 mg, 9.7%). $^1H$ NMR (500 MHz, DMSO-$d_6$) δ 12.17 (1H, s), 8.45 (1H, d, J=8.0 Hz), 8.10 (1H, s), 7.70 (1H, s), 7.34 (1H, m), 6.61 (1H, s), 4.77 (1H, m), 4.62 (2H, d, J=9.0 Hz), 4.39 (1H, d, J=9.0 Hz), 3.64 (2H, s), 2.22 (6H, s), 1.31 (6H, d, J=7.0 Hz) ppm. LCMS calculated for $C_{23}H_{23}F_5N_7O$ (M+H)$^+$: m/z=508.2. Found: 508.0.

Example A1: PI3K Enzyme Assay

PI3-Kinase luminescent assay kit including lipid kinase substrate, D-myo-phosphatidylinositol 4,5-bisphosphate (PtdIns(4,5)P2)D (+)-sn-1,2-di-O-octanoylglyceryl, 3-O-phospho linked (PIP2), biotinylated I(1,3,4,5)P4, PI(3,4,5) P3 Detector Protein is purchased from Echelon Biosciences (Salt Lake City, Utah). AlphaScreen™ GST Detection Kit including donor and acceptor beads was purchased from PerkinElmer Life Sciences (Waltham, Mass.). PI3Kδ (p110δ/p85α) is purchased from Millipore (Bedford, Mass.). ATP, $MgCl_2$, DTT, EDTA, HEPES and CHAPS are purchased from SigmaAldrich (St. Louis, Mo.).

AlphaScreen™ Assay for PI3Kδ

The kinase reaction are conducted in 384-well REMP plate from Thermo Fisher Scientific in a final volume of 40 μL. Inhibitors are first diluted serially in DMSO and added to the plate wells before the addition of other reaction components. The final concentration of DMSO in the assay is 2%. The PI3K assays are carried out at room temperature in 50 mM HEPES, pH 7.4, 5 mM $MgCl_2$, 50 mM NaCl, 5 mM DTT and CHAPS 0.04%. Reactions are initiated by the addition of ATP, the final reaction mixture consisted of 20 μM PIP2, 20 μM ATP, 1.2 nM PI3Kδ are incubated for 20 minutes. 10 μL of reaction mixture are then transferred to 5 μL 50 nM biotinylated I(1,3,4,5)P4 in quench buffer: 50 mM HEPES pH 7.4, 150 mM NaCl, 10 mM EDTA, 5 mM DTT, 0.1% Tween-20, followed with the addition of 10 μL AlphaScreen™ donor and acceptor beads suspended in quench buffer containing 25 nM PI(3,4,5)P3 detector protein. The final concentration of both donor and acceptor beads is 20 mg/ml. After plate sealing, the plate are incubated in a dark location at room temperature for 2 hours. The activity of the product is determined on Fusion-alpha microplate reader (PerkinElmer). $IC_{50}$ determination is performed by fitting the curve of percent control activity versus the log of the inhibitor concentration using the GraphPad Prism 3.0 software.

Example A2: PI3K Enzyme Assay

Materials: Lipid kinase substrate, phosphoinositol-4,5-bisphosphate (PIP2), are purchased from Echelon Biosciences (Salt Lake City, Utah). PI3K isoforms α, β, δ and γ are purchased from Millipore (Bedford, Mass.). ATP, $MgCl_2$, DTT, EDTA, MOPS and CHAPS are purchased from SigmaAldrich (St. Louis, Mo.).

The kinase reactions are conducted in clear-bottom 96-well plate from Thermo Fisher Scientific in a final volume of 24 μL. Inhibitors are first diluted serially in DMSO and added to the plate wells before the addition of other reaction components. The final concentration of DMSO in the assay is 0.5%. The PI3K assays are carried out at room temperature in 20 mM MOPS, pH 6.7, 10 mM $MgCl_2$, 5 mM DTT and CHAPS 0.03%. The reaction mixture is prepared containing 50 μM PIP2, kinase and varying concentration of inhibitors. Reactions are initiated by the addition of ATP containing 2.2 μCi [γ-$^{33}$P]ATP to a final concentration of 1000 μM. The final concentration of PI3K isoforms α, β, δ and γ in the assay were 1.3, 9.4, 2.9 and 10.8 nM, respectively. Reactions are incubated for 180 minutes and terminated by the addition of 100 μL of 1 M potassium phosphate pH 8.0, 30 mM EDTA quench buffer. A 100 μL aliquot of the reaction solution are then transferred to 96-well Millipore MultiScreen IP 0.45 μm PVDF filter plate (The filter plate is prewetted with 200 μL 100% ethanol, distilled water, and 1 M potassium phosphate pH 8.0, respectively). The filter plate is aspirated on a Millipore Manifold under vacuum and washed with 18×200 μL wash buffer containing 1 M potassium phosphate pH 8.0 and 1 mM ATP. After drying by aspiration and blotting, the plate is air dried in an incubator at 37° C. overnight. Packard TopCount adapter (Millipore) is then attached to the plate followed with addition of 120 µL Microscint 20 scintillation cocktail (Perkin Elmer) in each well. After the plate sealing, the radioactivity of the product is determined by scintillation counting on Topcount (Perkin Elmer). $IC_{50}$ determination is performed by fitting the curve of percent control activity versus the log of the inhibitor concentration using the GraphPad Prism 3.0 software.

Example A3: PI3Kδ Scintillation Proximity Assay

Materials

[γ-$^{33}$P]ATP (10 mCi/mL) was purchased from PerkinElmer (Waltham, Mass.). Lipid kinase substrate, D-myo-Phosphatidylinositol 4,5-bisphosphate (PtdIns(4,5)P2)D(+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) was purchased from Millipore (Bedford, Mass.). ATP, $MgCl_2$, DTT, EDTA, MOPS and CHAPS were purchased from SigmaAldrich (St. Louis, Mo.). Wheat Germ Agglutinin (WGA) YSi SPA Scintillation Beads was purchased from GE healthcare life sciences (Piscataway, N.J.).

The kinase reaction was conducted in polystyrene 384-well matrix white plate from Thermo Fisher Scientific in a final volume of 25 µL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 µM PIP2, 20 µM ATP, 0.2 µCi [γ-$^{33}$P] ATP, 4 nM PI3Kδ. Reactions were incubated for 210 min and terminated by the addition of 40 µL SPA beads suspended in quench buffer: 150 mM potassium phosphate pH 8.0, 20% glycerol. 25 mM EDTA, 400 µM ATP. The final concentration of SPA beads was 1.0 mg/mL. After the plate sealing, plates were shaken overnight at room temperature and centrifuged at 1800 rpm for 10 minutes, the radioactivity of the product was determined by scintillation counting on Topcount (PerkinElmer). $IC_{50}$ determination was performed by fitting the curve of percent control activity versus the log of the inhibitor concentration using the GraphPad Prism 3.0 software. $IC_{50}$ data for the Examples is presented in Table 2 as determined by Assay A3.

TABLE 2

| Example # | PI3Kδ $IC_{50}$ (nM)* |
|---|---|
| 1 | + |
| 1A | + |
| 1B | ++ |
| 1C | + |
| 1D | ++ |
| 2 | + |
| 2A | + |
| 2B | ++ |
| 2C | + |
| 2D | ++ |
| 3 | + |
| 4 | + |

*column symbols (for Table 2):
+ refers to ≤100 nM
++ refers to >100 nM to 400 nM Example B1: B Cell Proliferation Assay To acquire B cells, human PBMC are isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells are then purified by positive immunosorting using an autoMacs (Miltenyi Biotech) according to the manufacture's instruction.

The purified B cells ($2\times10^5$/well/200 µL) are cultured in 96-well ultra-low binding plates (Corning, Corning, N.Y.) in RPMI1640, 10% FBS and goat F(ab')2 anti-human IgM (10 µg/ml) (Invitrogen, Carlsbad, Calif.) in the presence of different amount of test compounds for three days. [$^3$H]-thymidine (µCi/well) (PerkinElmer, Boston, Mass.) in PBS is then added to the B cell cultures for an additional 12 hours before the incorporated radioactivity is separated by filtration with water through GF/B filters (Packard Bioscience, Meriden, Conn.) and measured by liquid scintillation counting with a TopCount (Packard Bioscience).

Example B2: Pfeiffer Cell Proliferation Assay

Pfeiffer cell line (diffuse large B cell lymphoma) are purchased from ATCC (Manassas, Va.) and maintained in the culture medium recommended (RPMI and 10% FBS). To measure the anti-proliferation activity of the compounds, the Pfeiffer cells are plated with the culture medium ($2\times10^3$ cells/well/per 200 µl) into 96-well ultra-low binding plates (Corning, Corning, N.Y.), in the presence or absence of a concentration range of test compounds. After 3-4 days, [$^3$H]-thymidine (µCi/well) (PerkinElmer, Boston, Mass.) in PBS is then added to the cell culture for an additional 12 hours before the incorporated radioactivity is separated by filtration with water through GF/B filters (Packard Bioscience, Meriden, Conn.) and measured by liquid scintillation counting with a TopCount (Packard Bioscience).

Example B3: SUDHL-6 Cell Proliferation Assay

SUDHL-6 cell line (diffuse large B cell lymphoma) was purchased from ATCC (Manassas, Va.) and maintained in the culture medium recommended (RPMI and 10% FBS). To measure the anti-proliferation activity of the compounds through ATP quantitation, the SUDHL-6 cells was plated with the culture medium (5000 cells/well/per 200 µl) into 96-well polystyrene clear black tissue culture plate (Greiner-bio-one through VWR, NJ) in the presence or absence of a concentration range of test compounds. After 3 days, Cell Titer-GLO Luminescent (Promega, Madison, Wis.) cell culture agent was added to each well for 10 minutes at room temperature to stabilize the luminescent signal. This determines the number of viable cells in culture based on quantitation of the ATP present, which signals the presence of metabolically active cells. Luminescence was measured with the TopCount 384 (Packard Bioscience through Perkin Elmer, Boston, Mass.). $IC_{50}$ data for the Examples is presented in Table 3 determined by the assay of Example B3.

TABLE 3

| Example # | SUDHL6 $IC_{50}$ (nM) |
|---|---|
| 1A | + |
| 1C | + |
| 2A | + |
| 2C | + |
| 3 | + |
| 4 | + |

* column symbols (for Table 3):
+ refers to ≤500 nM

Example C: Akt Phosphorylation Assay

Ramos cells (B lymphocyte from Burkitts lymphoma) are obtained from ATCC (Manassas, Va.) and maintained in RPMI1640 and 10% FBS. The cells ($3\times10^7$ cells/tube/3 mL in RPMI) are incubated with different amounts of test compounds for 2 hrs at 37° C. and then stimulated with goat F(ab')2 anti-human IgM (5 μg/mL) (Invitrogen) for 17 minutes in a 37° C. water bath. The stimulated cells are spun down at 4° C. with centrifugation and whole cell extracts are prepared using 300 μL lysis buffer (Cell Signaling Technology, Danvers, Mass.). The resulting lysates are sonicated and supernatants are collected. The phosphorylation level of Akt in the supernatants are analyzed by using PathScan phospho-Aktl (Ser473) sandwich ELISA kits (Cell Signaling Technology) according to the manufacturer's instruction.

Example J: In Vitro JAK Kinase Assay

The compounds in Table 1 were tested for inhibitory activity of JAK targets according to the following in vitro assay described in Park et al., Analytical Biochemistry 1999, 269, 94-104. The catalytic domains of human JAK1 (a.a. 837-1142), JAK2 (a.a. 828-1132) and JAK3 (a.a. 781-1124) were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the 40 μL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions was 1 mM. Reactions were carried out at room temperature for 1 hour and then stopped with 20 μL 45 mM EDTA, 300 nM SA-APC, 6 nM Eu—Py20 in assay buffer (Perkin Elmer, Boston, Mass.). Binding to the Europium labeled antibody took place for 40 minutes and HTRF signal was measured on a PHERA star plate reader (BMG, Cary, N.C.). The data for the JAK1 and/or JAK2 inhibitors were obtained by testing the compounds in the Example J assay at 1 mM ATP.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (I):

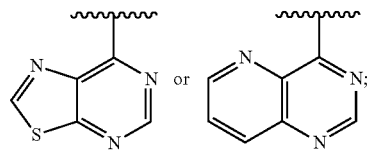

(I)

or a pharmaceutically acceptable salt thereof, wherein:

Ar is:

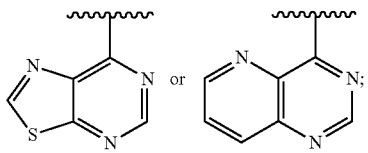

$R^1$ is methyl;

$R^2$ is $C_{1-6}$ alkoxy, $C_{1-6}$ haloalkoxy, or phenyl; wherein said phenyl is optionally substituted by 1, 2, or 3 substituents independently selected from halo, OH, CN, $C_{1-4}$ alkyl, $C_{1-4}$ alkoxy, and $C_{1-4}$ haloalkoxy;

$R^3$ is Cy or C(=O)$NR^cR^d$;

provided that either (i) $R^2$ is phenyl, wherein said phenyl is optionally substituted by 1, 2, or 3 substituents independently selected from halo, OH, CN, $C_{1-4}$ alkyl, $C_{1-4}$ alkoxy, and $C_{1-4}$ haloalkoxy; or (ii) $R^3$ is Cy;

$R^4$ is halo, $C_{1-4}$ alkyl, or $C_{1-4}$ haloalkyl;

$R^5$ is halo, CN, $C_{1-4}$ alkyl, or $C_{1-4}$ haloalkyl;

$R^6$ is H;

each Cy is independently selected from 4-6 membered heterocycloalkyl or 5-6 membered heteroaryl, each of which is optionally substituted with 1 or 2 independently selected $R^{3b}$ groups;

each $R^c$ and $R^d$ is independently selected from H and $C_{1-6}$ alkyl; and each $R^{3b}$ is independently selected from halo, CN, $C_{1-6}$ alkyl, $C_{1-6}$ haloalkyl, hydroxy, $C_{1-6}$ alkoxy, $C_{1-6}$ haloalkoxy, amino, $C_{1-6}$ alkylamino, di($C_{1-6}$ alkyl)amino, $C_{1-6}$ alkylsulfonyl, carbamyl, $C_{1-6}$ alkylcarbamyl, and di($C_{1-6}$ alkyl)carbamyl.

2. The compound of claim 1, or a pharmaceutically acceptable salt thereof, wherein $R^2$ is $C_{1-6}$ alkoxy or phenyl; wherein said phenyl is optionally substituted by 1, 2, or 3 substituents independently selected from halo, OH, CN, $C_{1-4}$ alkyl, $C_{1-4}$ alkoxy, and $C_{1-4}$ haloalkoxy.

3. The compound of claim 1, or a pharmaceutically acceptable salt thereof, wherein $R^2$ is methoxy or ethoxy.

4. The compound of claim 1, or a pharmaceutically acceptable salt thereof, wherein $R^2$ is phenyl; wherein said phenyl is optionally substituted by 1, 2, or 3 independently selected halo groups.

5. The compound of claim 1, or a pharmaceutically acceptable salt thereof, wherein $R^3$ is Cy, C(=O)$NR^cR^d$.

6. The compound of claim 1, or a pharmaceutically acceptable salt thereof, wherein $R^3$ is Cy.

7. The compound of claim 1, or a pharmaceutically acceptable salt thereof, wherein $R^3$ is:

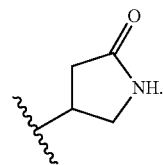 [SMILES: *C1CNC(=O)C1]

8. The compound of claim 1, or a pharmaceutically acceptable salt thereof, wherein $R^4$ is $C_{1-4}$ alkyl or halo.

9. The compound of claim 1, or a pharmaceutically acceptable salt thereof, wherein $R^4$ is methyl or fluoro.

10. The compound of claim 1, or a pharmaceutically acceptable salt thereof, wherein $R^5$ is halo, CN, or methyl.

11. The compound of claim 1, or a pharmaceutically acceptable salt thereof, wherein $R^5$ is chloro.

12. The compound of claim 1, or a pharmaceutically acceptable salt thereof, wherein:

Ar is:

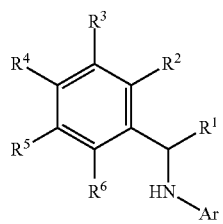

$R^2$ is $C_{1-6}$ alkoxy or phenyl, wherein said phenyl is optionally substituted by 1, 2, or 3 independently selected halo groups;

$R^3$ is $C(=O)NR^cR^d$, 4-6 membered heterocycloalkyl, or 5-6 membered heteroaryl;

wherein said 4-6 membered heterocycloalkyl and 5-6 membered heteroaryl is optionally substituted by 1, 2, or 3 independently selected $R^{3b}$ groups;

each $R^{3b}$ is independently selected from halo, CN, $C_{1-6}$ alkyl, $C_{1-6}$ haloalkyl, hydroxy, $C_{1-6}$ alkoxy, $C_{1-6}$ haloalkoxy, amino, $C_{1-6}$ alkylamino, di($C_{1-6}$ alkyl)amino, $C_{1-6}$ alkylsulfonyl, carbamyl, $C_{1-6}$alkylcarbamyl, and di($C_{1-6}$alkyl)carbamyl;

$R^4$ is $C_{1-4}$ alkyl or halo;

$R^5$ is halo; and $R^6$ is H.

13. The compound of claim 1, or a pharmaceutically acceptable salt thereof, wherein:

Ar is:

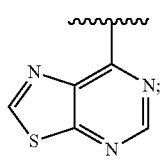

$R^2$ is $C_{1-6}$ alkoxy;

$R^3$ is 4-6 membered heterocycloalkyl;

$R^4$ and $R^5$ are each independently halo; and $R^6$ is H.

14. The compound of claim 1, or a pharmaceutically acceptable salt thereof, wherein:

Ar is:

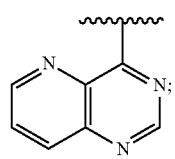 [SMILES: *c1ncnc2cccnc12]

$R^2$ is $C_{1-6}$ alkoxy or phenyl, wherein said phenyl is optionally substituted by 1, 2, 3, or 4 independently selected halo groups;

$R^3$ is $C(=O)NR^cR^d$, 4-6 membered heterocycloalkyl, or 5-6 membered heteroaryl;

wherein said 4-6 membered heterocycloalkyl and 5-6 membered heteroaryl is optionally substituted by 1, 2, or 3 independently selected $R^{3b}$ groups;

each $R^{3b}$ is di($C_{1-6}$ alkyl)carbamyl;

$R^4$ is halo or $C_{1-4}$ alkyl;

$R^5$ is halo; and $R^6$ is H.

15. The compound of claim 12, having Formula (II):

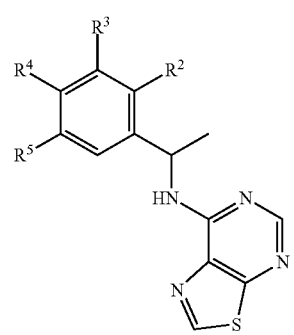

(II)

or a pharmaceutically acceptable salt thereof.

16. The compound of claim 12, having Formula (III):

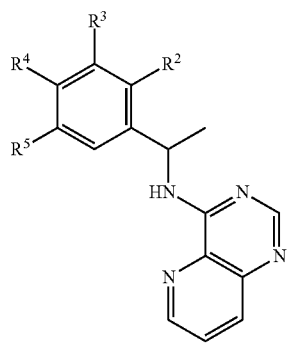

(III)

or a pharmaceutically acceptable salt thereof.

17. The compound of claim 12, having Formula (IIa):

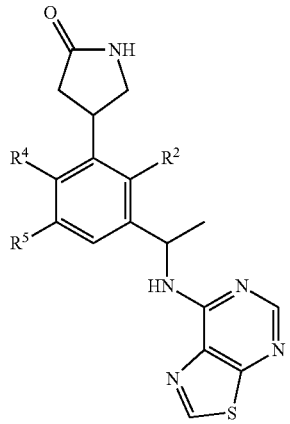

(IIa)

or a pharmaceutically acceptable salt thereof.

18. The compound of claim 12, having Formula (IIIa):

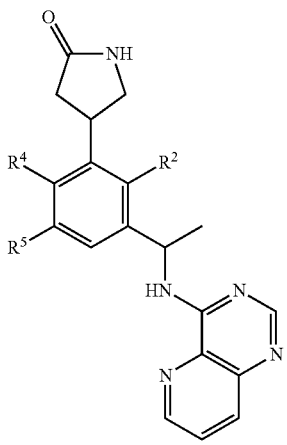

(IIIa)

or a pharmaceutically acceptable salt thereof.

19. The compound of claim 1, wherein the compound is selected from:
- 4-{3-chloro-6-ethoxy-2-fluoro-5-[1-([1,3]thiazolo[5,4-d]pyrimidin-7-ylamino)ethyl]phenyl}pyrrolidin-2-one;
- 4-{3-chloro-6-ethoxy-2-fluoro-5-[1-(pyrido[3,2-d]pyrimidin-4-ylamino)ethyl]phenyl}pyrrolidin-2-one;
- 5-{3-chloro-6-methoxy-2-methyl-5-[(1 S)-1-(pyrido[3,2-d]pyrimidin-4-ylamino)ethyl]phenyl}-N,N-dimethyl-pyridine-2-carboxamide;
- 4-chloro-N-ethyl-3',5'-difluoro-3-methyl-6-[1-(pyrido[3,2-d]pyrimidin-4-ylamino)ethyl]biphenyl-2-carboxamide;

or a pharmaceutically acceptable salt thereof.

20. The compound of claim 1, selected from:
- (S)-4-(3-chloro-6-ethoxy-2-fluoro-5-((S)-1-(pyrido[3,2-d]pyrimidin-4-ylamino)ethyl)phenyl)pyrrolidin-2-one;
- (R)-4-(3-chloro-6-ethoxy-2-fluoro-5-((R)-1-(pyrido[3,2-d]pyrimidin-4-ylamino)ethyl)phenyl)pyrrolidin-2-one;
- (S)-4-(3-chloro-6-ethoxy-2-fluoro-5-((R)-1-(pyrido[3,2-d]pyrimidin-4-ylamino)ethyl)phenyl)pyrrolidin-2-one; and
- (R)-4-(3-chloro-6-ethoxy-2-fluoro-5-((S)-1-(pyrido[3,2-d]pyrimidin-4-ylamino)ethyl)phenyl)pyrrolidin-2-one;

or a pharmaceutically acceptable salt thereof.

21. A pharmaceutical composition comprising a compound of claim 1, or a pharmaceutically acceptable salt thereof, and at least one pharmaceutically acceptable carrier.

22. The compound of claim 1, or a pharmaceutically acceptable salt thereof, wherein $R^3$ is selected from the group consisting of pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, and benzazapene.

23. The compound of claim 1, or a pharmaceutically acceptable salt thereof, wherein $R^3$ is pyrrolidin-2-one.

24. The compound of claim 1, or a pharmaceutically acceptable salt thereof, wherein $R^3$ is 1,3-isoxazolidin-2-one.

* * * * *

UNITED STATES PATENT AND TRADEMARK OFFICE
CERTIFICATE OF CORRECTION

PATENT NO. : 10,077,277 B2
APPLICATION NO. : 14/735438
DATED : September 18, 2018
INVENTOR(S) : Yun-Long Li and Andrew P. Combs Page 1 of 1

It is certified that error appears in the above-identified patent and that said Letters Patent is hereby corrected as shown below:

In the Claims

Column 96, Line 36, Claim 5, delete "is Cy," and insert -- is --.

Column 98, Line 45, Claim 17, delete "(Ha):" and insert -- (IIa): --.

Column 99, Line 1, Claim 18, delete "(Ma):" and insert -- (IIIa): --.

Column 99, Line 30, Claim 19, delete "[(1 S)" and insert -- [(1S) --.

Column 100, Line 22, Claim 22, delete "tetrahydropuran" and insert -- tetrahydropyran --.

Column 100, Line 26, Claim 22, delete "benzazapene." and insert -- benzazepine. --.

Signed and Sealed this
Twenty-fourth Day of December, 2019

Andrei Iancu
*Director of the United States Patent and Trademark Office*